United States Patent
Shin et al.

(10) Patent No.: US 11,258,019 B2
(45) Date of Patent: *Feb. 22, 2022

(54) ORGANIC COMPOUND, ORGANIC LIGHT EMITTING DIODE INCLUDING THE SAME, AND ORGANIC LIGHT EMITTING DISPLAY

(71) Applicant: LG Display Co., Ltd., Seoul (KR)

(72) Inventors: Jicheol Shin, Seoul (KR); Seonkeun Yoo, Gunpo-si (KR); Seunghee Yoon, Seoul (KR)

(73) Assignee: LG Display Co., Ltd., Seoul (KR)

( * ) Notice: Subject to any disclaimer, the term of this patent is extended or adjusted under 35 U.S.C. 154(b) by 464 days.

This patent is subject to a terminal disclaimer.

(21) Appl. No.: 16/216,764

(22) Filed: Dec. 11, 2018

(65) Prior Publication Data

US 2019/0181354 A1 Jun. 13, 2019

(30) Foreign Application Priority Data

Dec. 13, 2017 (KR) .......................... 10-2017-0171677

(51) Int. Cl.
*H01L 51/00* (2006.01)
*C07D 471/04* (2006.01)
(Continued)

(52) U.S. Cl.
CPC ........ *H01L 51/0072* (2013.01); *C07D 471/04* (2013.01); *H01L 27/322* (2013.01);
(Continued)

(58) Field of Classification Search
None
See application file for complete search history.

(56) References Cited

U.S. PATENT DOCUMENTS 9,768,390 B2 9/2017 Yen
9,773,983 B2 9/2017 Kang et al.
(Continued)

FOREIGN PATENT DOCUMENTS

CN 102372709 A 3/2012
CN 104603137 A 5/2015
(Continued)

*Primary Examiner* — Robert S Loewe
(74) *Attorney, Agent, or Firm* — Seed IP Law Group LLP

(57) ABSTRACT

Disclosed herein is an organic compound, an organic light emitting diode including the same, and an organic light emitting display. The organic compound according to the present disclosure is a phenanthroline compound represented by the following Formula 1, which is used as an electron transport material of an organic light emitting diode. The phenanthroline compound can increase lifespan of the organic light emitting diode while reducing driving voltage of the organic light emitting diode.

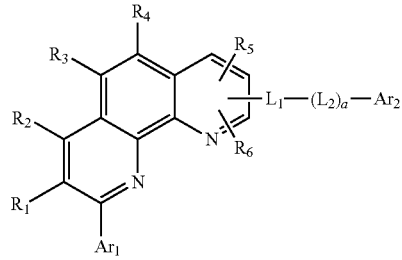

5 Claims, 16 Drawing Sheets

(51) Int. Cl.
   *H01L 27/32*   (2006.01)
   *H01L 51/50*   (2006.01)
   *H01L 51/52*   (2006.01)

(52) U.S. Cl.
   CPC ...... *H01L 27/3209* (2013.01); *H01L 27/3244* (2013.01); *H01L 51/5016* (2013.01); *H01L 51/5044* (2013.01); *H01L 51/5072* (2013.01); *H01L 51/5278* (2013.01)

(56) References Cited

U.S. PATENT DOCUMENTS

| | | | |
|---|---|---|---|
| 9,831,444 | B1 | 11/2017 | Yen et al. |
| 9,871,206 | B2 | 1/2018 | Mizutani et al. |
| 10,510,964 | B2 | 12/2019 | Mizutani et al. |
| 10,879,472 | B2 | 12/2020 | Yoo et al. |
| 2014/0183471 | A1* | 7/2014 | Heo ............... H01L 51/504 257/40 |
| 2015/0303380 | A1 | 10/2015 | Kambe et al. |
| 2016/0043327 | A1* | 2/2016 | Yoo ............... H01L 51/0058 257/40 |
| 2016/0104844 | A1* | 4/2016 | Kang ............. H01L 51/006 257/40 |
| 2016/0197289 | A1 | 7/2016 | Sado et al. |
| 2017/0271607 | A1* | 9/2017 | Kambe ......... H01L 51/5016 |
| 2018/0019407 | A1 | 1/2018 | Sakaino et al. |
| 2018/0090719 | A1* | 3/2018 | Han ............... H01L 51/5221 |
| 2018/0102484 | A1* | 4/2018 | Mizutani ...... H01L 51/0067 |
| 2018/0130953 | A1* | 5/2018 | Song ............. H01L 51/0071 |
| 2018/0166647 | A1 | 6/2018 | Shin et al. |
| 2018/0366652 | A1 | 12/2018 | Mo et al. |
| 2019/0233398 | A1* | 8/2019 | Oh ................. C07D 401/10 |
| 2020/0066996 | A1* | 2/2020 | La ................. H01L 51/0054 |

FOREIGN PATENT DOCUMENTS

| | | |
|---|---|---|
| CN | 104871332 A | 8/2015 |
| CN | 105272979 A | 1/2016 |
| CN | 105514287 A | 4/2016 |
| CN | 106008498 A | 10/2016 |
| CN | 106565705 A | 4/2017 |
| CN | 106986870 A | 7/2017 |
| CN | 107207503 A | 9/2017 |
| CN | 107556307 A | 1/2018 |
| CN | 108218858 A | 6/2018 |
| KR | 10-2012-0056418 A | 6/2012 |
| KR | 10-2015-0026055 A | 3/2015 |
| KR | 10-2015-0099750 A | 9/2015 |
| KR | 10-2016-0043636 A | 4/2016 |
| KR | 10-2017-0127379 A | 11/2017 |
| KR | 10-2018-0067321 A | 6/2018 |
| TW | 201730180 A | 9/2017 |
| WO | 2015/064969 A3 | 5/2015 |

* cited by examiner

ORGANIC COMPOUND, ORGANIC LIGHT EMITTING DIODE INCLUDING THE SAME, AND ORGANIC LIGHT EMITTING DISPLAY

BACKGROUND

Technical Field

The present disclosure relates to an organic compound for charge generation layer and/or electron transport materials, an organic light emitting diode including the same, and an organic light emitting display including the same.

Description of the Related Art

Recently, there is increasing interest in flat display elements occupying a small space, with increasing size of displays. A technology of an organic light emitting display including organic light emitting diodes (OLEDs) as the flat display elements has been rapidly developed in the art.

An OLED emits light through annihilation of pairs of holes and electrons created upon injection of holes and electrons from a hole injection electrode (anode) and an electron injection electrode (cathode) into a light emitting material layer (EML) interposed between the anode and the cathode. Advantageously, such an OLED is formed on a flexible transparent substrate, such as plastic, is operable at a low voltage (10 V or less), consumes relatively low power, and provides good color reproduction.

Recently, OLEDs emitting white light have been used in various fields such as lighting apparatuses, slim light sources, backlight units for liquid crystal displays, or full-color displays using a color filter.

For white OLEDs, high efficiency, long lifespan, color purity, current/voltage-dependent color stability, and ease of fabrication are recognized as important factors. Generally, white OLEDs may be classified into a single-stack type and a multi-stack type. In order to implement a long-lifespan white OLED, a tandem OLED, that is, an OLED having a structure in which multiple light emitting units are stacked, has been mainly used.

For example, a tandem white OLED includes a first light emitting stack including a blue light emitting layer and a second light emitting stack including a yellow-green light emitting layer, wherein the first and second light emitting stacks are vertically stacked. Such a white OLED emits white light by mixing light emitted from the blue light emitting layer with light emitted from the yellow-green light emitting layer.

In addition, the OLED includes a charge generation layer interposed between the first light emitting stack and the second light emitting stack to improve current efficiency in each light emitting layer while securing efficient distribution of charges to the light emitting stacks. Generally, the charge generation layer has a PN junction in which an N-type charge generation layer and a P-type charge generation layer are sequentially stacked.

In such a charge generation layer used in a typical tandem OLED, due to a difference in energy level between the N-type charge generation layer and the P-type charge generation layer, charges are generated at an interface between the P-type charge generation layer and an adjacent hole injection layer or hole transport layer, causing deterioration in electron injection into the N-type charge generation layer.

When the N-type charge generation layer is doped with a metal, the metal is likely to diffuse into the P-type charge generation layer, causing reduction in lifespan of the OLED. Particularly, a typical material for charge generation layers does not have sufficient thermal/electrical stability. Accordingly, long-term operation of the white OLED causes the material for charge generation layers to be degraded or deteriorated. As a result, not only efficiency in electron injection from the interface between the P-type charge generation layer and the adjacent hole injection layer or hole transport layer into the N-type charge generation layer but also efficiency in electron injection from the N-type charge generation layer into an adjacent electron transport layer can be greatly reduced, causing reduction in performance and lifespan of the OLED.

BRIEF SUMMARY

It is an aspect of the present disclosure to provide an organic compound which has good electron injection/electron transport characteristics while exhibiting high thermal stability.

It is another aspect of the present disclosure to provide an organic light emitting diode which has reduced driving voltage while exhibiting improved emission performance and lifespan, and an organic light emitting display including the same.

In accordance with one aspect of the present disclosure, there is provided an organic compound represented by Formula 1:

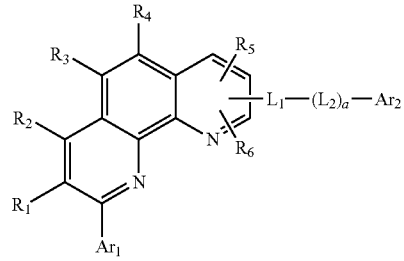

wherein $R_1$ to $R_6$ are each independently hydrogen, deuterium, tritium, an unsubstituted or substituted $C_1$ to $C_{20}$ alkyl group, an unsubstituted or substituted $C_1$ to $C_{20}$ alkoxy group, an unsubstituted or substituted $C_5$ to $C_{60}$ aryl group, or an unsubstituted or substituted $C_4$ to $C_{60}$ heteroaryl group;

$L_1$ and $L_2$ are each independently any one of the following formulae:

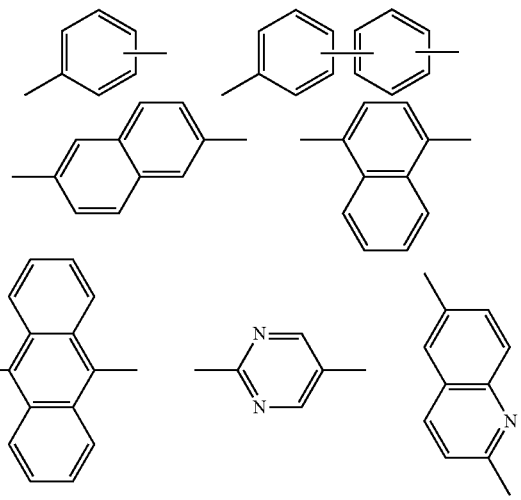

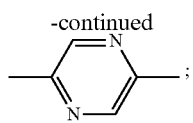

a is 0 or 1; and

Ar$_1$ and Ar$_2$ are each independently an unsubstituted or substituted C$_5$ to C$_{60}$ aryl group or an unsubstituted or substituted C$_4$ to C$_{30}$ heteroaryl group.

In the compound represented by Formula 1, when a is 1, L$_1$ together with L$_2$ are presented by any one of the following formulae:

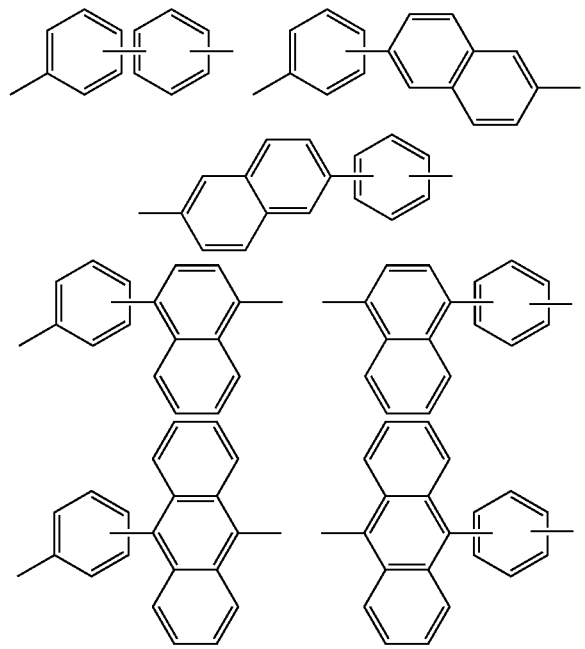

In accordance with another aspect of the present disclosure, there is provided a tandem organic light emitting diode using the organic compound set forth above as a material for a charge generation layer and/or an electron transport layer.

In accordance with a further aspect of the present disclosure, there is provided an organic light emitting display including the organic light emitting diode set forth above.

An organic compound according to the present disclosure has a phenanthroline moiety substituted with at least one aromatic ring. Since the organic compound has a high decomposition temperature or a high glass transition temperature to exhibit good thermal stability due to the presence of the aromatic ring-substituted phenanthroline moiety, the organic compound is prevented from being deteriorated or degraded by Joule's heat generated upon operation thereof. Accordingly, when used in an organic light emitting diode, the organic compound can improve lifespan of the organic light emitting diode while reducing driving voltage thereof.

In addition, since the phenanthroline moiety of the organic compound has a nitrogen atom having a sp2 hybrid orbital, which is relatively rich in electrons, the organic compound has good electron transport properties. Thus, the organic compound can be used as a material for an electron transport layer. In particular, the nitrogen atom of the phenanthroline moiety is bonded to an alkali metal or alkali earth metal compound, which is a dopant for an N-type charge generation layer, to form a gap state. As a result, a difference in energy level between the N-type charge generation layer and a P-type charge generation layer is reduced, thereby facilitating injection of electrons into the N-type charge generation layer while maximizing transfer of electrons from the N-type charge generation layer to an adjacent electron transport layer.

Namely, use of the organic compound in the N-type charge generation layer of the organic light emitting diode or the organic light emitting display allows efficient transfer of electrons from the N-type charge generation layer to the electron transport layer.

Further, since the organic compound containing nitrogen atoms is combined with the alkali metal or alkali earth metal compound in the N-type charge generation layer, the alkali metal or alkali earth metal compound can be prevented from diffusing into the P-type charge generation layer. As a result, deterioration in lifespan of the organic light emitting diode can be prevented.

LIST OF MAIN REFERENCE NUMERALS

Figure 1:
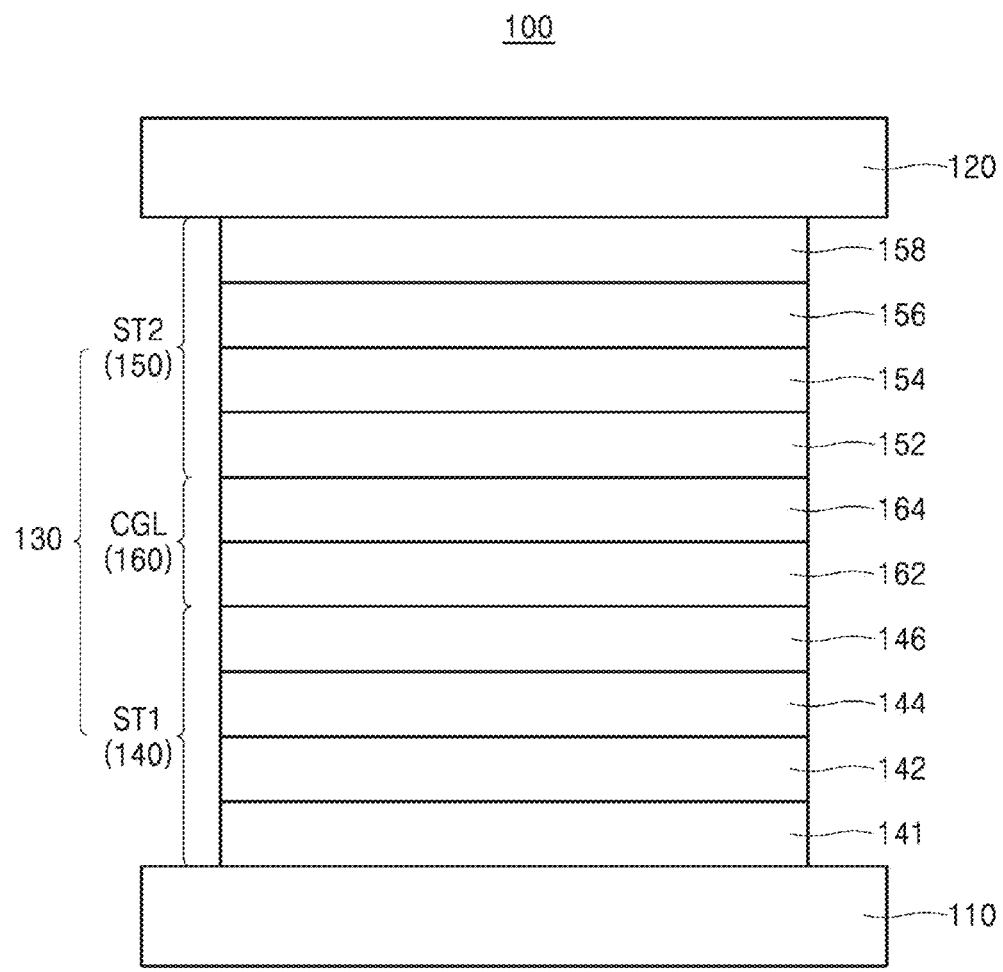
FIG. 1 is a schematic sectional view of an organic light emitting diode including a charge generation layer between two light emitting stacks according to an embodiment of the present disclosure, wherein the charge generation layer includes an organic compound represented by Formula 1.

- 100, 200, 400: organic light emitting diode
- 110, 210, 410: first electrode
- 120, 220, 420: second electrode
- 130, 230, 430: organic light emitting layer
- 140, 240: first light emitting stack (first light emitting unit)
- 150, 250: second light emitting stack (second light emitting unit)
- 160, 260, 280: charge generation layer
- 162, 262, 282: N-type charge generation layer
- 164, 264, 284: P-type charge generation layer
- 270: third light emitting stack (third light emitting unit)
- 300: organic light emitting display

DETAILED DESCRIPTION

Hereinafter, embodiments of the present disclosure will be described in detail with reference to the accompanying drawings such that the technical idea of the present disclosure can be easily realized by those skilled in the art. It should be understood that the present disclosure is not limited to the following embodiments and may be embodied in different ways.

In the drawings, portions irrelevant to the description will be omitted for clarity and like components will be denoted by like reference numerals throughout the specification. In addition, description of known functions and constructions which may unnecessarily obscure the subject matter of the present disclosure will be omitted.

It will be understood that, when an element such as a layer, film, region or substrate is referred to as being placed "above"/"below" or "on"/"under" another element, it can be directly placed on the other element, or intervening layer(s) may also be present. It will be understood that, although the terms "first", "second", "A", "B", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element or component discussed below could also be termed a "second" element or component, or vice versa, without departing from the scope of the present disclosure. When an element or layer is referred to as being "on," "connected to," or "coupled to" another element or layer, it may be directly on, connected to, or coupled to the other element or layer or intervening elements or layers may be present. However, when an element or layer is referred to as being "directly on," "directly connected to," or "directly coupled to" another element or layer, there are no intervening elements or layers present.

As used herein, unless stated otherwise, the term "substituted" means that a hydrogen atom of a functional group is replaced. Here, the hydrogen atom includes light hydrogen, deuterium, and tritium.

Herein, a substituent replacing the hydrogen atom may be any one selected from the group consisting of an unsubstituted or halogen-substituted $C_1$ to $C_{20}$ alkyl group (preferably $C_1$ to $C_6$ alkyl group), an unsubstituted or halogen-substituted $C_1$ to $C_{20}$ alkoxy group (preferably $C_1$ to $C_6$ alkoxy group), halogen, a cyano group, a carboxyl group, a carbonyl group, an amine group, a $C_1$ to $C_{20}$ alkylamine group (preferably $C_1$ to $C_6$ alkylamine group), a nitro group, a hydrazyl group, a sulfonic acid group, a $C_1$ to $C_{20}$ alkylsilyl group (preferably $C_1$ to $C_6$ alkylsilyl group), a $C_1$ to $C_{20}$ alkoxysilyl group (preferably $C_1$ to $C_6$ alkoxysilyl group), a $C_3$ to $C_{30}$ cycloalkylsilyl group (preferably $C_3$ to $C_7$ cycloalkylsilyl group), a $C_5$ to $C_{30}$ arylsilyl group (preferably $C_6$ to $C_{14}$ arylsilyl group), an unsubstituted or substituted $C_5$ to $C_{30}$ aryl group (preferably $C_6$ to $C_{14}$ aryl group), a $C_4$ to $C_{30}$ heteroaryl group (preferably $C_5$ to $C_{14}$ heteroaryl group), and combinations thereof, without being limited thereto.

As used herein, the term "halogen" or "halo" includes, without limitation, chlorine, bromine and iodine.

As used herein, unless stated otherwise, the term "hetero" in the terms "heteroaromatic ring", "heterocycloalkylene group", "heteroarylene group", "heteroarylalkylene group", "heterooxyarylene group", "heterocycloalkyl group", "heteroaryl group", "heteroarylalkyl group", "heterooxyaryl group", "heteroarylamine group", and the like means that at least one (for example, 1 to 5) of carbon atoms constituting an aromatic or alicyclic ring is substituted with at least one hetero atom selected from the group consisting of N, O, S, and combinations thereof.

As used herein, in definition of the substituent, the term "combinations thereof" means that two or more substituents are bonded to one another via a linking group or that two or more substituents are condensed with one another.

The present disclosure relates to an organic compound in which an aryl group is connected to a phenanthroline moiety substituted with at least one aromatic ring via at least one linker. The organic compound according to the present disclosure may be represented by Formula 1.

In accordance with one aspect of the present disclosure, there is provided an organic compound represented by Formula 1:

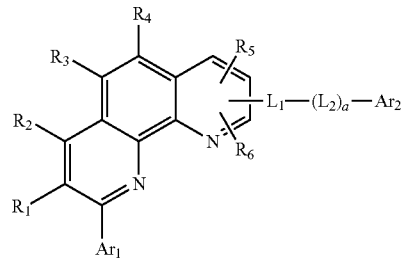

wherein $R_1$, $R_2$, $R_3$, $R_4$, $R_5$, and $R_6$ are each independently hydrogen, deuterium, tritium, an unsubstituted or substituted $C_1$ to $C_{20}$ alkyl group, an unsubstituted or substituted $C_1$ to $C_{20}$ alkoxy group, an unsubstituted or substituted $C_5$ to $C_{60}$ aryl group, or an unsubstituted or substituted $C_4$ to $C_{60}$ heteroaryl group;

$L_1$ and $L_2$ each independently have one of the following formulae:

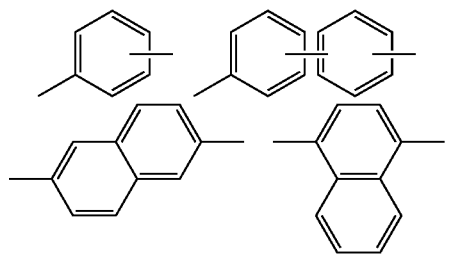

-continued

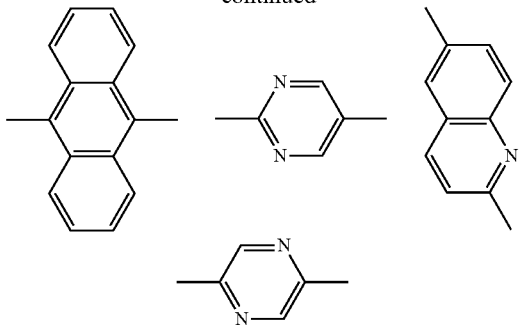

a is 0 or 1; and $Ar_1$ and $Ar_2$ are each independently an unsubstituted or substituted $C_5$ to $C_{60}$ aryl group or an unsubstituted or substituted $C_4$ to $C_{30}$ heteroaryl group.

In the compound represented by Formula 1, when a is 1, $L_1$ together with $L_2$ are represented by any one of the following formulae:

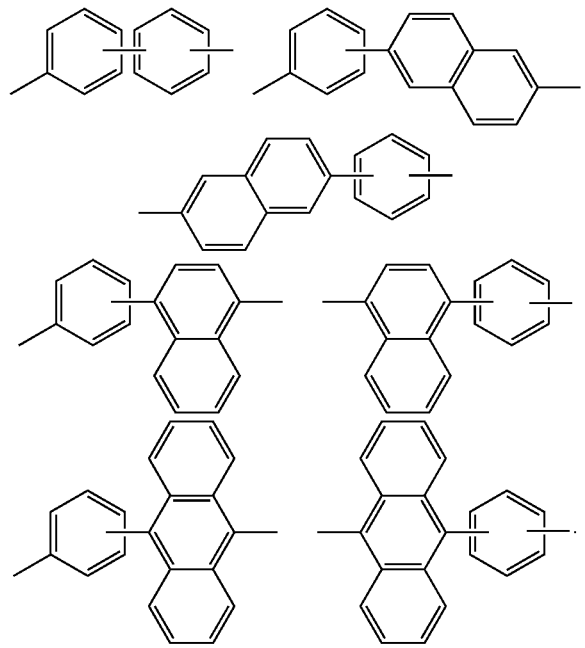

A core formed by introducing $Ar_1$ into phenanthroline as in Formula 1 has good thermal/electrical stability while exhibiting improved electron transfer/charge injection properties.

As shown in Formula 1, the organic compound contains a phenanthroline moiety. The phenanthroline moiety improves electron transfer properties while preventing an alkali metal or an alkaline earth metal in an N-type charge generation layer from diffusing into a P-type charge generation layer. In addition, the phenanthroline moiety is substituted with at least one aromatic ring, such as an aryl group or a heteroaryl group ($Ar_1$). Thus, the organic compound has improved electron transfer properties while exhibiting improved thermal stability.

In one embodiment, $R_1$, $R_2$, $R_3$, $R_4$, $R_5$, and $R_6$ may be each independently hydrogen, deuterium, tritium, a $C_1$ to $C_{20}$ alkyl group, or a $C_1$ to $C_{20}$ alkoxy group.

In Formula 1, $Ar_1$ and $Ar_2$ are each independently a substituted or unsubstituted aryl group or a substituted or unsubstituted heteroaryl group. In one embodiment, $Ar_1$ and $Ar_2$ may include an unsubstituted or substituted aromatic ring. For example, $Ar_1$ and $Ar_2$ may be each independently an unfused or fused homoaryl group such as unsubstituted or substituted phenyl, biphenyl, terphenyl, naphthyl, anthracenyl, pentalenyl, indenyl, indenoindenyl, heptalenyl, biphenylenyl, indacenyl, phenalenyl, phenanthrenyl, benzophenanthrenyl, dibenzophenanthrenyl, azulenyl, pyrenyl, fluoranthenyl, triphenylenyl, chrysenyl, tetraphenyl, tetracenyl, pleiadenyl, pentaphenyl, pentacenyl, fluorenyl, indenofluorenyl, diazafluorenyl, and spiro-fluorenyl groups; and/or an unfused or fused heteroaryl group such as pyrrolyl, pyridinyl, terpyridinyl, phenylterpyridinyl, pyrimidinyl, pyrazinyl, pyridazinyl, triazinyl, tetrazenyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothiocarbazolyl, quinolinyl, isoquinolinyl, phthalazinyl, quinoxalinyl, quinazolinyl, quinolizinyl, phthalazinyl, benzoquinolinyl, benzoisoquinolinyl, benzoquinazolinyl, benzoquinoxalinyl, acridinyl, phenanthrolinyl, phenanthrenyl, perimidinyl, phenanthridinyl, pteridinyl, cinnolinyl, naphthyridinyl, furanyl, pyranyl, oxazinyl, oxazolyl, oxadiazolyl, triazolyl, dioxinyl, benzofuranyl, dibenzofuranyl, arylthiazolyl, thiopyranyl, xanthenyl, chromanyl, isochromanyl, thiazinyl, thiophenyl, benzothiophenyl, dibenzothiophenyl, carbolinyl, difuropyrazinyl, benzofurodibenzofuranyl, benzothiodibenzofuranyl, and N-substituted spirofluorenyl groups.

More specifically, $Ar_1$ and $Ar_2$ may be each independently selected from phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyanopyridyl, alkoxypyridyl, silylpyridyl, phenylpyridyl, pyrimidyl, halopyrimidyl, cyanopyridimyl, alkoxy pyrimidyl, phenyl pyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazolyl, imidazolyl, carbolinyl, phenanthrenyl, terphenyl, terpyridinyl, phenylterpyridinyl, triphenylenyl, fluoranthenyl, and diazafluorenyl groups.

In the above groups, the alkyl or alkoxy refers to an alkyl or alkoxy group having 1 to 20 (preferably 1 to 6) carbon atoms, and the aryl refers to an aryl having 5 to 30 (preferably 6 to 14) carbon atoms.

In one embodiment, $Ar_1$ is a homoaryl group such as a substituted or unsubstituted phenyl group, biphenyl group, or naphthyl group, and $Ar_2$ is a homoaryl group such as a substituted or unsubstituted phenyl group, naphthyl group, anthracenyl group, phenalenyl group, phenanthrenyl group, pyrenyl group, triphenylenyl group, chrysenyl group, fluoranthenyl group, fluorenyl group, diphenylfluorenyl group, or spiro-fluorenyl group, or a heteroaryl group such as a substituted or unsubstituted pyridyl group, pyrazinyl group, pyrimidyl group, pyridazinyl group, triazinyl group, quinolinyl group, isoquinolinyl group, phthalazinyl group, quinoxalinyl group, cinnolinyl group, quinazolinyl group, quinolizinyl group, or carbazolyl group. When $Ar_2$ is a heteroaryl group, $Ar_2$ may contain one or two aromatic rings. However, it should be understood that the present disclosure is not limited thereto.

The organic compound represented by Formula 1 is an organic material that has good thermal stability while exhibiting good charge generation/injection properties. Thus, when used as a material for an N-type charge generation layer (n-CGL) in a tandem organic light emitting diode, the organic compound represented by Formula 1 can reduce driving voltage of the organic light emitting diode while improving efficiency and lifespan of the organic light emitting diode.

As described above, the organic compound represented by Formula 1 contains a phenanthroline moiety substituted with at least one aromatic ring. Since the organic compound has a high decomposition temperature or glass transition temperature and thus good thermal stability due to the presence of the phenanthroline moiety, the organic compound can be prevented from being deteriorated or degraded by Joule's heat generated upon operation of a device. Accordingly, when used in an organic light emitting diode, the organic compound can improve lifespan of the organic light emitting diode while reducing driving voltage of the organic light emitting diode.

In addition, since the phenanthroline moiety of the organic compound represented by Formula 1 has a nitrogen atom having an $sp^2$ hybrid orbital, which is relatively rich in electrons, the organic compound has good electron transport properties. Thus, the organic compound can efficiently supply electrons to a light emitting material layer when used as a material for electron transport layers. In particular, the phenanthroline moiety has two electron-rich nitrogen atoms and is thus combined with an alkali metal or alkali earth metal compound, which is a dopant of an N-type charge generation layer, to form a gap state. As a result, a difference in energy level between the N-type charge generation layer and a P-type charge generation layer is reduced, such that electron injection into the N-type charge generation layer can be facilitated while electron transfer from the N-type charge generation layer to an adjacent electron transport layer can be maximized.

In addition, the organic compound having nitrogen atoms is combined with the alkali metal or alkali earth metal compound in the N-type charge generation layer, thereby preventing the alkali metal or alkali earth metal compound from diffusing into the P-type charge generation layer. As a result, reduction in lifespan of the organic light emitting diode can be prevented.

The organic compound represented by Formula 1 has a relatively high electron affinity (EA), as compared with a compound having phenanthroline not substituted with $Ar_1$, and thus can efficiently react with the alkali metal or alkali earth metal compound. In addition, since the organic compound has a reduced electron reorganization energy ($\lambda$electron) and an increased electron/hole rate constant ratio (ket(e)/ket(h)), the organic compound can improve stability of anions that accept electrons, thereby exhibiting good properties in terms of transmission of electrons from the P-type charge generation layer (p-CGL) to the electron transport layer (ETL).

In one embodiment, the organic compound represented by Formula 1 may be a compound having $L_1$ and $L_2$ substituted at o- and m-positions. As compared with a compound having $L_1$ and $L_2$ substituted at the p-position, such an organic compound allows relatively smooth interaction between phenanthroline and lithium due to intramolecular twisting, thereby facilitating formation of a gap state, whereby an energy barrier between the electron transport layer (ETL) and the N-type charge generation layer (n-CGL) can be reduced while electron injection/transfer properties can be improved, thereby reducing driving voltage of the organic light emitting diode.

In manufacture of an OLED, the organic compound represented by Formula 1 is subjected to deposition at high temperature for a long time. During the process, intramolecular bonds can be broken or disrupted due to a difference in thermal stability between molecules. When such an OLED in which materials having insufficient thermal/electrical stability are stacked one above another is driven for a long time, not only injection of electrons from an interface between a P-type charge generation layer (p-CGL) and a hole injection layer (HIL) into an N-type charge generation layer (n-CGL) but also injection/transfer of electrons from the N-type charge generation layer (n-CGL) into an electron transport layer (ETL) can be deteriorated, causing reduction in performance and lifespan of the OLED. In contrast, since the organic compound represented by Formula 1 has higher decomposition temperature or glass transition temperature and thus higher thermal stability than a compound having phenanthroline not substituted with $Ar_1$, the organic compound can be prevented from being deteriorated or degraded by Joule's heat generated upon operation of the OLED, thereby increasing lifespan of the OLED.

In one embodiment, the organic compound represented by Formula 1 may be any one of compounds EN-m001 to EN-m142:

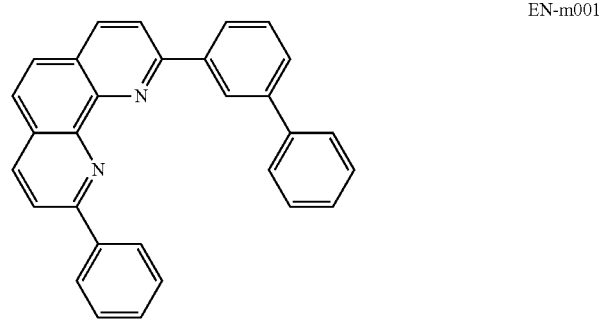

EN-m001

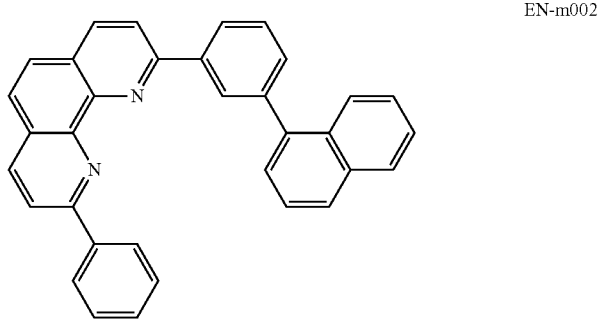

EN-m002

-continued
EN-m003
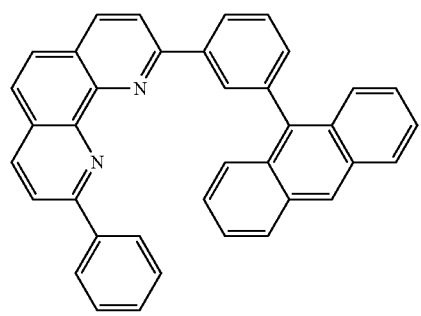
EN-m004
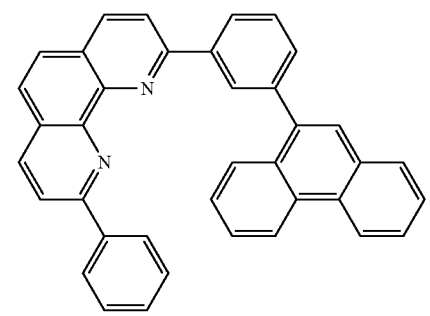
EN-m005
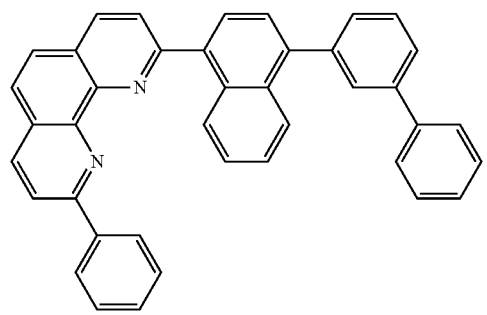
EN-m006
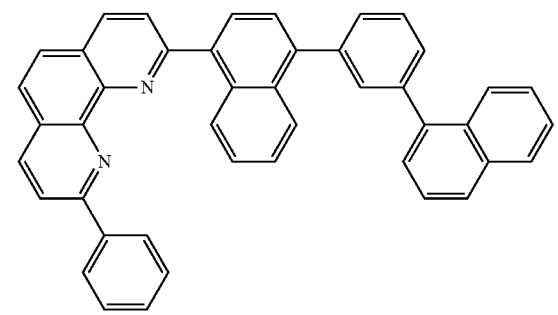
EN-m007
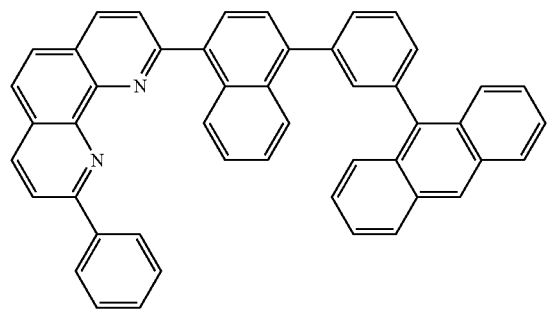
EN-m008
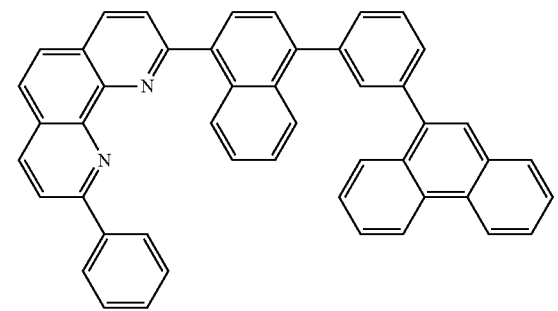
EN-m009
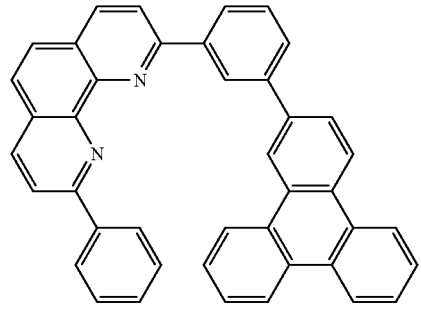
EN-m010
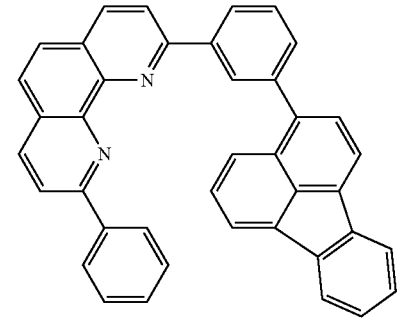
EN-m011
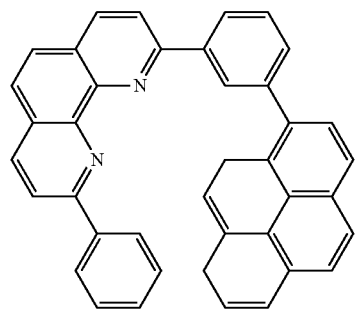
EN-m012
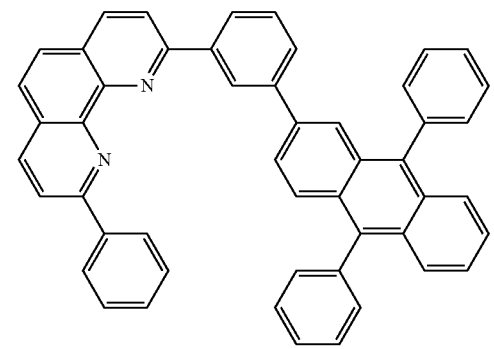

-continued
EN-m013
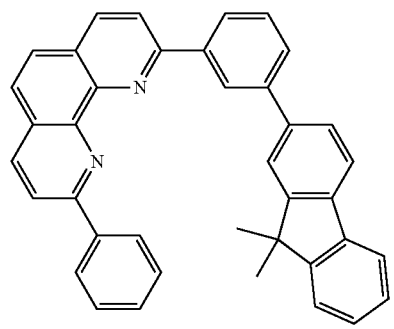
EN-m014
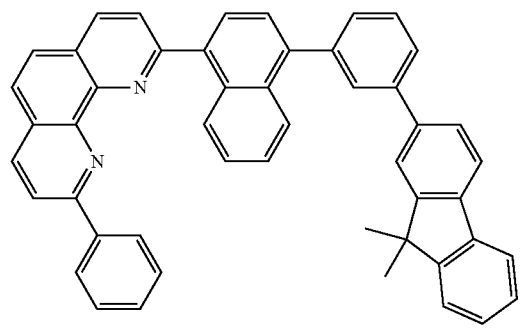
EN-m015
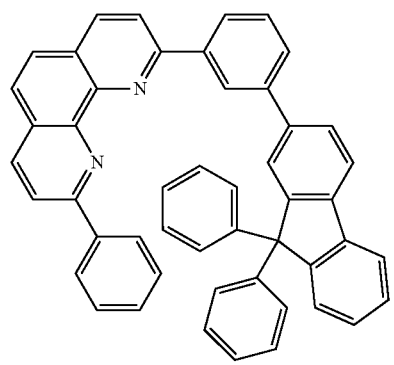
EN-m016
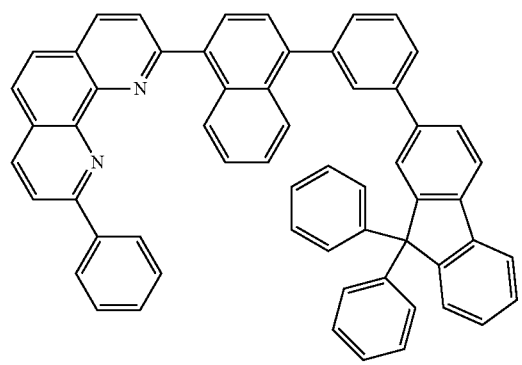
EN-m017
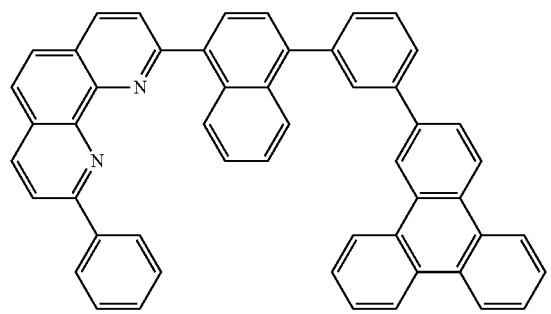
EN-m018
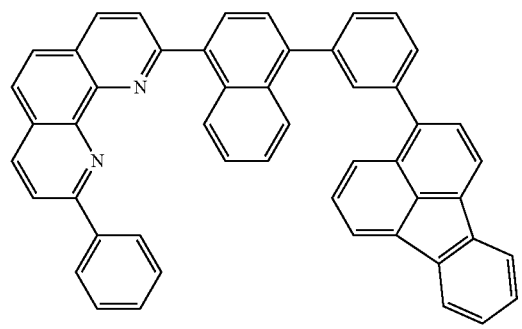
EN-m019
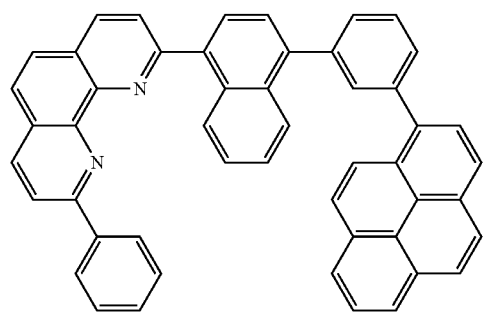
EN-m020
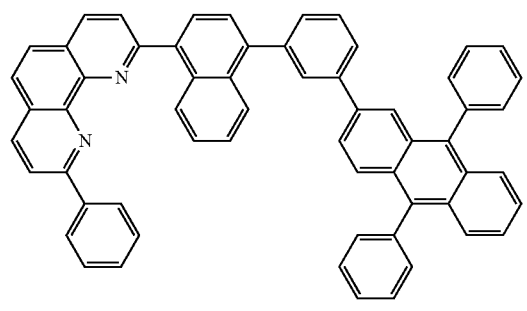

-continued
EN-m021
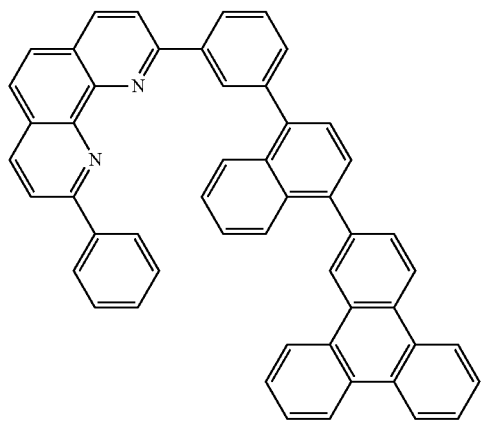
EN-m022
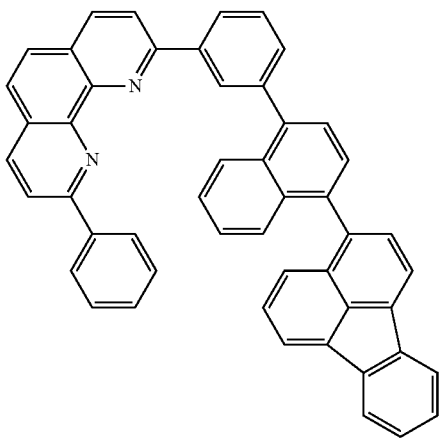
EN-m023
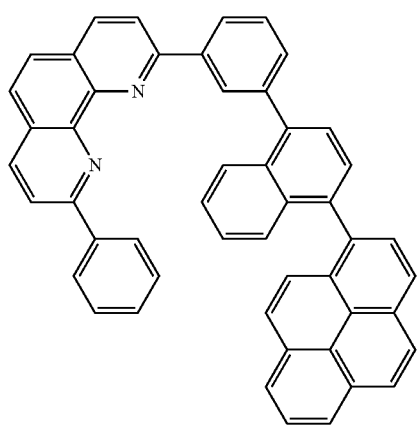
EN-m024
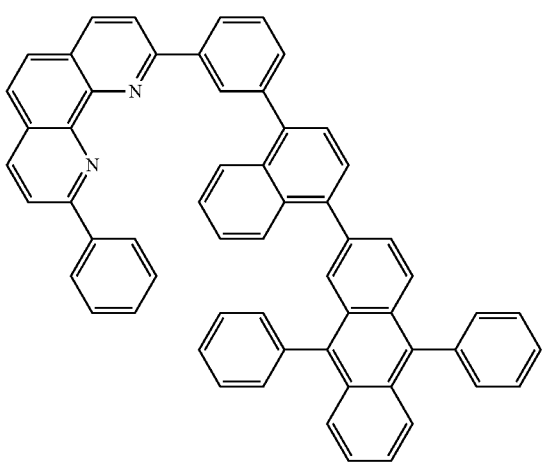
EN-m025
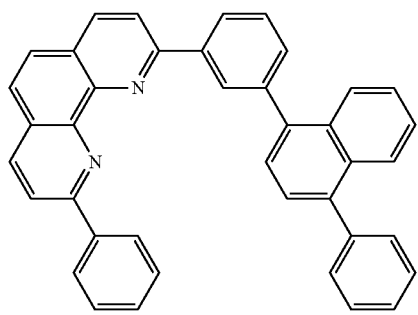
EN-m026
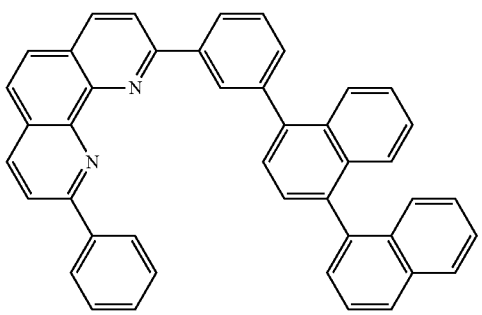
EN-m027
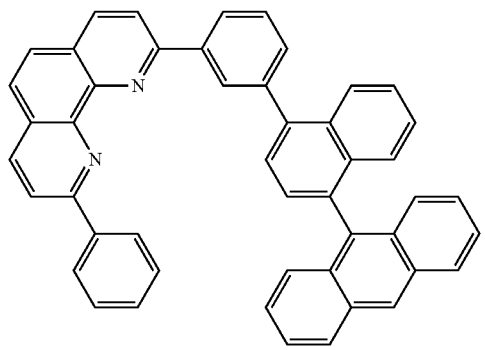
EN-m028
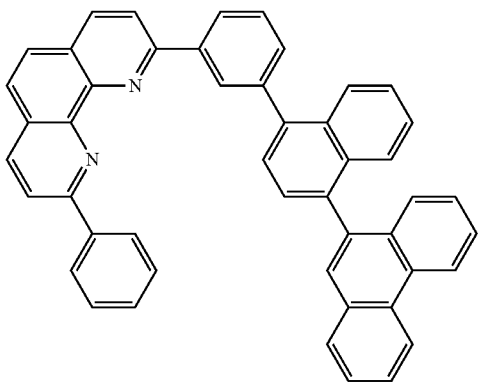

-continued
EN-m029
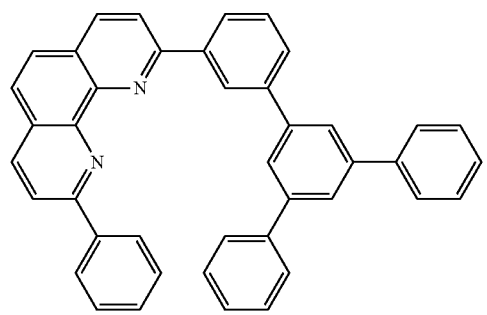
EN-m030
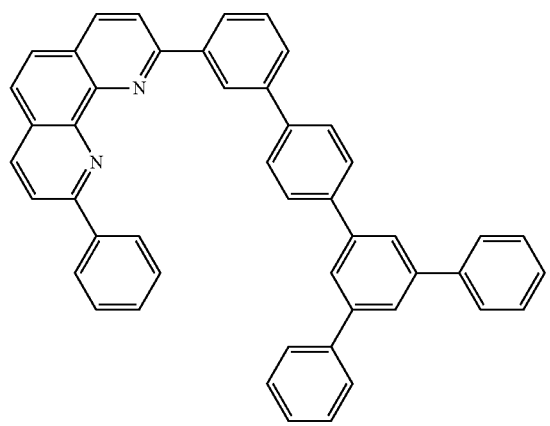
EN-m031
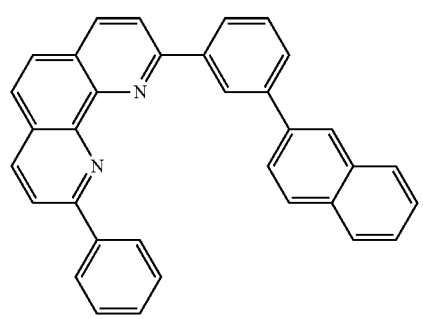
EN-m032
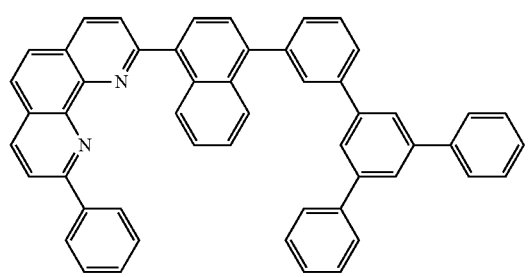
EN-m033
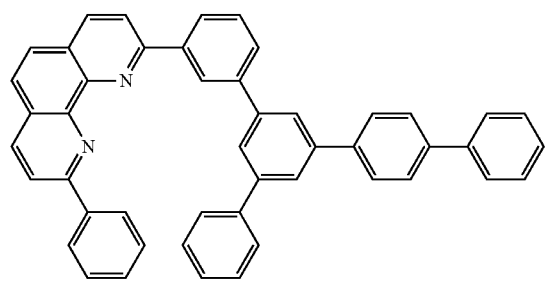
EN-m034
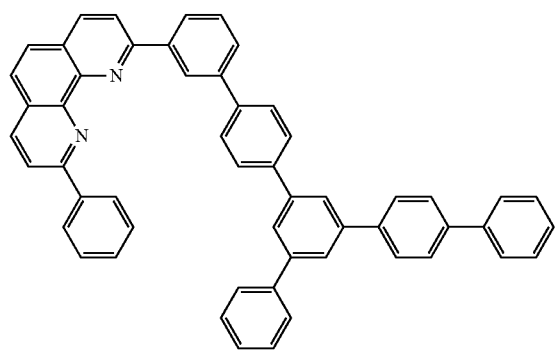
EN-m035
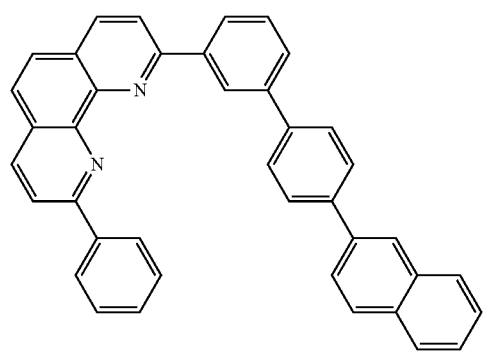
EN-m036
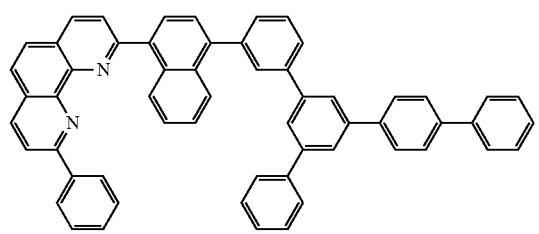

-continued
EN-m037
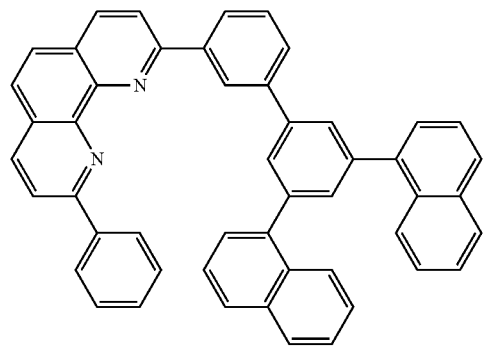
EN-m038
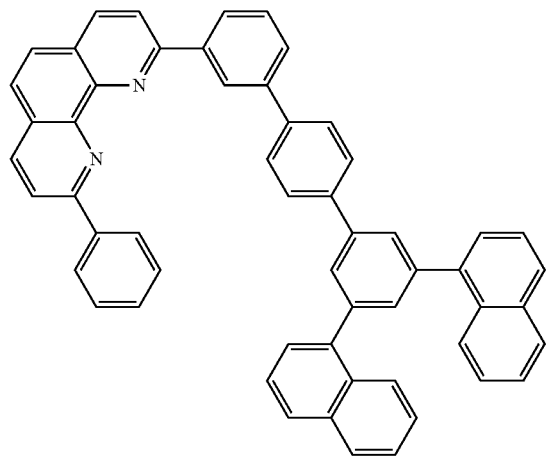
EN-m039
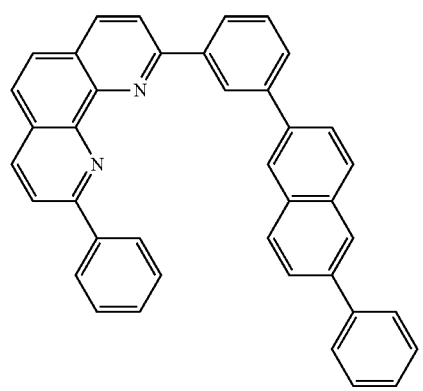
EN-m040
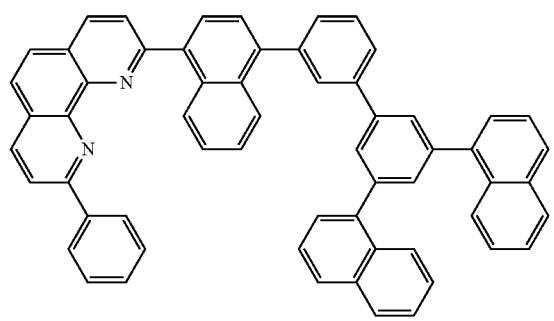
EN-m041
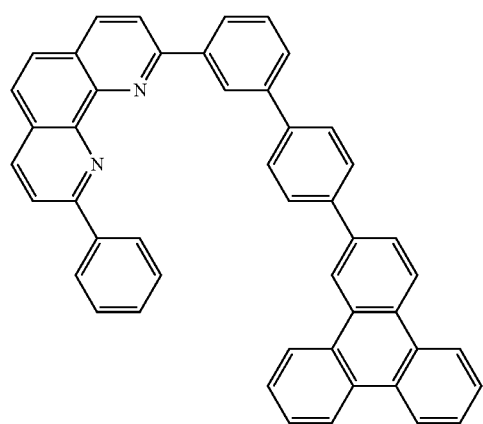
EN-m042
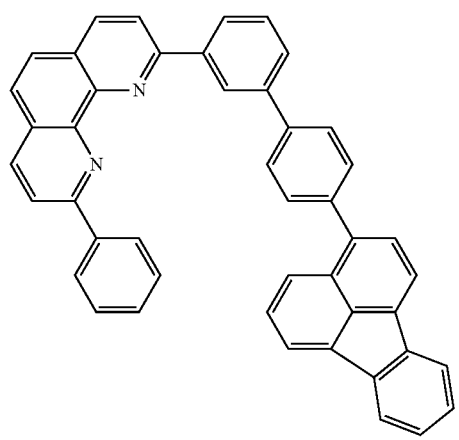

-continued
EN-m043
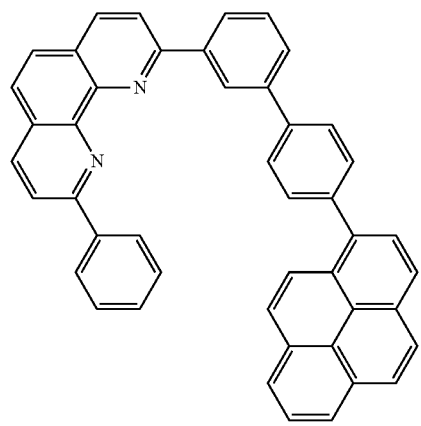
EN-m044
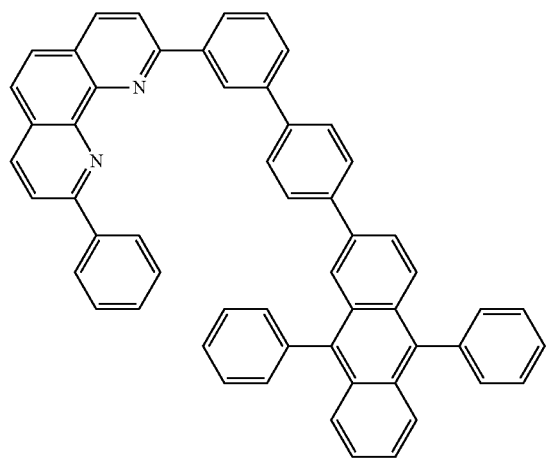
EN-m045
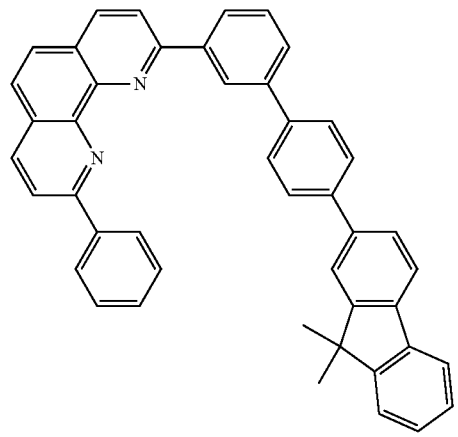
EN-m046
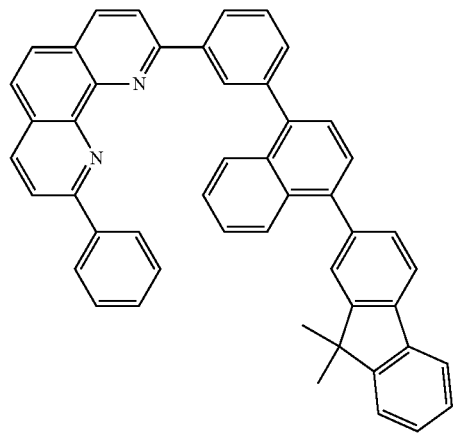
EN-m047
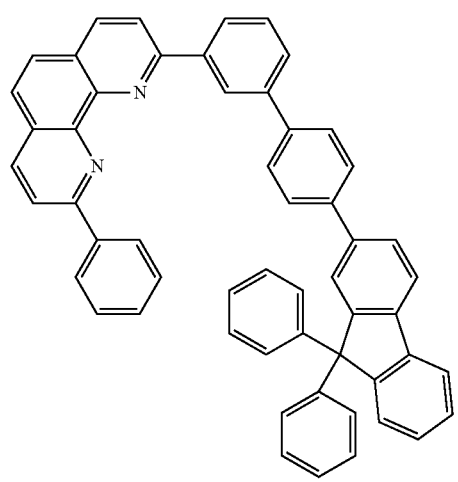
EN-m048
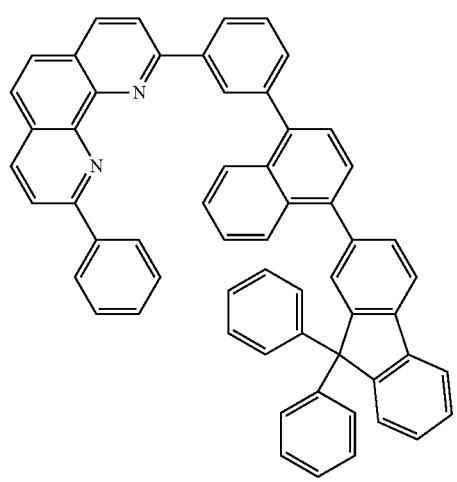

-continued
EN-m049
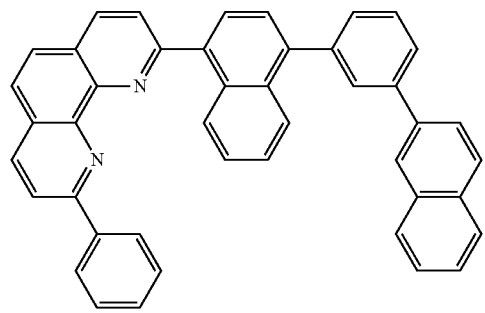
EN-m050
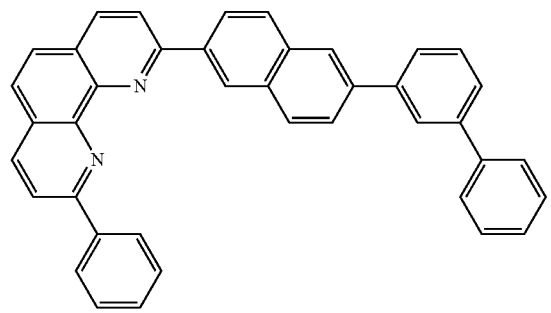
EN-m051
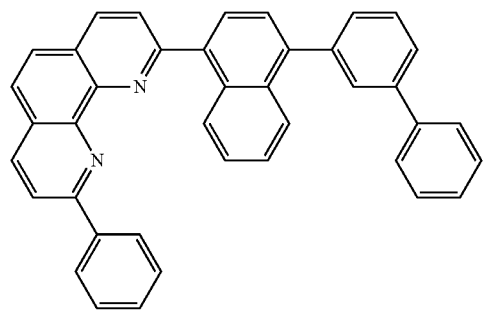
EN-m052
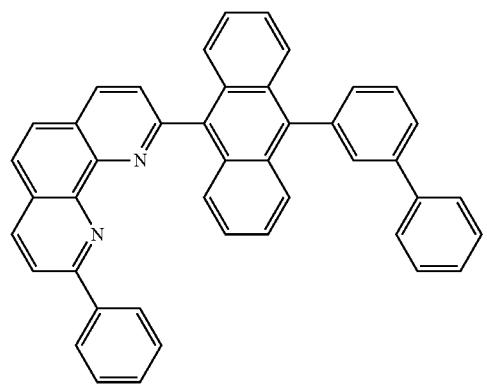
EN-m053
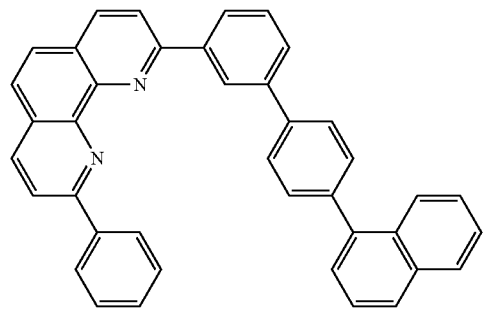
EN-m054
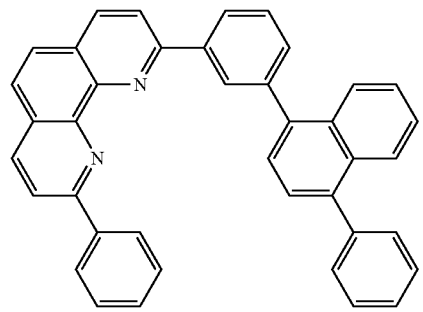
EN-m055
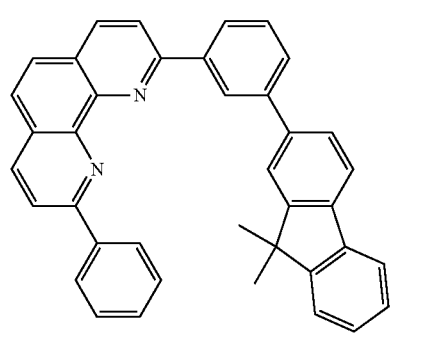
EN-m056
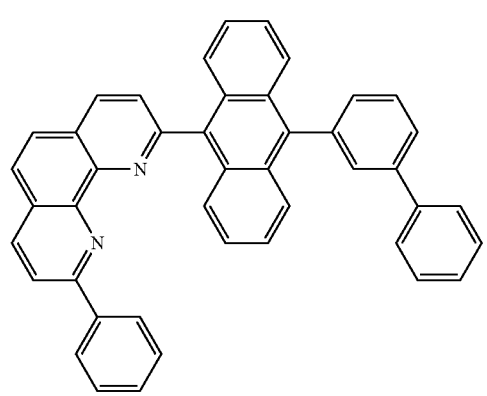

-continued
EN-m057
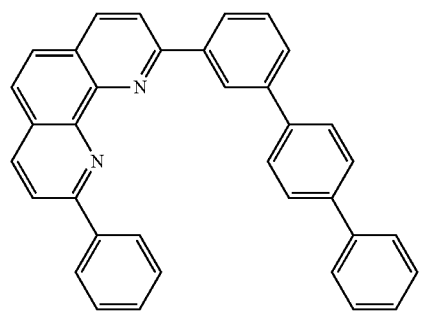
EN-m058
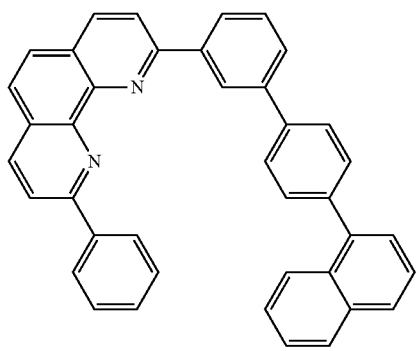
EN-m059
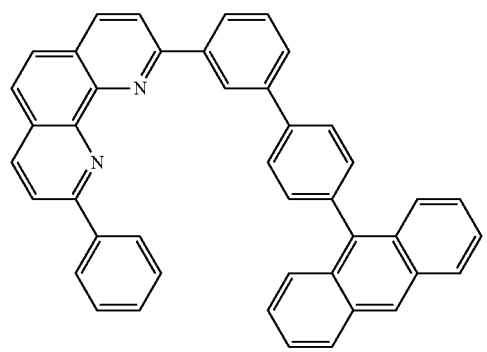
EN-m060
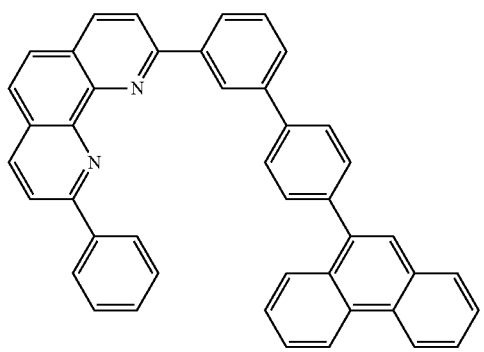
EN-m061
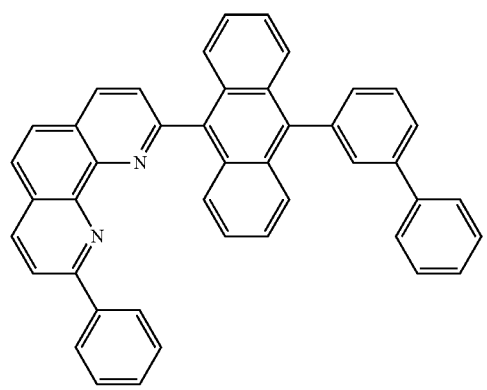
EN-m062
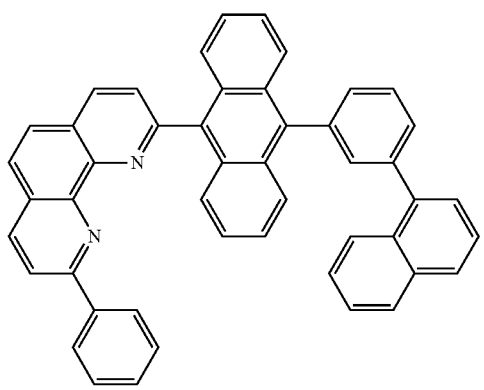
EN-m063
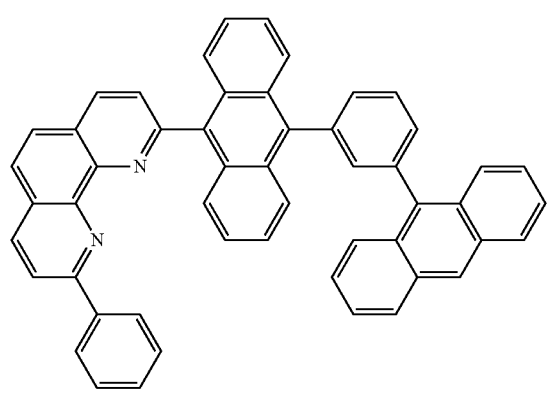
EN-m064
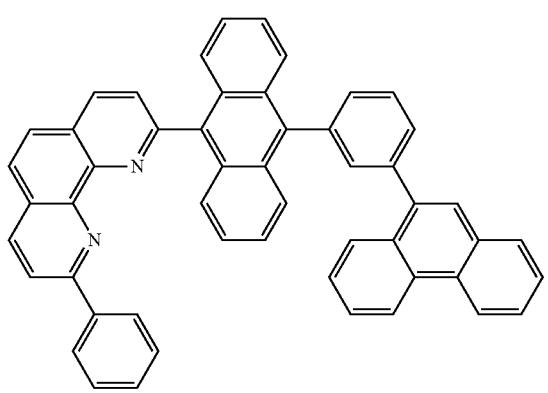

-continued
EN-m065
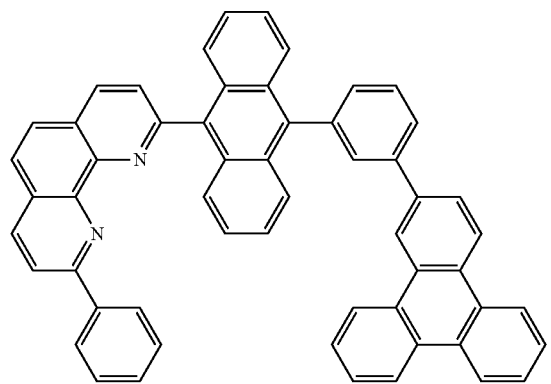
EN-m066
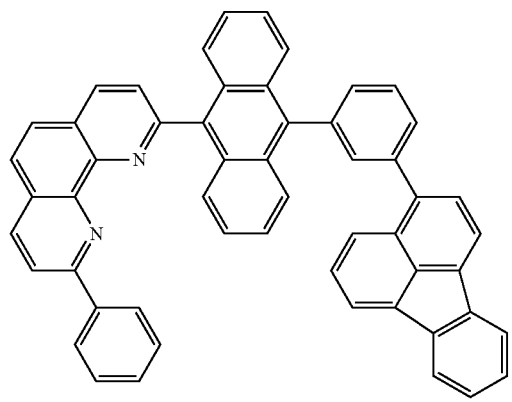
EN-m067
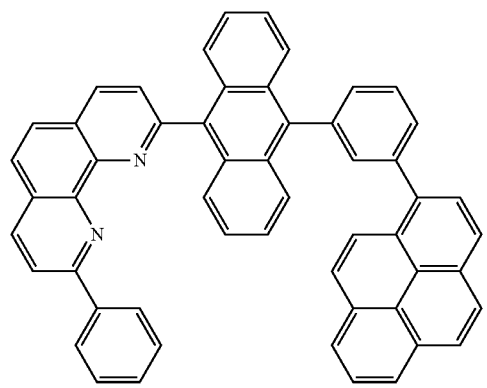
EN-m068
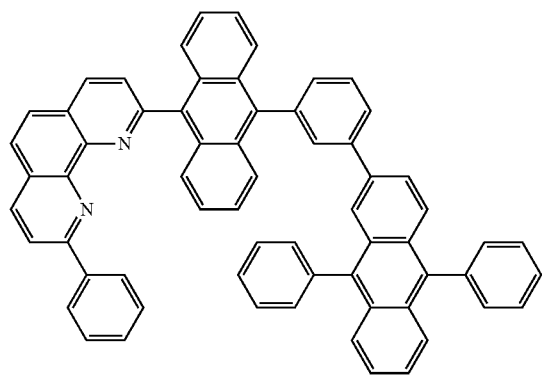
EN-m069
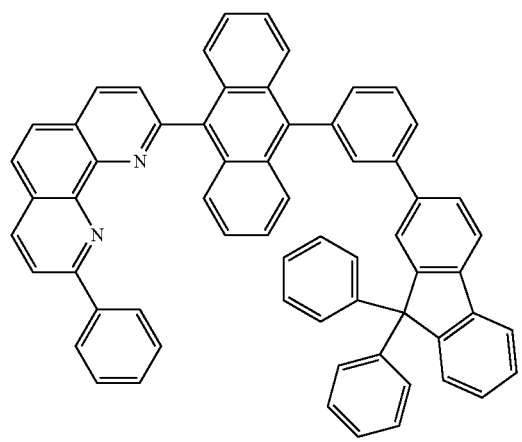
EN-m070
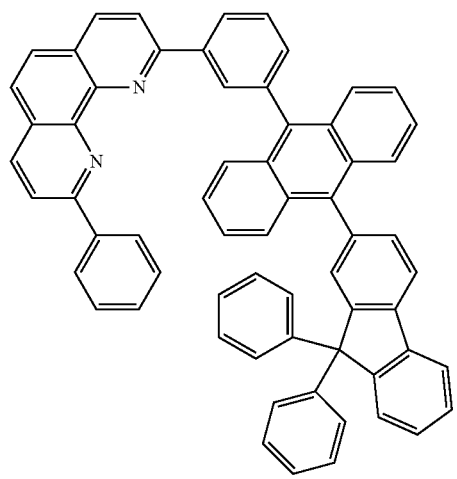

-continued
EN-m071
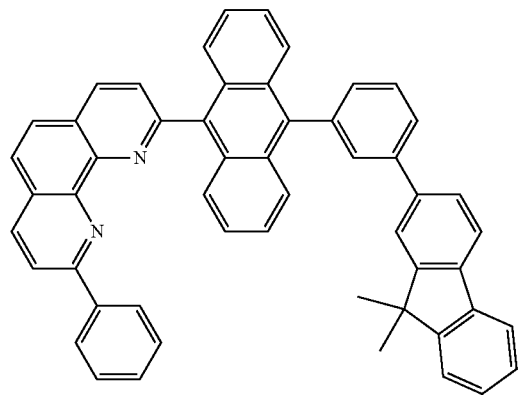
EN-m072
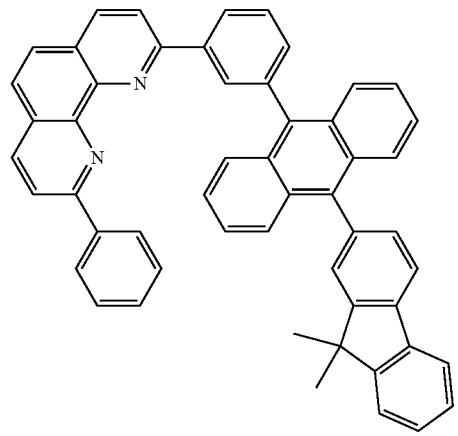
EN-m073
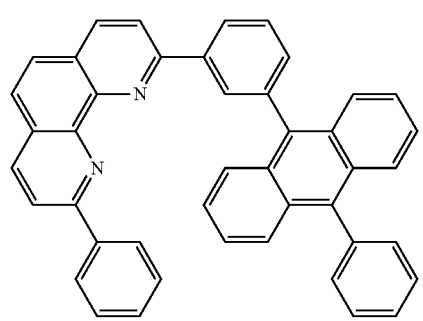
EN-m074
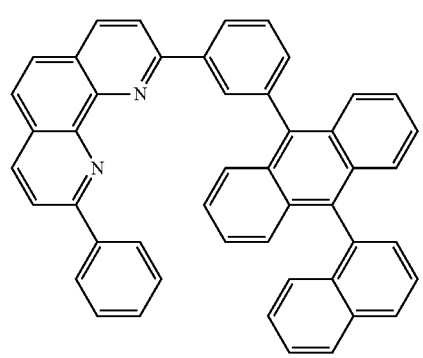
EN-m075
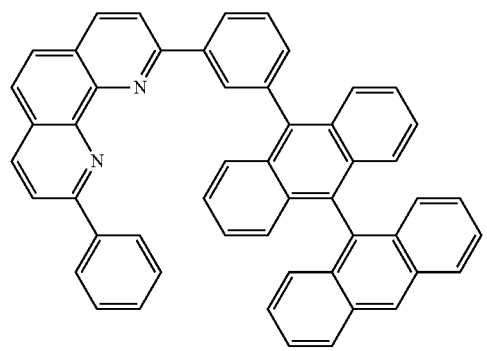
EN-m076
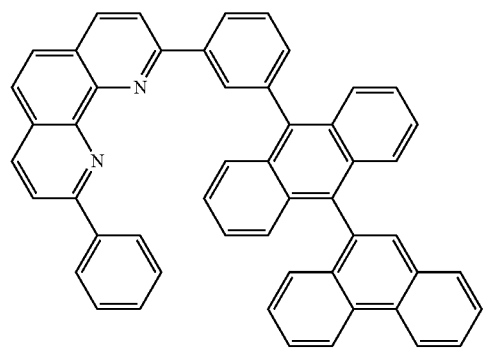
EN-m077
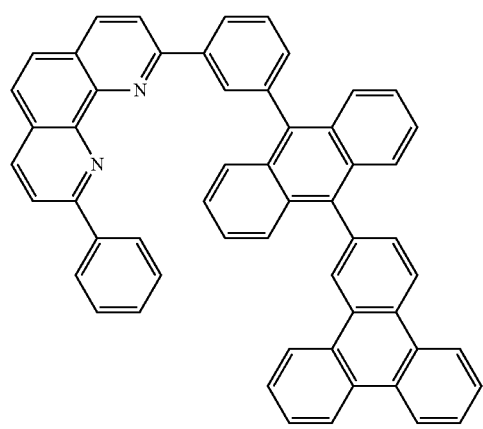
EN-m078
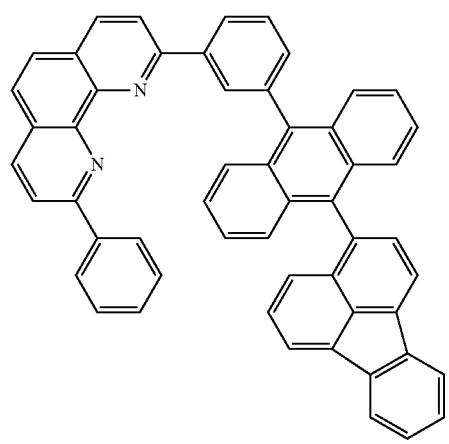

-continued
EN-m079
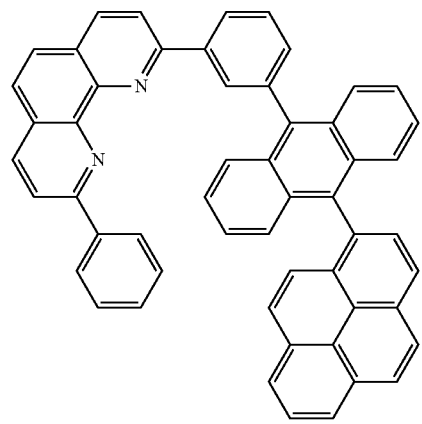
EN-m080
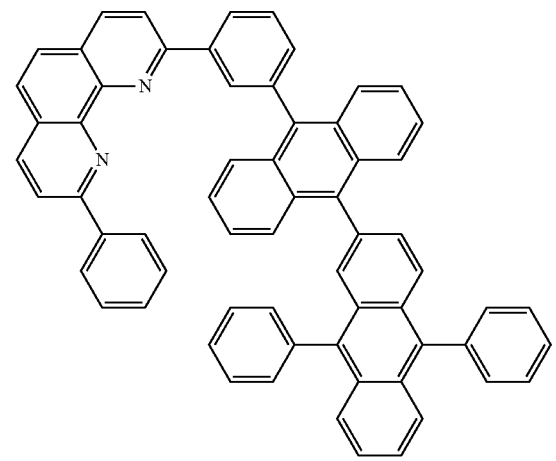
EN-m081
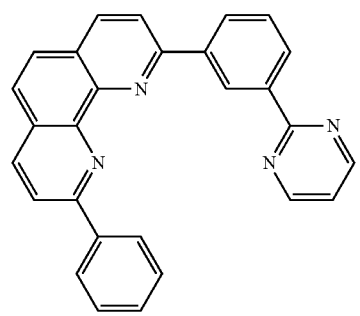
EN-m082
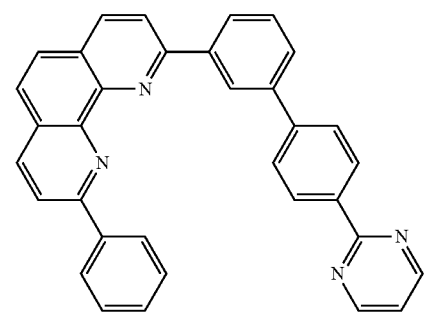
EN-m083
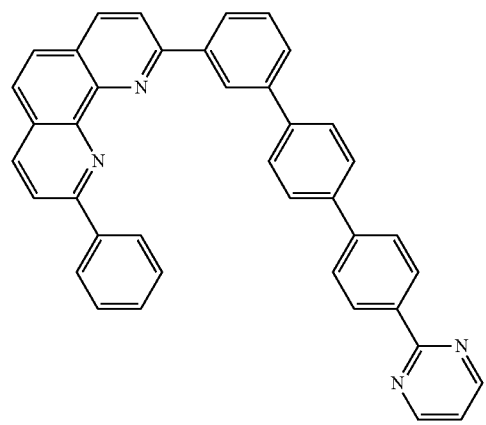
EN-m084
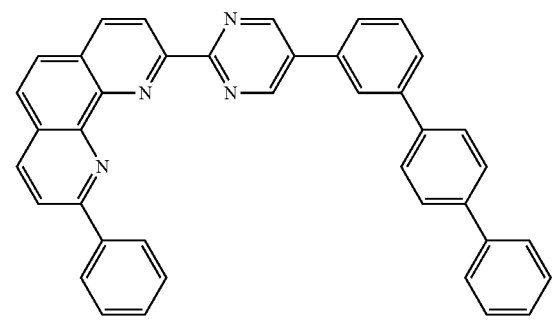
EN-m085
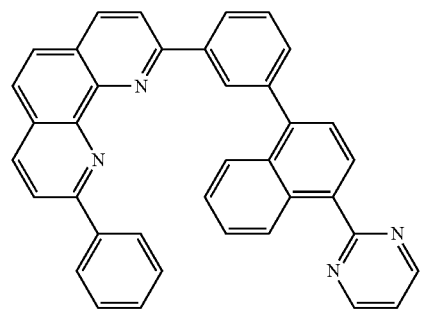
EN-m086
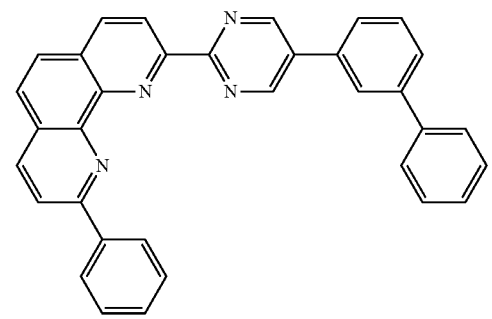

-continued
EN-m087
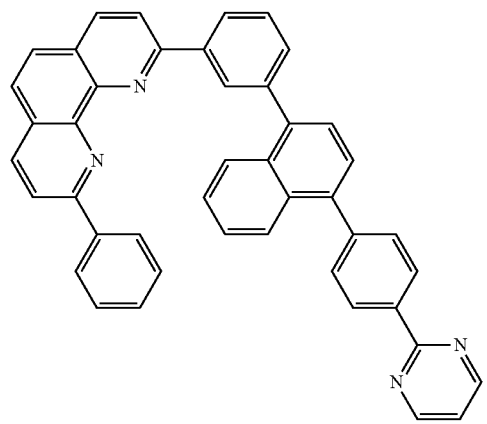
EN-m088
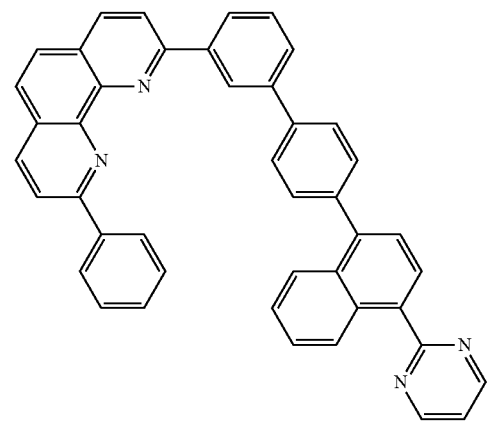
EN-m089
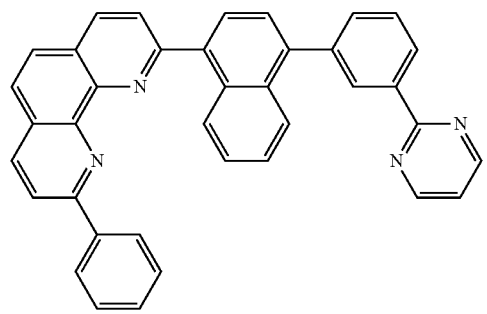
EN-m090
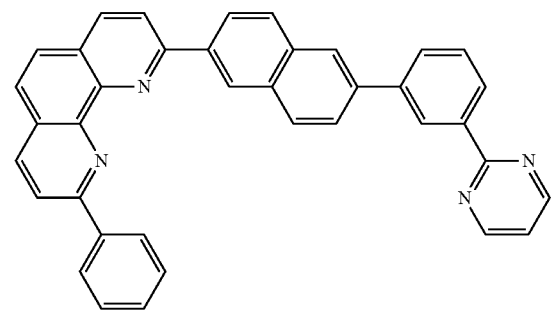
EN-m091
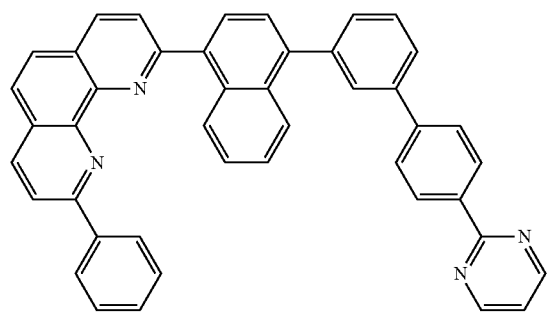
EN-m092
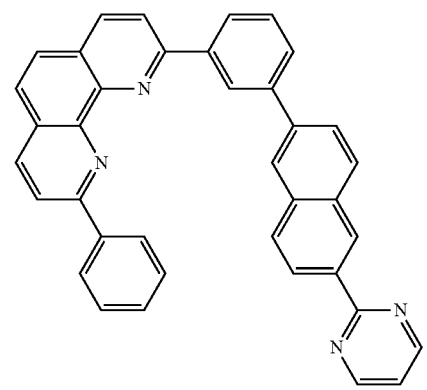
EN-m093
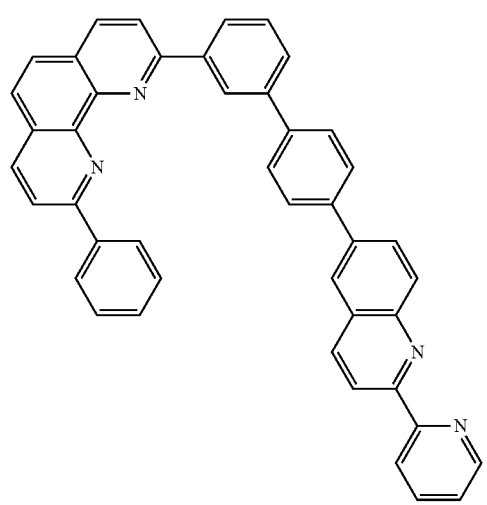
EN-m094
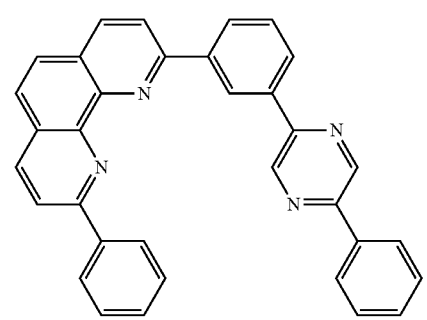

-continued
EN-m095
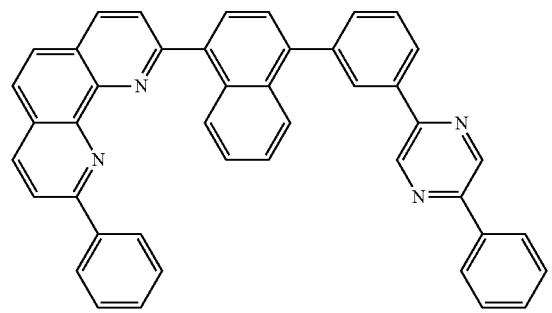
EN-m096
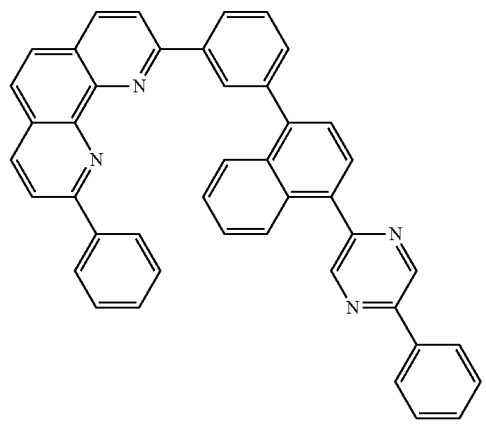
EN-m097
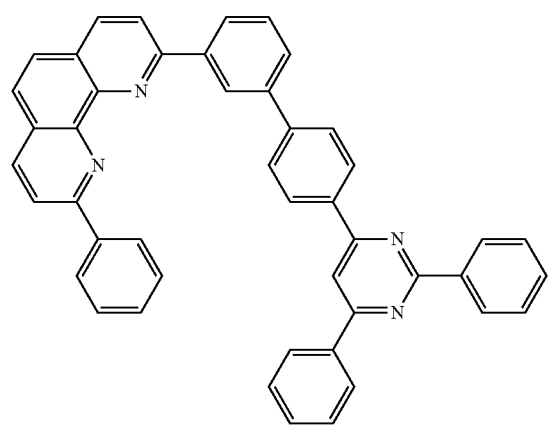
EN-m098
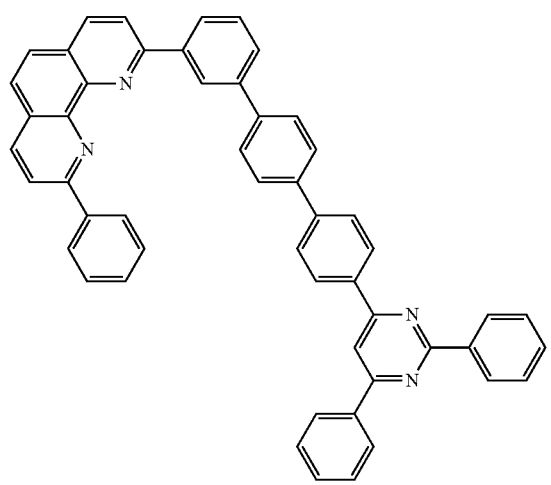
EN-m099
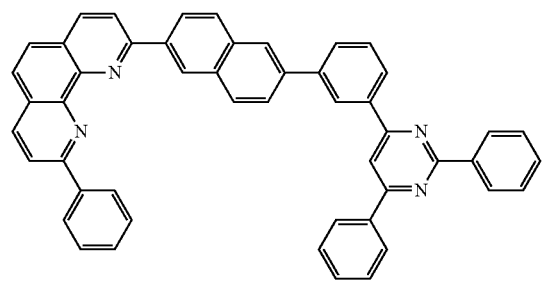
EN-m100
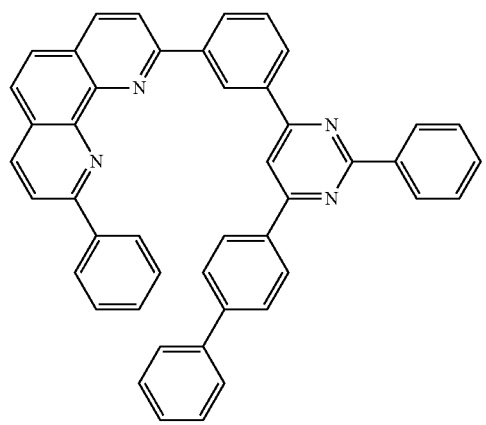

EN-m101
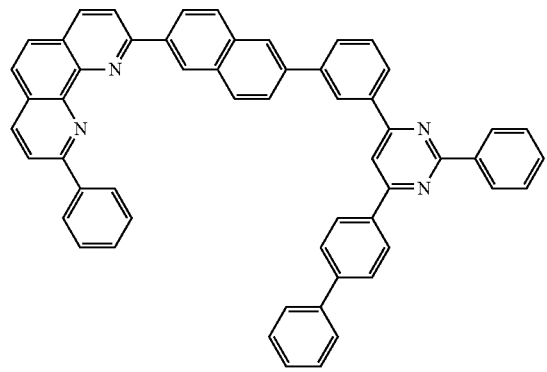
EN-m102
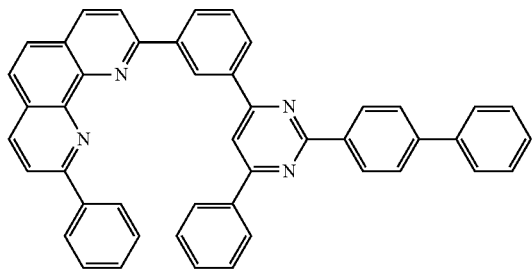
EN-m103
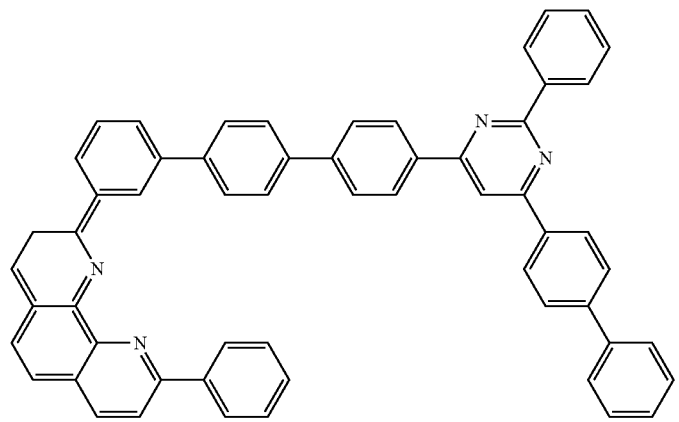
EN-m104
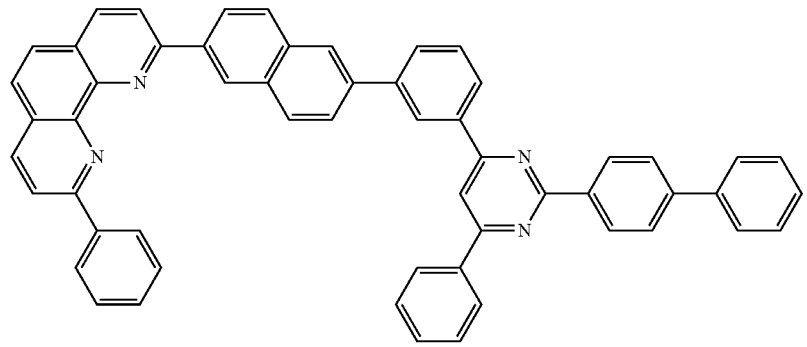
EN-m105
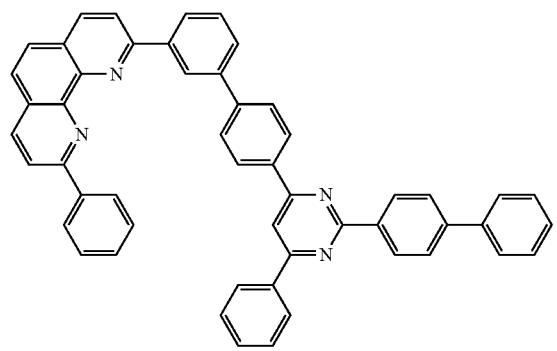
EN-m106
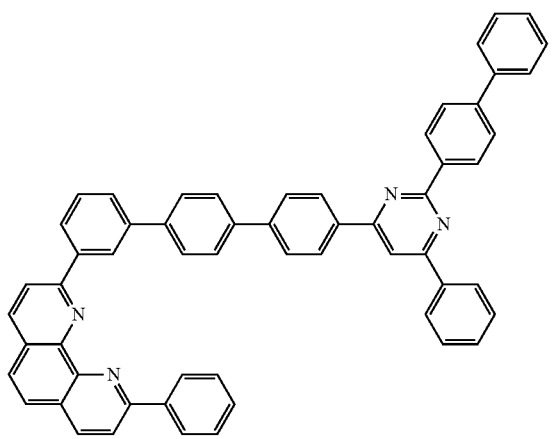

-continued
EN-m107
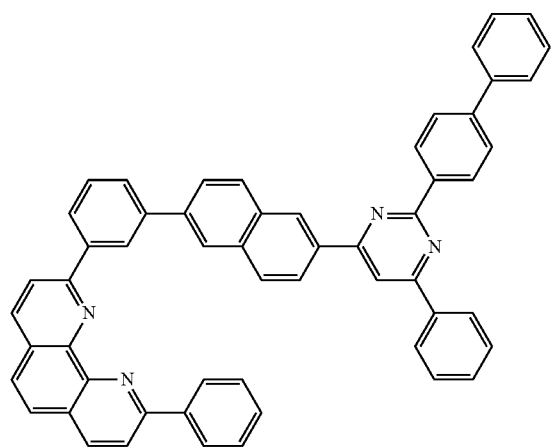
EN-m108
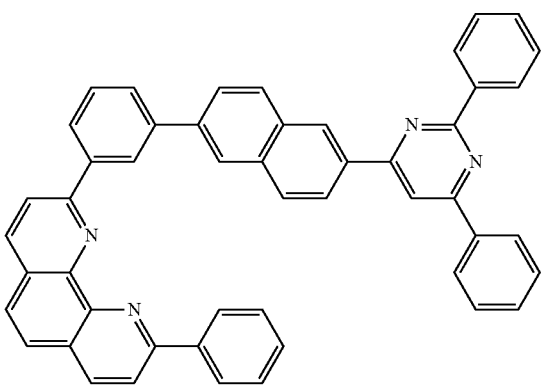
EN-m109
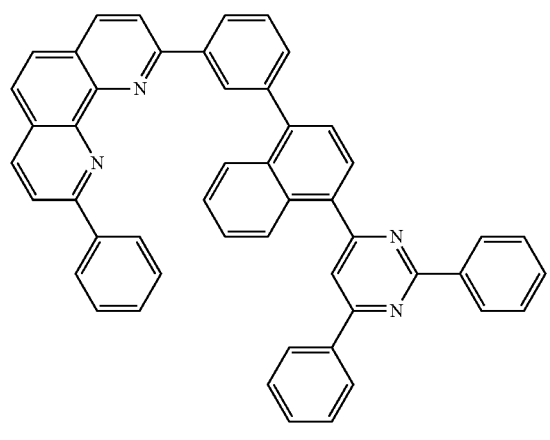
EN-m110
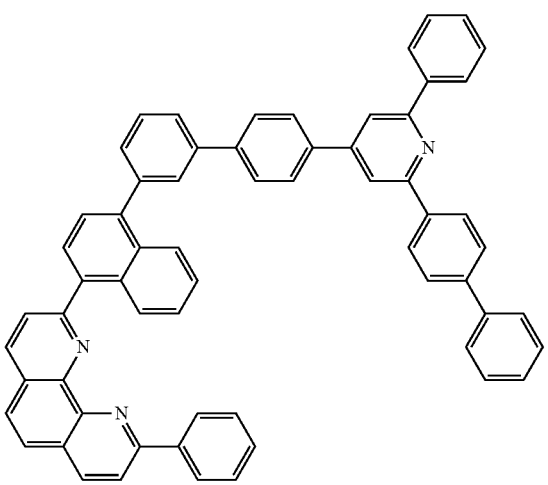
EN-m111
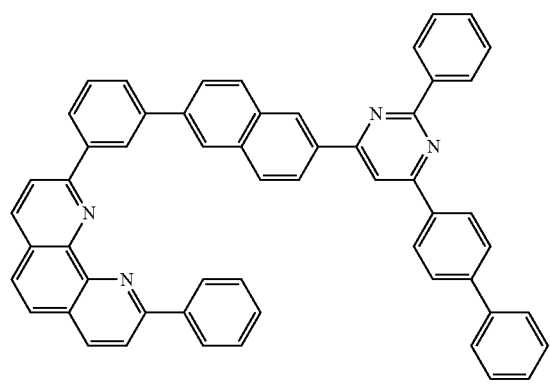
EN-m112
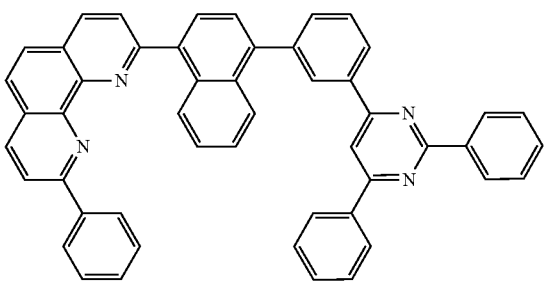

-continued
EN-m113
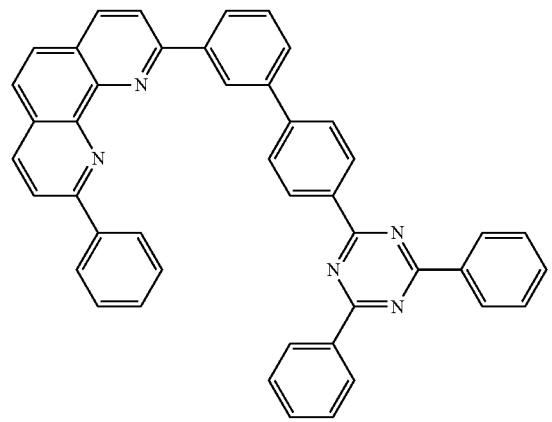
EN-m114
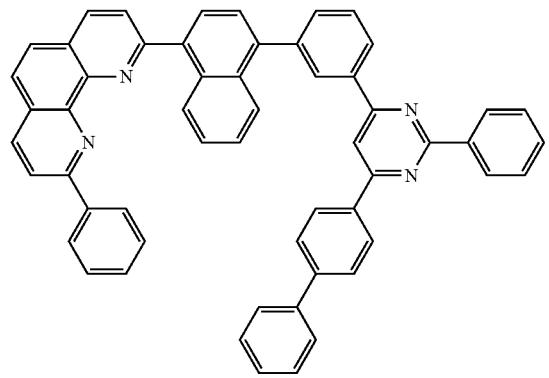
EN-m115
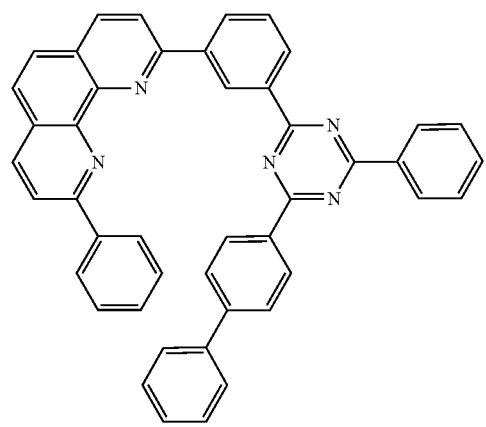
EN-m116
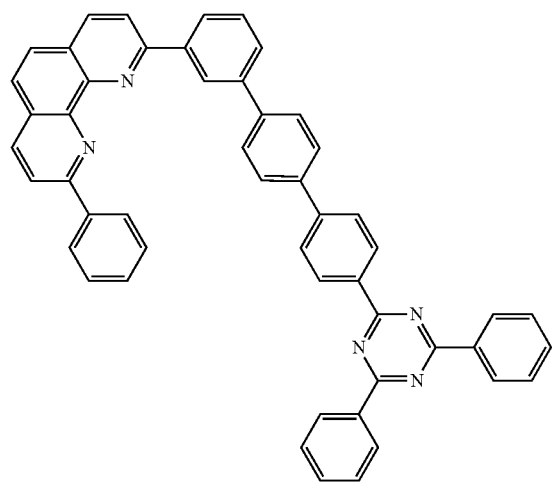
EN-m117
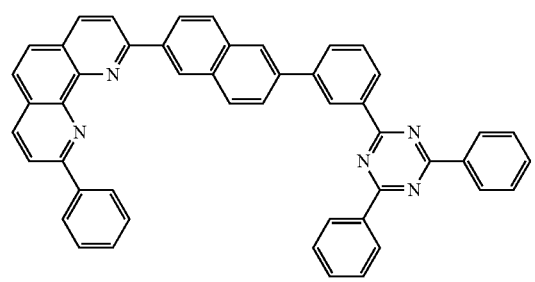
EN-m118
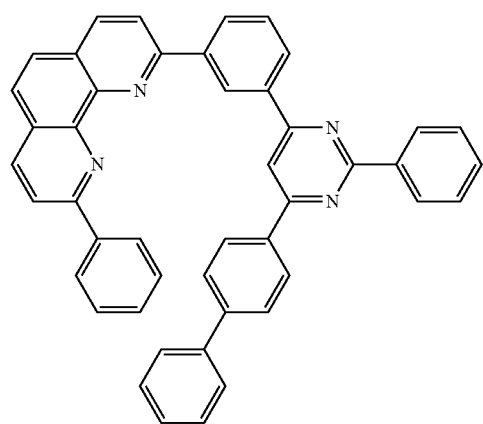

-continued
EN-m119
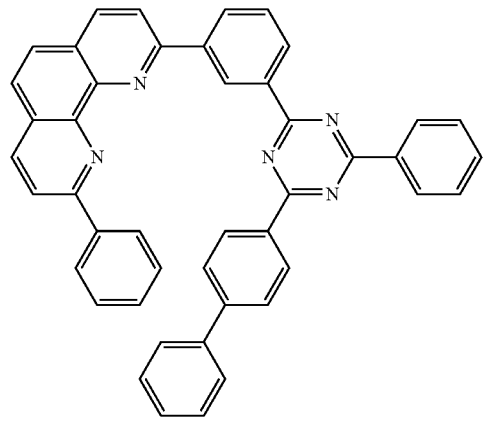
EN-m120
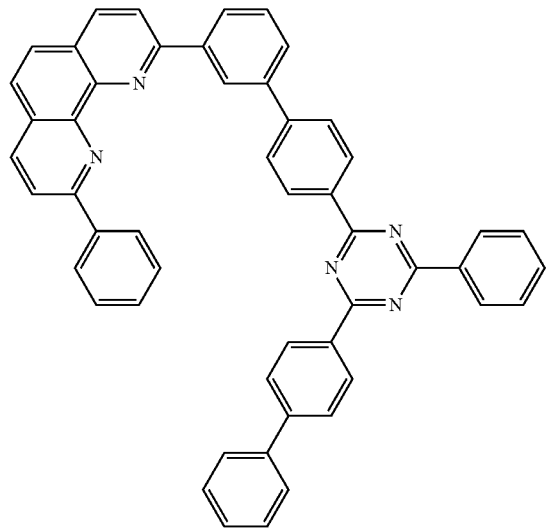
EN-m121
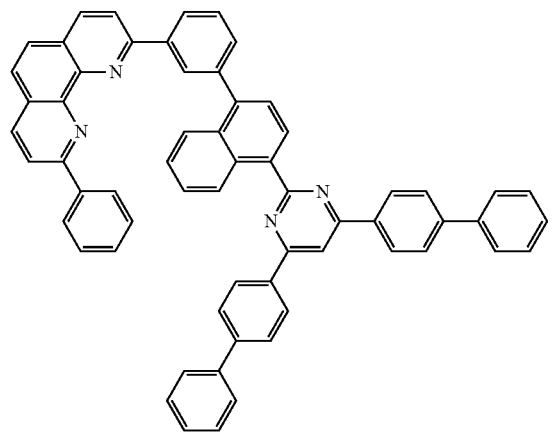
EN-m122
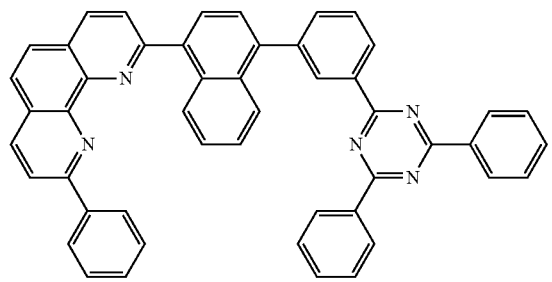
EN-m123
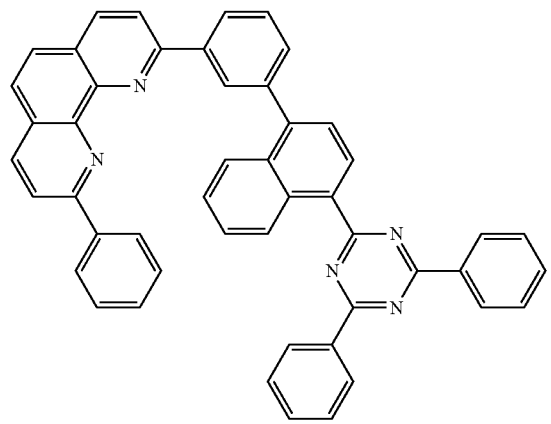
EN-m124
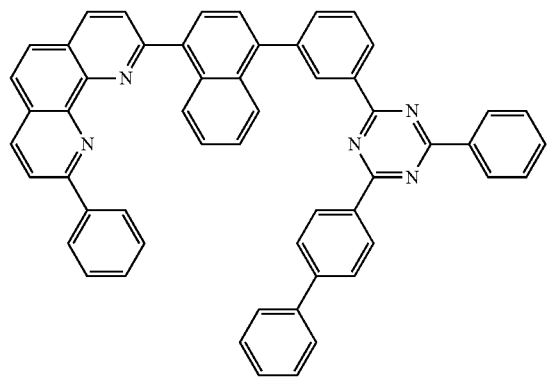

-continued
EN-m125
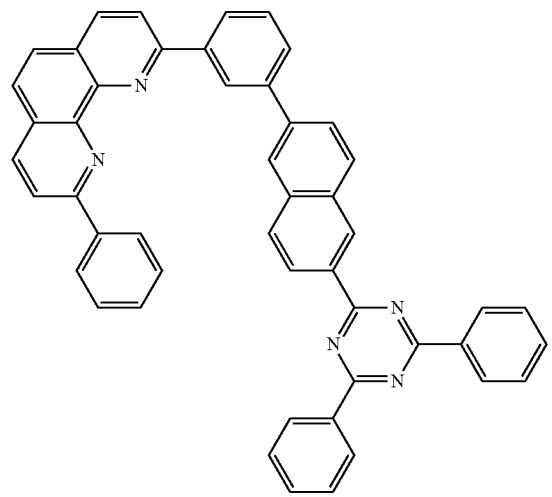
EN-m126
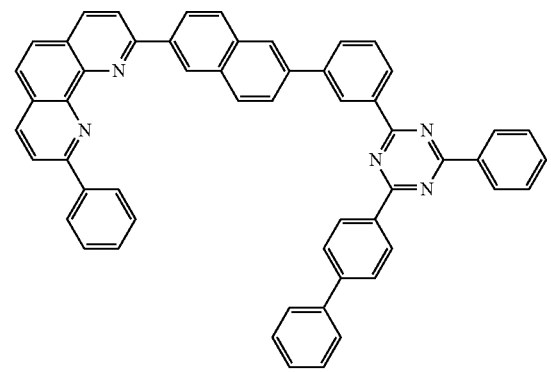
EN-m127
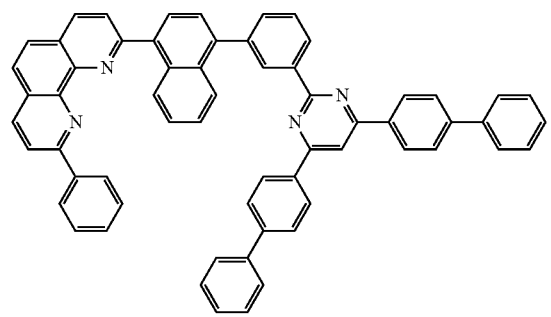
EN-m128
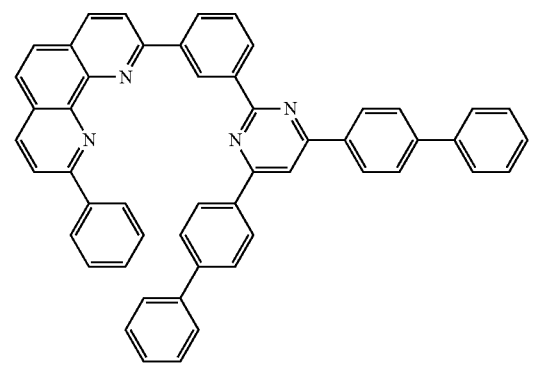
EN-m129
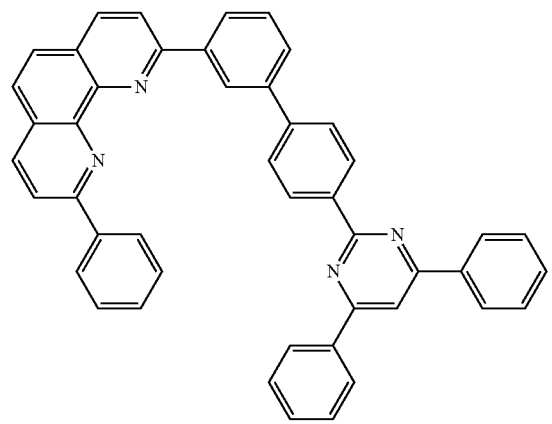
EN-m130
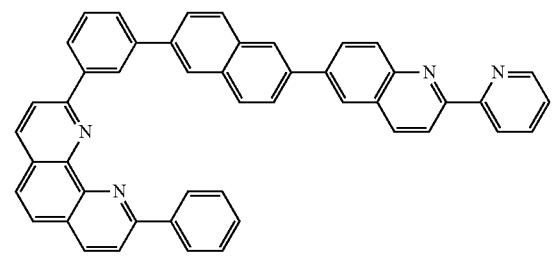

-continued
EN-m131
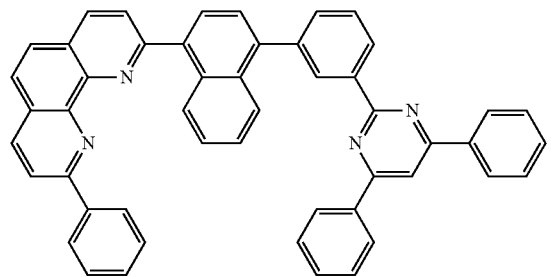
EN-m132
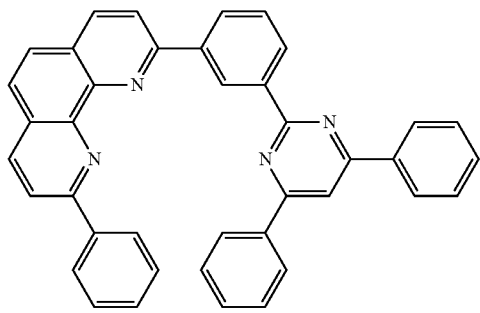
EN-m133
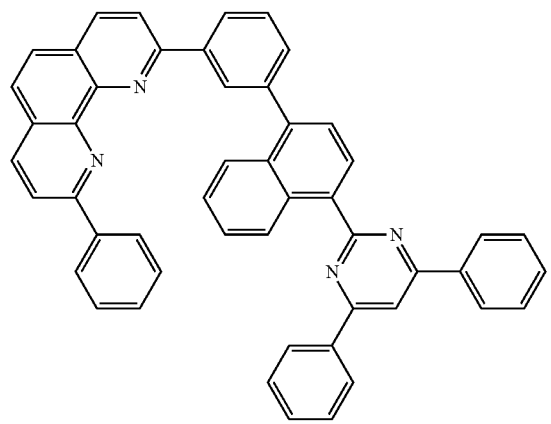
EN-m134
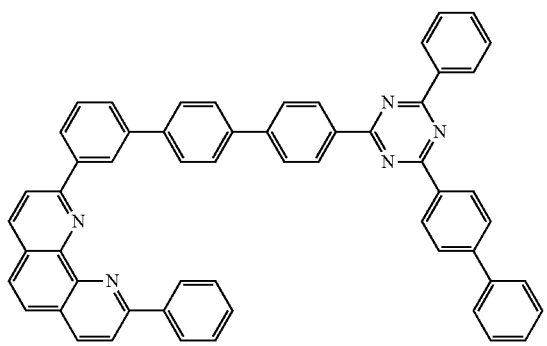
EN-m135
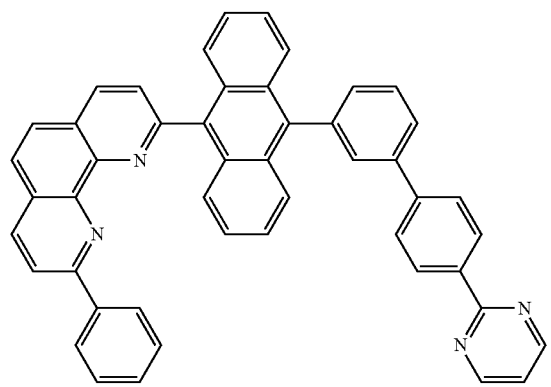
EN-m136
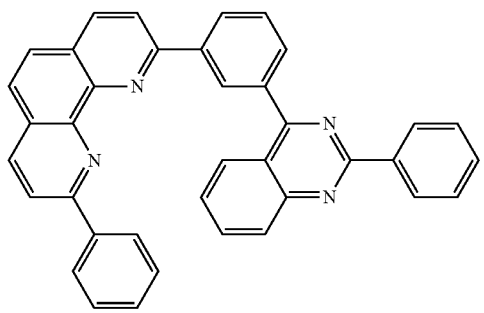
EN-m137
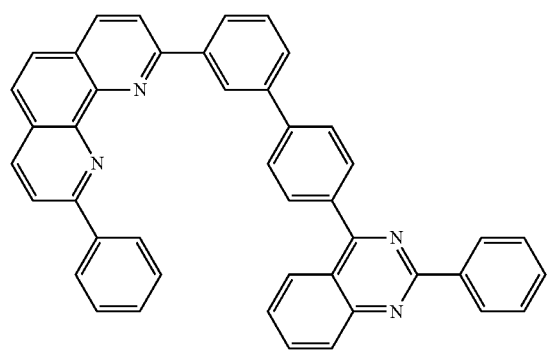
EN-m138
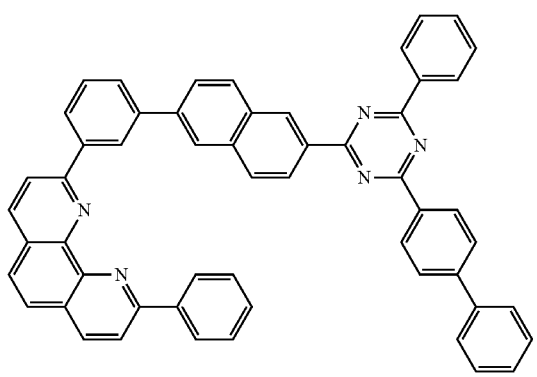

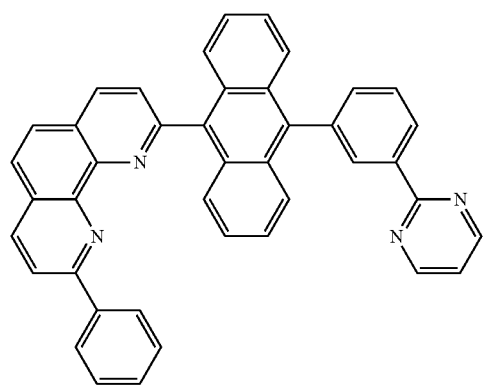

EN-m139

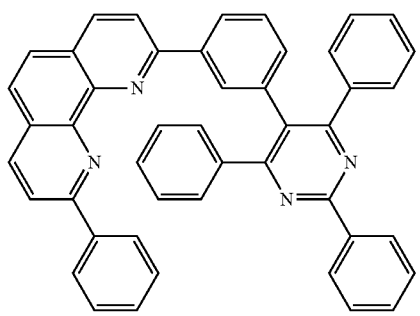

EN-m140

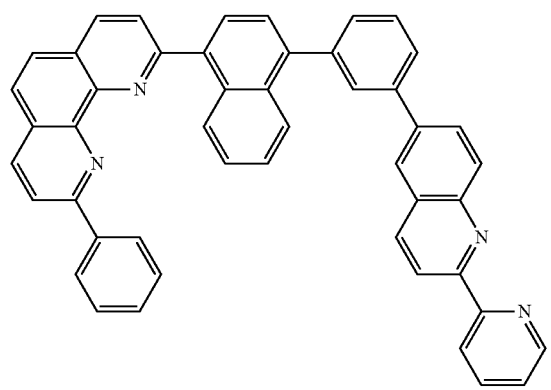

EN-m141

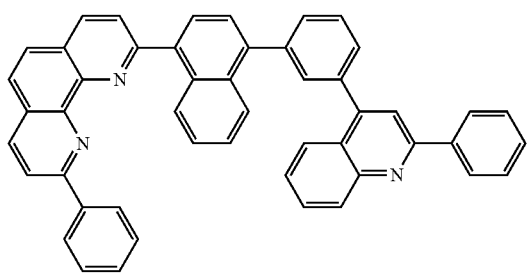

EN-m142

The organic compounds EN-m001 to EN-m142 contain a phenanthroline moiety substituted with an aromatic ring and has high thermal stability and thus improved electron transfer properties, as compared with a compound having phenanthroline not substituted with an aromatic ring. Accordingly, when used as a material for an N-type charge generation layer (n-CGL) of a tandem organic light emitting diode, the organic compounds EN-m001 to EN-m142 can improve lifespan of the organic light emitting diode and reduce driving voltage of the organic light emitting diode while improving luminous efficacy of the organic light emitting diode.

In accordance with another aspect of the present disclosure, there is provided an organic light emitting diode including:

a first electrode and a second electrode facing each other;

a first light emitting stack interposed between the first electrode and the second electrode and including a first light emitting material layer and an electron transport layer;

a second light emitting stack interposed between the first light emitting stack and the second electrode and including a second light emitting material layer; and a first charge generation layer interposed between the first light emitting stack and the second light emitting stack, wherein at least one of the electron transport layer and the first charge generation layer includes the organic compound as set forth above.

The organic compound represented by Formula 1, including Compounds EN-m001 to EN-m142, has good thermal stability since the phenanthroline moiety of the organic compounds, which has good electron transfer properties, is substituted with the aromatic ring. Accordingly, when used as a material for an electron transport layer and/or a charge generation layer of a tandem organic light emitting diode, the organic compound represented by Formula 1 (including Compounds EN-m001 to EN-m142) can reduce driving voltage of the organic light emitting diode while improving luminous efficacy and lifespan of the organic light emitting diode.

FIG. 1 is a schematic sectional view of a tandem organic light emitting diode including two light emitting stacks according to a first exemplary embodiment of the present disclosure.

Referring to FIG. 1, the organic light emitting diode 100 according to the first embodiment includes: a first electrode 110 and a second electrode 120 facing each other; and an organic light emitting layer 130 interposed between the first electrode 110 and the second electrode 120. The organic light emitting layer 130 includes: a first light emitting stack (ST1) 140 interposed between the first electrode 110 and the second electrode 120 and including a first light emitting material layer (lower light emitting material layer) 144; a second light emitting stack (ST2) 150 interposed between the first light emitting stack 140 and the second electrode 120 and including a second light emitting material layer (upper light emitting material layer) 154; and a charge generation layer (CGL) 160 interposed between the first light emitting stack 140 and the second light emitting stack 150.

The first electrode 120 is an anode through which holes are injected into the organic light emitting diode, and may be formed of a conductive material having high work function, for example, any one of indium tin oxide (ITO), indium zinc oxide (IZO), and zinc oxide (ZnO). The second electrode 120 is a cathode through which electrons are injected into the organic light emitting diode, and may be formed of a conductive material having low work function, for example, any one of aluminum (Al), magnesium (Mg), and aluminum-magnesium alloys (AlMg).

The first light emitting stack 140 includes: a hole injection layer 141 interposed between the first electrode 110 and the first light emitting material layer 144, a first hole transport layer 142 interposed between the hole injection layer 141 and the first light emitting material layer 144, and a first electron transport layer (lower electron transport layer) 146 interposed between the first light emitting material layer 144 and the charge generation layer 160.

The hole injection layer 141 improves interface characteristics between the first electrode 120 formed of an inorganic material and the hole transport layer 142 formed of an inorganic material. In one embodiment, the hole injection layer 141 may include one material selected from the group consisting of 4,4',4"-tris(3-methylphenylphenylamino) triphenylamine (MTDATA), copper phthalocyanine (CuPc), tris(4-carbazolyl-9-yl-phenyl)amine (TCTA), N,N'-diphenyl-N,N'-bis(1-naphthyl)-1,1'-biphenyl-4,4"-diamine (NPB, NPD)), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiophene)polystyrene sulfonate (PEDOT/PSS), 2,3,5,6-tetrafluoro-7,7,8,8-tetracyanoquinodimethane (F4-TCNQ), N-(biphenyl-4-yl)-9,9-dimethyl-N-(4-(9-phenyl-9H-carbazol-3-yl)phenyl)-9H-fluoren-2-amine, and combinations thereof.

For example, the hole injection layer 141 may have a thickness of 1 nm to 150 nm. When the thickness of the hole injection layer 141 is greater than or equal to 1 nm, the hole injection layer can exhibit improved hole injection properties, and, when the thickness of the hole injection layer 141 is less than or equal to 150 nm, it is possible to prevent increase in driving voltage of the organic light emitting diode due to increase in thickness of the hole injection layer 141. The hole injection layer 141 may be omitted depending on the structure and characteristics of the organic light emitting diode.

The first hole transport layer 142 is interposed between the hole injection layer 141 and the first light emitting material layer 144; the first light emitting material layer 144 is interposed between the first hole transport layer 142 and the first electron transport layer 146; and the first electron transport layer 146 is interposed between the first light emitting material layer 144 and the charge generation layer 160.

The second light emitting stack 150 includes a second hole transport layer (upper hole transport layer) 152, a second light emitting material layer (upper light emitting material layer) 154, a second electron transport layer (upper electron transport layer) 156, and an electron injection layer 158. The second hole transport layer 152 is interposed between the charge generation layer 160 and the second light emitting material layer 154, and the second light emitting material layer 154 is interposed between the second hole transport layer 152 and the second electrode 120. In addition, the second electron transport layer 156 is interposed between the second light emitting material layer 154 and the second electrode 120, and the electron injection layer 158 is interposed between the second electron transport layer 156 and the second electrode 120.

Each of the first hole transport layer 142 and the second hole transport layer 152 may be formed of any one selected from the group consisting of N,N'-diphenyl-N,N'-bis(3-methylphenyl)-1,1'-biphenyl-4,4'-diamine (TPD), NPD, MTDATA, 1,3-bis(N-carbazolyl)benzene (mCP), CuPC, TCTA, tris(trifluorovinylether)-tris(4-carbazolyl-9-yl-phenyl)amine (TFV-TCTA), tris[4-(diethylamino)phenyl] amine, N-(biphenyl-4-yl)-9,9-dimethyl-N-(4-(9-phenyl-9H-carbazol-3-yl)phenyl)-9H-fluorene-2-amine, tri-p-tolylamine, N-[1,1'-biphenyl]-4-yl-9,9-dimethyl-N-[4-(9-phenyl-9H-carbazol-3-yl)phenyl]-amine, 4,4'-bis(N-carbazolyl)-1,1'-biphenyl (CBP), 1,1-bis(4-(N,N'-di(p-tolyl) amino)phenyl) cyclohexane (TAPC), and combinations thereof.

Each of the first hole transport layer 142 and the second hole transport layer 152 may have a thickness of 1 nm to 150 nm. When the thickness of the first and second hole transport layers 142, 152 is greater than or equal to 1 nm, it is possible to improve hole transport properties, and, when the thickness of the first and second hole transport layers 142, 152 is less than or equal to 150 nm, it is possible to prevent increase in driving voltage of the organic light emitting diode due to increase in thickness of the first and second hole transport layers 142, 152. The first hole transport layer 142 and the second hole transport layer 152 may be formed of the same material or may be formed of different materials.

In one embodiment, each of the first light emitting material layer 144 and the second light emitting material layer 154 may be formed by doping a host with a dopant, and emit light of different colors. Here, the dopant may be present in an amount of 1 wt % to 30 wt % based on the weight of the host.

For example, the first light emitting material layer 144 may emit blue (B) light, red (R) light, green (G) light, or yellow (Y) light. When the first light emitting material layer 144 is a blue light emitting material layer, the first light emitting material layer 144 includes at least one of a blue light emitting material layer, a dark blue light emitting material layer, and a sky blue light emitting material layer. Alternatively, the first light emitting material layer 144 may include a combination of a blue light emitting material layer and a red (R) light emitting material layer, a combination of a blue light emitting material layer and a yellow-green (YG) light emitting material layer, or a combination of a blue light emitting material layer and a green (G) light emitting material layer.

The second light emitting material layer 154 may be any one of red (R), green (G), blue (B), and yellow-green (YG) light emitting material layers. In one embodiment, the first light emitting material layer 144 may be configured to emit blue light and the second light emitting material layer 154 may be configured to emit green (G), yellow-green (YG), yellow (Y), or orange light having longer wavelengths than blue light.

For example, when the first light emitting material layer 144 is configured to emit blue light, the first light emitting material layer 144 may be formed by doping a fluorescent host with a fluorescent dopant, wherein the fluorescent host includes at least one selected from the group consisting of anthracene and derivatives thereof, pyrene and derivatives thereof, and perylene and derivatives thereof.

Examples of a blue fluorescent host that can be used in the first light emitting material layer 144 may include 4,4'-bis (2,2'-diphenylyinyl)-1,1'-biphenyl (DPVBi), 9,10-di-(2-naphtyl)anthracene (ADN), tetra-t-butylperylene (TBADN), 2-tert-butyl-9,10-di(2-naphthyl)anthracene, 2-methyl-9,10-di(2-naphtyl)anthracene (MADN), 2,2',2"-(1,3,5-benzenetriyl)-tris(1-phenyl-1-H-benzimidazole) (TBPi), and combinations thereof.

A blue fluorescent dopant that can be used in the first light emitting material layer 144 may include any one selected from the group consisting of 4,4'-bis(9-ethyl-3-carbazovinylene)-1,1'-biphenyl (BCzVBi), diphenyl-[4-(2-[1,1;4,1] terphenyl-4-yl-vinyl)-phenyl]-amine (BD-1), spiro-DPVBi, spiro-CBP, distyrylbenzene (DSB) and derivatives thereof, distyryl arylene (DSA) and derivatives thereof, polyfluorene (PF) polymers, polyphenylene vinylene (PPV) polymers, and combinations thereof. Optionally, as a blue dopant, an iridium-based dopant, which is a phosphorescent dopant, may be used. In this case, the first light emitting material layer 144 may be a sky blue light emitting material layer or a dark blue light emitting material layer, in addition to a blue light emitting material layer. Here, the emission wavelength of the first light emitting stack 144 may range from 440 nm to 480 nm.

When the first light emitting material layer 144 is a green (G) light emitting material layer, the first light emitting material layer 144 may be a phosphorescent light emitting material layer including a host, such as CBP, and an iridium-based dopant (for example, dp2Ir(acac), op2Ir(acac), etc.), without being limited thereto. Optionally, the first light emitting material layer 144 may be a fluorescent light emitting material layer including tris(8-hydroxyquinolinato) aluminum (Alq). Here, the emission wavelength of the first light emitting stack 144 may range from 510 nm to 570 nm.

When the first light emitting material layer 144 is a red (R) light emitting material layer, the first light emitting material layer 144 may be a phosphorescent light emitting material layer including a host, such as CBP, and at least one dopant selected from the group consisting of bis(1-phenylisoquinoline)acetylacetonate iridium (PIQIr(acac), bis(1-phenylquinoline)acetylacetonate iridium (PQIr(acac), and octaethylporphyrin platinum (PtOEP), without being limited thereto.

Alternatively, the first light emitting material layer 144 may be a fluorescent light emitting material layer including 1,3,4-oxadiazole:tris(dibenzoylmethane)mono(1,10-phentathroline)europium(III) (PBD:Eu(DBM)3(Phen)) or perylene and derivatives thereof. Here, the emission wavelength of the first light emitting material layer 144 may range from 600 nm to 650 nm.

When the first light emitting material layer 144 is a yellow (Y) light emitting material layer, the first light emitting material layer 144 may have a monolayer structure of a yellow-green (YG) light emitting material layer or have a bilayer structure of a yellow-green light emitting material layer and a green light emitting material layer. For example, when the first light emitting material layer 144 is a yellow light emitting material layer, the yellow light emitting material layer may include at least one host selected from among CBP and bis(2-methyl-8-quinolinolate)-4-(phenylphenolato)aluminium (BAlq) and a yellow-green phosphorescent dopant. Here, the emission wavelength of the first light emitting material layer 144 may range from 510 nm to 590 nm.

Optionally, in order to improve red luminous efficiency of the tandem organic light emitting diode 100, the first light emitting material layer 144 may include two light emitting material layers, for example, a yellow-green light emitting material layer and a red light emitting material layer, or a blue light emitting material layer and a red light emitting material layer.

When the second light emitting material layer 154 is a yellow-green light emitting material layer, the second light emitting material layer 154 may have a monolayer structure of a yellow-green (YG) light emitting material layer or have a bilayer structure of a yellow-green light emitting material layer and a green (G) light emitting material layer. When the second light emitting material layer 154 has a monolayer structure of a yellow-green (YG) light emitting material layer, the second light emitting material layer 154 may include at least one host selected from among CBP and BAlq and a yellow-green phosphorescent dopant, without being limited thereto.

When the second light emitting material layer 154 is a yellow light emitting material layer, the second light emitting material layer 154 may include at least one selected from among CBP and BAlq and a yellow phosphorescent dopant.

The first electron transport layer 146 and the second electron transport layer 156 serve to facilitate electron transport in the first light emitting stack 140 and the second light emitting stack 150, respectively. Each of the first and second electron transport layers 146, 156 may include a derivative of oxadiazole, triazole, phenanthroline, benzoxazole, benzothiazole, benzimidazole, triazine, and the like.

For example, each of the first and second electron transport layers 146, 156 may be formed of an electron transport material selected from the group consisting of Alq3, 2-biphenyl-4-yl-5-(4-tbutylphenyl)-1,3,4-oxadiazole (PBD), spiro-PBD, lithium quinolate (Liq), 2-[4-(9,10-Di-2-naphthalenyl-2-anthracenyl)phenyl]-1-phenyl-1H-benzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline) (TPQ), 1,3,5-tri[(3-pyridyl)-phen-3-yl]benzene (TmPyPB), 1,3,5-tris(N-phenylbenzimiazole-2-yl)benzene (TPBI), and combinations thereof. Alternatively, each of the first and second electron transport layers 146, 156 may be formed of the organic compound represented by Formula 1, including Compounds EN-m001 to EN-m142.

Optionally, each of the first and second electron transport layers 146, 156 may be formed by doping with an alkali metal or alkali earth metal compound. Examples of a metal component that can be used as a dopant for the first and second electron transport layers 146, 156 may include an alkali metal, such as lithium (Li), sodium (Na), potassium (K) and cesium (Cs), and an alkali earth metal, such as magnesium (Mg), strontium (Sr), barium (Ba), and radium (Ra), without being limited thereto. The alkali metal or alkali earth metal compound may be added in an amount of about 1 wt % to 20 wt %, without being limited thereto.

Each of the first and second electron transport layers 146, 156 may have a thickness of 1 nm to 150 nm. When the thickness of the first and second electron transport layers 146, 156 is greater than or equal to 1 nm, it is possible to prevent deterioration in electron transport properties, and, when the thickness of the first and second electron transport layers 146, 156 is less than or equal to 150 nm, it is possible to prevent increase in driving voltage due to increase in thickness of the first and second electron transport layers 146, 156. The first electron transport layer 146 and the second electron transport layer 156 may be formed of the same material, or may be formed of different materials.

The electron injection layer 158 serves to secure efficient injection of electrons, and may include alkali halides such as LiF, NaF, KF, RbF, CsF, FrF, BeF$_2$, MgF$_2$, CaF$_2$, SrF$_2$, BaF$_2$ and RaF$_2$, and/or organic materials such as Liq (lithium quinolate), lithium benzoate, sodium stearate, Alq3, BAlq, PBD, spiro-PBD, and TAZ.

The electron injection layer 158 may have a thickness of 0.5 nm to 50 nm. When the thickness of the electron injection layer 158 is greater than or equal to 0.5 nm, it is possible to prevent deterioration in electron injection properties, and, when the thickness of the electron injection layer 158 is less than or equal to 50 nm, it is possible to prevent increase in driving voltage due to increase in thickness of the electron injection layer 158.

In the tandem organic light emitting diode 100, the charge generation layer (CGL) 160 is interposed between the first light emitting stack 140 and the second light emitting stack 150 to improve current efficiency in each light emitting layer while securing efficient distribution of charges. That is, the charge generation layer 160 is interposed between the first light emitting stack 140 and the second light emitting stack 150, and the first light emitting stack 140 is connected to the second light emitting stack 150 by the charge generation layer 160. The charge generation layer 160 may be a PN junction charge generation layer in which an N-type charge generation layer 162 adjoins a P-type charge generation layer 164.

The N-type charge generation layer 162 is interposed between the first electron transport layer 146 and the second hole transport layer 152, and the P-type charge generation layer 164 is interposed between the N-type charge generation layer 162 and the second hole transport layer 152. The charge generation layer 160 generates charges or divides the charges into holes and electrons to supply the holes and electrons to the first and second light emitting stacks 140, 150.

That is, the N-type charge generation layer 162 supplies electrons to the first electron transport layer 146 of the first light emitting stack 140, which, in turn, supplies the electrons to the first light emitting material layer 144 adjacent to the first electrode 110. The P-type charge generation layer 164 supplies holes to the second hole transport layer 152 of the second light emitting stack 150, which, in turn, supplies the holes to the second light emitting material layer 154 adjacent to the second electrode 120.

Here, the P-type charge generation layer 164 may be formed of a metal or a P-doped organic material. Here, the metal may include at least one selected from the group consisting of Al, Cu, Fe, Pb, Zn, Au, Pt, W, In, Mo, Ni, Ti, and alloys thereof. In addition, a P-type dopant and a host used for the P-doped organic material may include any suitable materials commonly used in the art. For example, the P-type dopant may be any one selected from the group consisting of F4-TCNQ, iodine, $FeCl_3$, $FeF_3$, and $SbCl_5$. In addition, the host may include at least one selected from the group consisting of NPB, TPD, N,N,N',N'-tetranaphthalenyl-benzidine (TNB), and HATCN.

Due to a difference in lowest unoccupied molecular orbital (LUMO) energy level between the first electron transport layer 146 and the N-type charge generation layer 162, the driving voltage of the light emitting diode 100 can rise when electrons migrate from the N-type charge generation layer 162 to the first electron transport layer 146. In order to solve such a problem, the organic compound represented by Formula 1 (including Compounds EN-m001 to EN-m142) may be used in the N-type charge generation layer 162 and/or the first electron transport layer 146. Optionally, the N-type charge generation layer 162 may further include a metal compound such as an alkali metal or alkali earth metal compound, as a dopant. The alkali metal or alkali earth metal may be present in an amount of 1 wt % to 30 wt % based on the weight of the organic compound according to the disclosure, without being limited thereto.

Doping the N-type charge generation layer 162 with the alkali metal or alkali earth metal compound can improve electron injection into the N-type charge generation layer 162. Specifically, the alkali metal or alkali earth metal used as a dopant in the N-type charge generation layer 162 is combined with the organic compound according to the present disclosure to form a gap state. As a result, the difference in energy level between the N-type charge generation layer 162 and the P-type charge generation layer 164 is reduced, thereby improving electron injection from the N-type charge generation layer 162 into the first electron transport layer 146.

As described above, the organic compound according to the present disclosure has a phenanthroline moiety substituted with at least one aromatic ring. Since the organic compound has a high decomposition temperature or glass transition temperature and thus high thermal stability due to the presence of the aromatic ring-substituted phenanthroline moiety, the organic compound can be prevented from being deteriorated or degraded by Joule's heat generated upon operation of the organic light emitting diode. Accordingly, when used in the organic light emitting diode 100, the organic compound according to the disclosure can improve lifespan of the organic light emitting diode 100 while reducing driving voltage of the organic light emitting diode 100.

Further, since the phenanthroline moiety of the organic compound according to the present disclosure has a nitrogen atom having an $sp^2$ hybrid orbital, which is relatively rich in electrons, the organic compound has good electron transfer properties. Accordingly, the organic compound may be used in the electron transport layers 146, 156 and/or the charge generation layer 160.

In particular, the nitrogen atom of the phenanthroline moiety is bonded to the alkali metal or alkali earth metal compound, which is a dopant of the N-type charge generation layer, to form a gap state. As a result, a difference in energy level between the N-type charge generation layer and the P-type charge generation layer is reduced, such that electron injection into the N-type charge generation layer can be facilitated while electron transfer from the N-type charge generation layer to the adjacent electron transport layer can be maximized.

That is, use of the organic compound represented by Formula 1 (including Compounds EN-m001 to EN-m142) in the N-type charge generation layer 162 can provide efficient transfer of electrons from the N-type charge generation layer 162 to the first electron transport layer 146.

In addition, the organic compound containing nitrogen atoms is combined with the alkali metal or alkali earth metal compound in the N-type charge generation layer, thereby preventing the alkali metal or alkali earth metal compound from diffusing into the P-type charge generation layer. As a result, it is possible to prevent reduction in lifespan of the organic light emitting diode.

Figure 2:
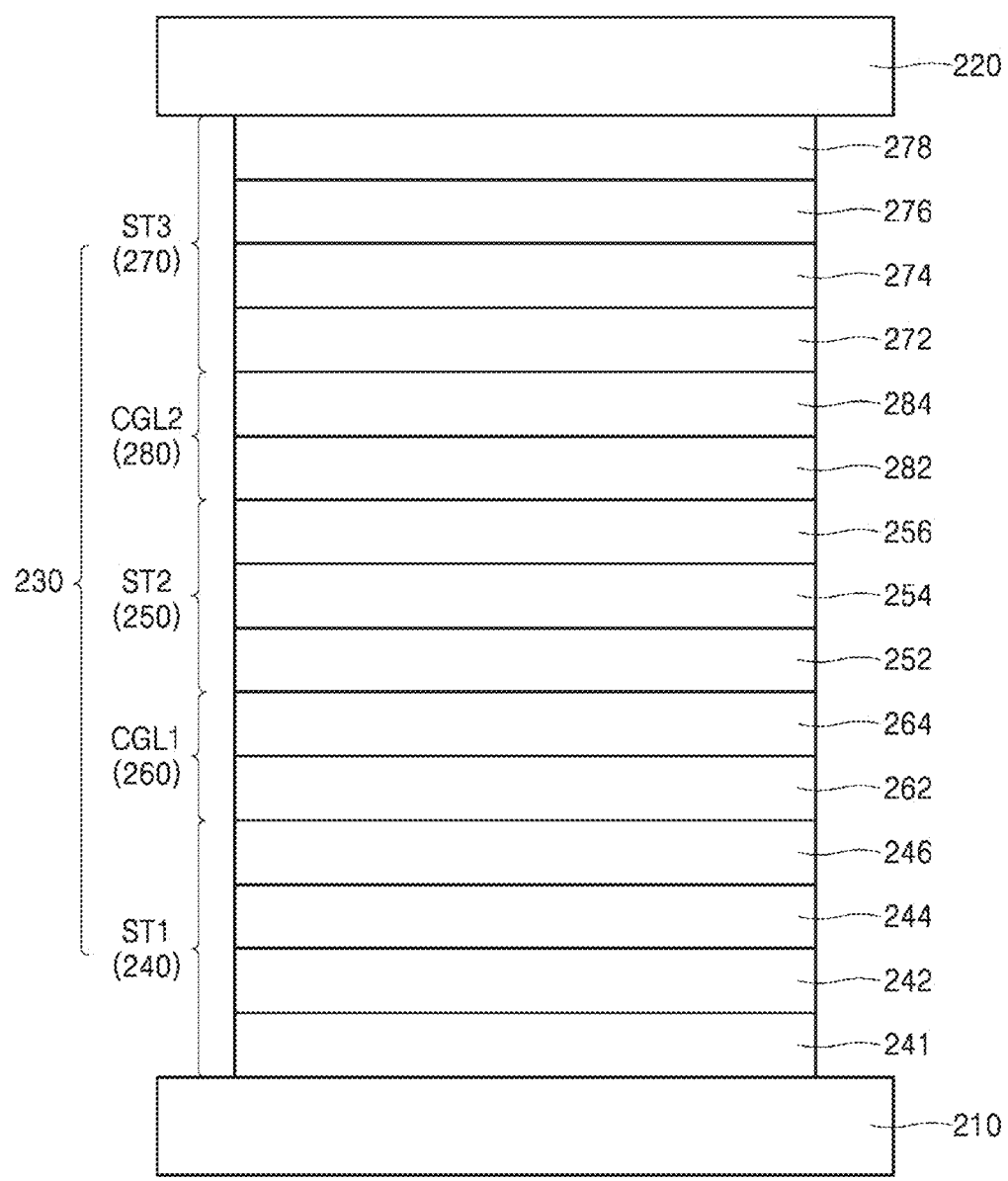
FIG. 2 is a schematic sectional view of an organic light emitting diode including two charge generation layers between three light emitting stacks according to another embodiment of the present disclosure, wherein the charge generation layers include an organic compound represented by Formula 1.

FIG. 2 is a schematic sectional view of an organic light emitting diode including two charge generation layers between three light emitting stacks according to another embodiment of the present disclosure.

Referring to FIG. 2, an organic light emitting diode 200 according to another embodiment of the disclosure includes: a first electrode 210 and a second electrode 220 facing each other; and an organic light emitting layer 230 interposed between the first electrode 210 and the second electrode 220. The organic light emitting layer 230 may include a first light emitting stack (ST1) 240, a second light emitting stack (ST2) 250, a third light emitting stack (ST3) 270, a first charge generation layer (CGL1) 260, and a second charge generation layer (CGL2) 280. Alternatively, four or more light emitting stacks and three or more charge generation layers may be disposed between the first electrode 210 and the second electrode 220.

As described above, the first electrode 210 is an anode through which holes are injected into the organic light emitting diode and may be formed of a conductive material having high work function, for example, any one of ITO, IZO, and ZnO, and the second electrode 220 is a cathode through which electrons are injected into the organic light emitting diode and may be formed of a conductive material having low work function, for example, any one of aluminum (Al), magnesium (Mg), and aluminum-magnesium alloys (AlMg).

The first charge generation layer 260 and the second charge generation layer 280 are interposed between the first light emitting stack 240 and the second light emitting stack 250 and between the second light emitting stack 250 and the third light emitting stack 270, respectively, and the first light emitting stack 240, the first charge generation layer 260, the second light emitting stack 250, the second charge generation layer 280, and the third light emitting stack 270 are sequentially stacked on the first electrode 210. That is, the first light emitting stack 240 is interposed between the first electrode 210 and the first charge generation layer 260; the second light emitting stack 250 is interposed between the first charge generation layer 260 and the second charge generation layer 280; and the third light emitting stack 270 is interposed between the second electrode 220 and the second charge generation layer 280.

The first light emitting stack 240 may include a hole injection layer 241, a first hole transport layer 242, a first light emitting material layer 244, and a first electron transport layer 246, sequentially stacked on the first electrode 210. Here, the hole injection layer 241 and the first hole transport layer 242 are interposed between the first electrode 210 and the first light emitting material layer 244, wherein the hole injection layer 241 is interposed between the first electrode 210 and the first hole transport layer 242. In addition, the first electron transport layer 246 is interposed between the first light emitting material layer 244 and the first charge generation layer 260.

The hole injection layer 241, the first hole transport layer 242, the first light emitting material layer 244, and the first electron transport layer 246 may have the same characteristics as the hole injection layer 141, the first hole transport layer 142, the first light emitting material layer 144, and the first electron transport layer 146 shown in FIG. 1, respectively, and detailed description thereof will be omitted. For example, the first light emitting material layer 244 may be a blue (B) light emitting material layer. Here, the emission wavelength of the first light emitting stack 240 may range from 440 nm to 480 nm.

The second light emitting stack 250 may include a second hole transport layer 252, a second light emitting material layer 254, and a second electron transport layer 256. The second hole transport layer 252 is interposed between the first charge generation layer 260 and the second light emitting material layer 254, and the second electron transport layer 256 is interposed between the second light emitting material layer 254 and the second charge generation layer 280.

The second hole transport layer 252, the second light emitting material layer 254, and the second electron transport layer 256 may have the same characteristics as the second hole transport layer 152, the second light emitting material layer 154, and the second electron transport layer 156 shown in FIG. 1, respectively, and detailed description thereof will be omitted. For example, the second light emitting material layer 254 may be a yellow-green (YG) or yellow light emitting material layer. Here, the emission wavelength of the second light emitting stack 250 may range from 510 nm to 590 nm or from 460 nm to 510 nm.

The third light emitting stack 270 may include a third hole transport layer 272, a third light emitting material layer 274, a third electron transport layer 276, and an electron injection layer 278. The third hole transport layer 272 is interposed between the second charge generation layer 280 and the third light emitting material layer 274; the third electron transport layer 276 is interposed between the third light emitting material layer 274 and the second electrode 220; and the electron injection layer 278 is interposed between the third electron transport layer 276 and the second electrode 220.

The third hole transport layer 272, the third electron transport layer 276, and the electron injection layer 278 may have the same characteristics as the second hole transport layer 152, the second electron transport layer 156, and the electron injection layer 158 shown in FIG. 1, respectively, and detailed description thereof will be omitted. The third light emitting material layer 274 may have the same characteristics as the first light emitting material layer 144 or the second light emitting material layer 154. For example, the third light emitting material layer 274 may be a blue (B) light emitting material layer. Here, the emission wavelength of the third light emitting stack 270 may range from 440 nm to 480 nm. In another optional embodiment, the third light emitting material layer 274 may be a yellow-green (YG) or yellow light emitting material layer, wherein the emission wavelength of the third light emitting stack 270 may range from 460 nm to 590 nm.

For example, at least one of the first electron transport layer 246, the second electron transport layer 256, and the third electron transport layer 276 may be formed of the organic compound represented by Formula 1, including Compounds EN-m001 to EN-m142.

The first charge generation layer 260 is interposed between the first light emitting stack 240 and the second light emitting stack 250 and the second charge generation layer 280 is interposed between the second light emitting stack 250 and the third light emitting stack 270. The first and second charge generation layers 260, 280 may be PN junction charge generation layers in which N-type charge generation layers 262, 282 adjoin P-type charge generation layers 264, 284, respectively.

In the first charge generation layer 260, the N-type charge generation layer 262 is interposed between the first electron transport layer 246 and the second hole transport layer 252 and the P-type charge generation layer 264 is interposed between the N-type charge generation layer 262 and the second hole transport layer 252.

In the second charge generation layer 280, the N-type charge generation layer 282 is interposed between the second electron transport layer 256 and the third hole transport layer 272 and the P-type charge generation layer 284 is interposed between the N-type charge generation layer 282 and the third hole transport layer 272.

The first and second charge generation layers 260, 280 generate charges or divide the charges into holes and electrons to supply the holes and electrons to the first to third light emitting stacks 240, 250, 270.

That is, in the first charge generation layer 260, the N-type charge generation layer 262 supplies electrons to the first electron transport layer 246 of the first light emitting stack 240 and the P-type charge generation layer 264 supplies holes to the second hole transport layer 252 of the second light emitting stack 250.

In the second charge generation layer 280, the N-type charge generation layer 282 supplies electrons to the second electron transport layer 256 of the second light emitting stack 250 and the P-type charge generation layer 284 supplies holes to the third hole transport layer 272 of the third light emitting stack 270.

Here, each of the P-type charge generation layers 264, 284 may be formed of a metal or a P-doped organic material. Here, the metal may include at least one selected from the group consisting of Al, Cu, Fe, Pb, Zn, Au, Pt, W, In, Mo, Ni, Ti, and alloys thereof. In addition, a P-type dopant and a host used for the P-doped organic material may include any suitable materials commonly used in the art. For example, the P-type dopant may be any one selected from the group consisting of F4-TCNQ, iodine, $FeCl_3$, $FeF_3$, and $SbCl_5$. In addition, the host may include at least one selected from the group consisting of NPB, TPD, TNB, and HATCN.

Due to a difference in LUMO energy level between the first and second electron transport layers 246, 256 and the N-type charge generation layers 262, 282, the driving voltage of the organic light emitting diode can rise when electrons migrate from the N-type charge generation layers 262, 282 to the first and second electron transport layers 246, 256.

In order to solve such a problem, at least one of the N-type charge generation layers 262, 282 and/or at least one of the first and second electron transport layers 246, 256 may include the organic compound according to the present disclosure. Optionally, the N-type charge generation layers 262, 282 may include a metal compound such as an alkali metal or alkali earth metal compound, as a dopant.

For example, in addition to the organic compound according to the present disclosure, the N-type charge generation layers 262, 282 may include at least one selected from the group consisting of LiQ, LiF, NaF, KF, RbF, CsF, FrF, $BeF_2$, $MgF_2$, $CaF_2$, $SrF_2$, $BaF_2$, and $RaF_2$, without being limited thereto.

Doping the N-type charge generation layers 262, 282 with the alkali metal or alkali earth metal compound can improve electron injection into the N-type charge generation layers 262, 282.

As described above, the organic compound according to the present disclosure has a phenanthroline moiety substituted with at least one aromatic ring. Since the organic compound has high thermal stability due to the presence of the aromatic ring-substituted phenanthroline moiety, the organic compound is prevented from being deteriorated or degraded by high-temperature heat generated upon operation of a device. Accordingly, when used in the organic light emitting diode 200, the organic compound according to the disclosure can increase lifespan of the organic light emitting diode 200 while reducing driving voltage of the organic light emitting diode 200.

In addition, since the phenanthroline moiety of the organic compound according to the present disclosure has a nitrogen atom having a $sp^2$ hybrid orbital, which is relatively rich in electrons, the organic compound has good electron transport properties. Thus, the organic compound may be used in the electron transport layers 246, 256, 276 and/or the charge generation layers 260, 280.

In particular, the nitrogen atom of the phenanthroline moiety is bonded to the alkali metal or alkali earth metal compound, which is a dopant of the N-type charge generation layer, to form a gap state. As a result, a difference in energy level between the N-type charge generation layer and the P-type charge generation layer is reduced, such that electron injection into the N-type charge generation layer can be facilitated while electron transfer from the N-type charge generation layer to the electron transport layer adjacent thereto can be maximized.

In addition, the organic compound having nitrogen atoms is combined with the alkali metal or alkali earth metal compound in the N-type charge generation layer, thereby preventing the alkali metal or alkali earth metal compound from diffusing into the P-type charge generation layer. As a result, reduction in lifespan of the organic light emitting diode can be prevented.

The organic light emitting diode according to the present disclosure may be used in organic light emitting displays, OLED lighting devices, and the like.

According to the present disclosure, an organic light emitting display is provided, comprising:

a substrate;

the organic light emitting diode as above set forth disposed on the substrate; and a driving device interposed between the substrate and the organic light emitting diode and connected to the first electrode of the organic light emitting diode.

Figure 3:
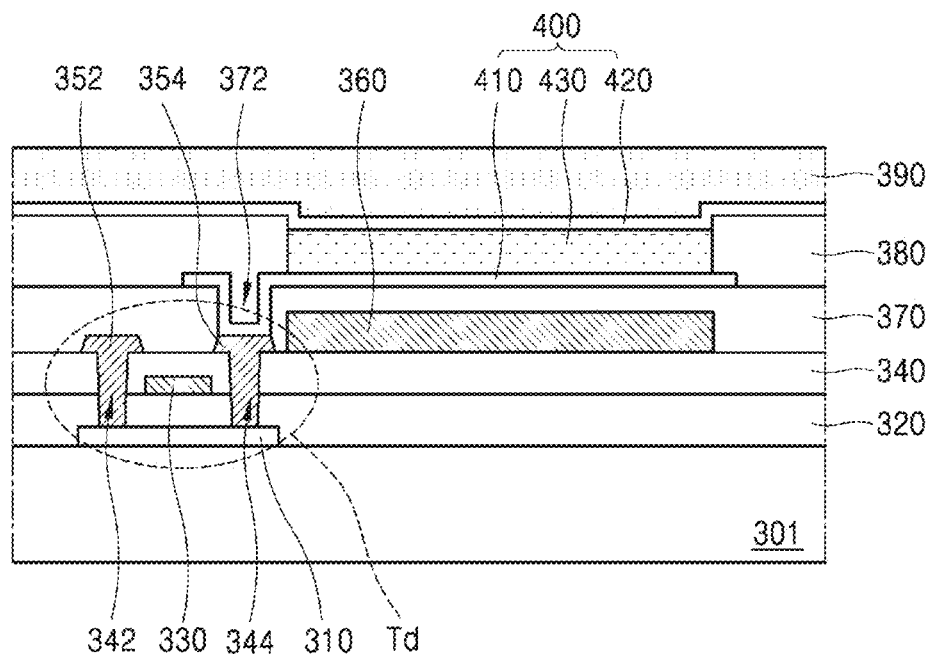
FIG. 3 is a schematic sectional view of an organic light emitting display including an organic light emitting diode according to a further embodiment of the present disclosure.
Figure 4:
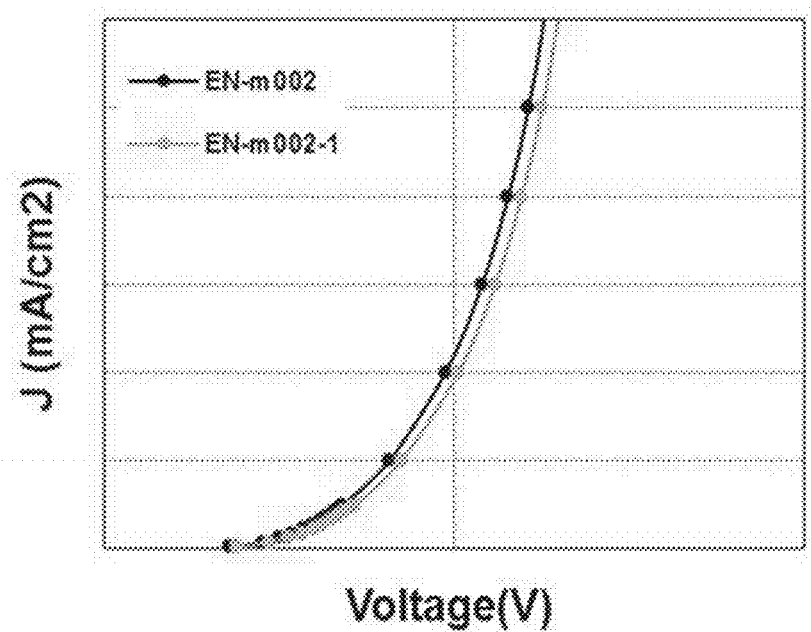
FIG. 4 to FIG. 7 are graphs depicting results of determining current density, current efficiency, external quantum efficiency (EQE), and lifespan of tandem organic light emitting diodes including organic compounds prepared in Example 1 and Comparative Example 1, respectively.
Figure 5:
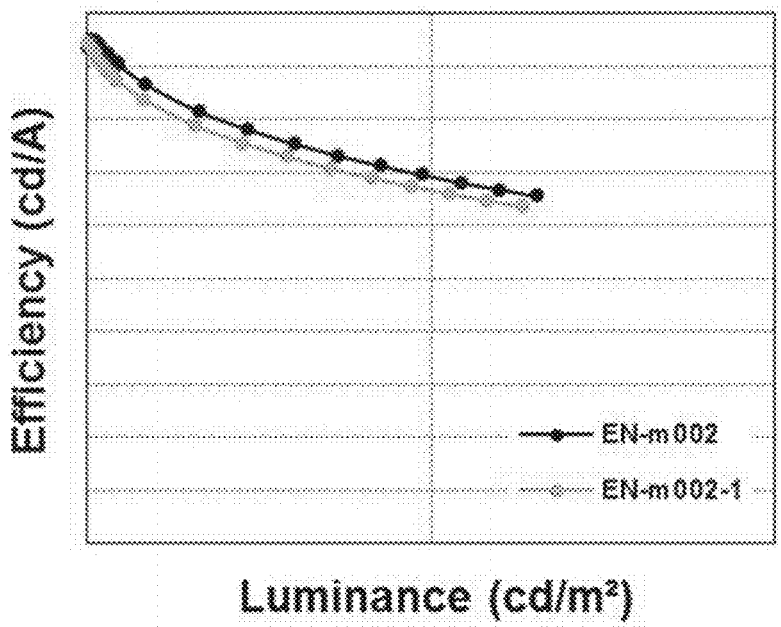
Figure 6:
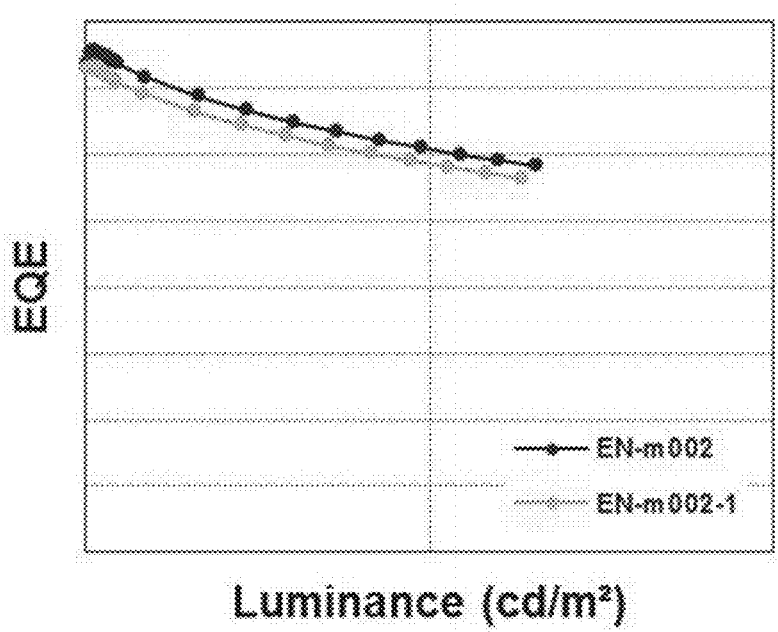
Figure 7:
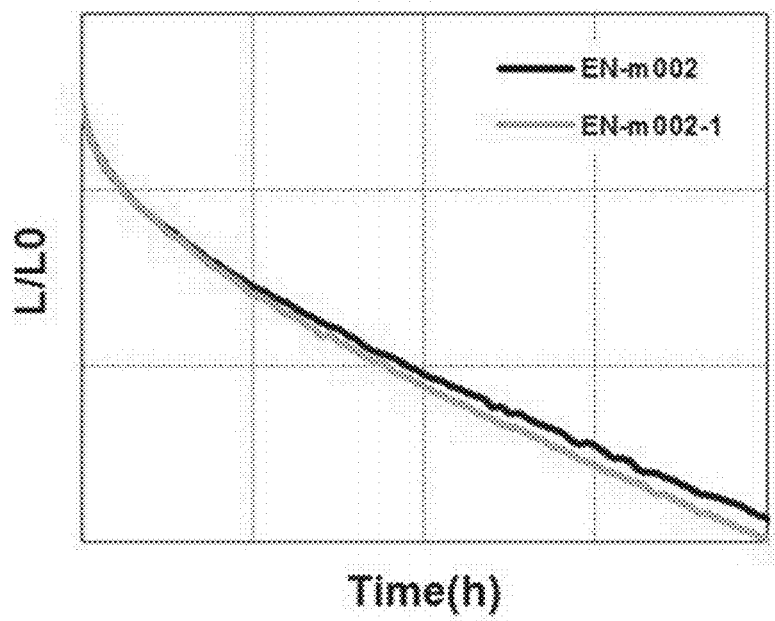
Figure 8:
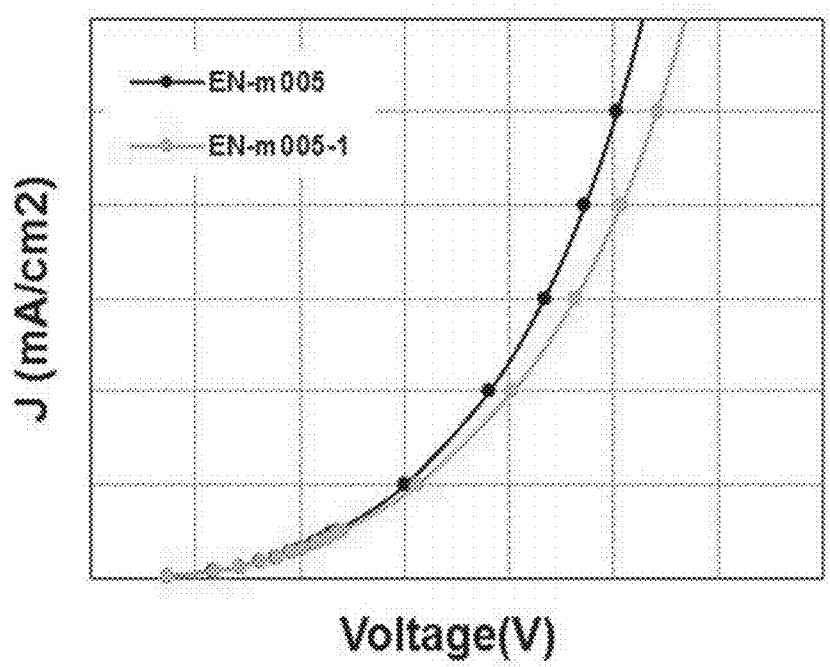
FIG. 8 to FIG. 11 are graphs depicting results of determining current density, current efficiency, external quantum efficiency (EQE), and lifespan of tandem organic light emitting diodes including organic compounds prepared in Example 2 and Comparative Example 2, respectively.
Figure 9:
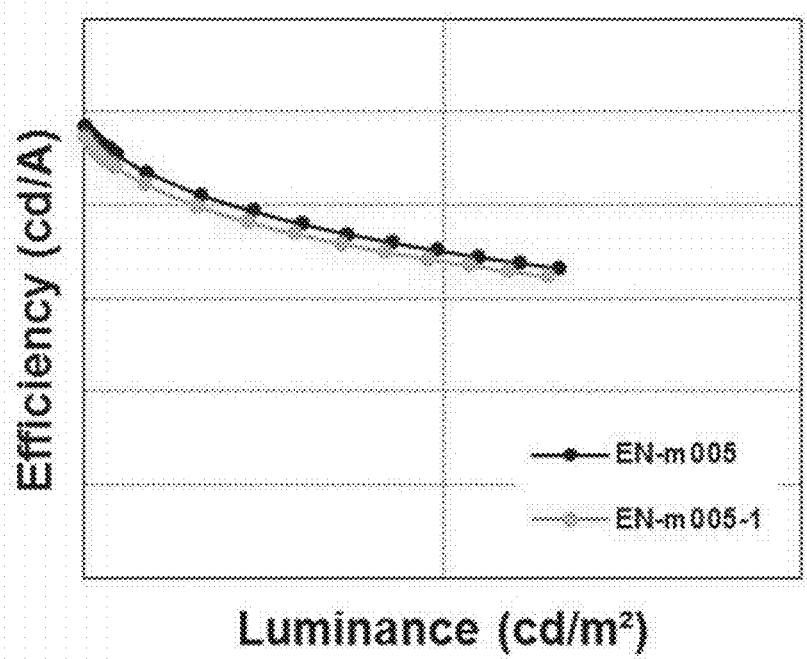
Figure 10:
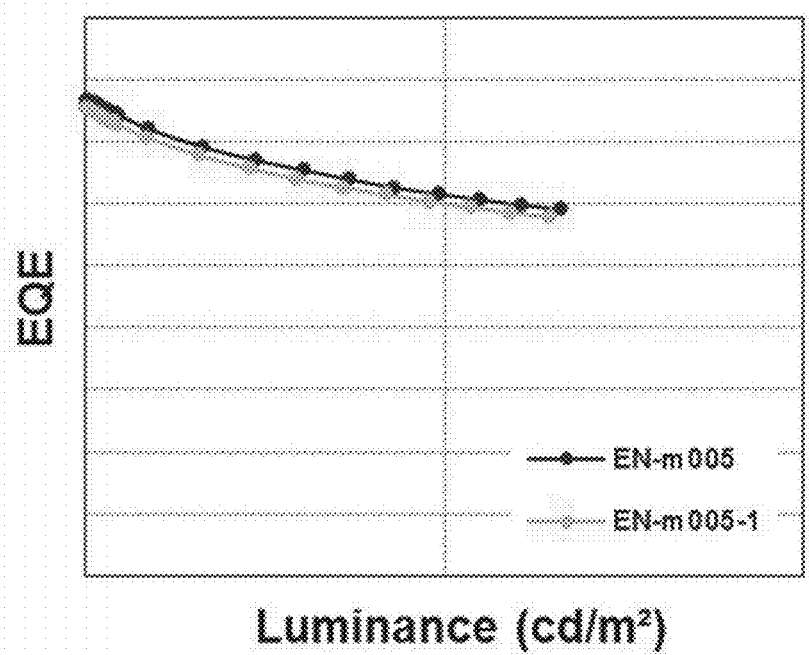
Figure 11:
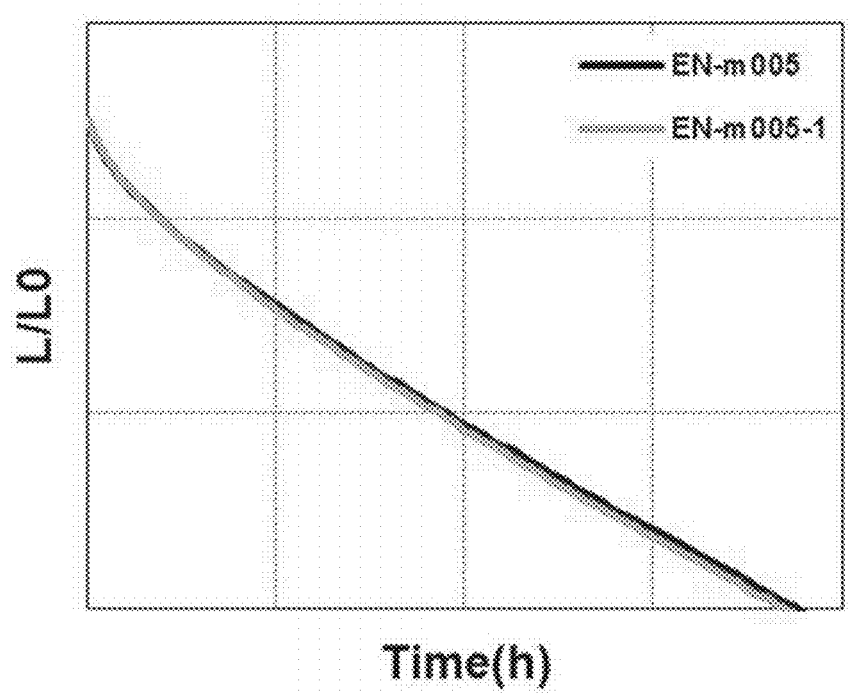
Figure 12:
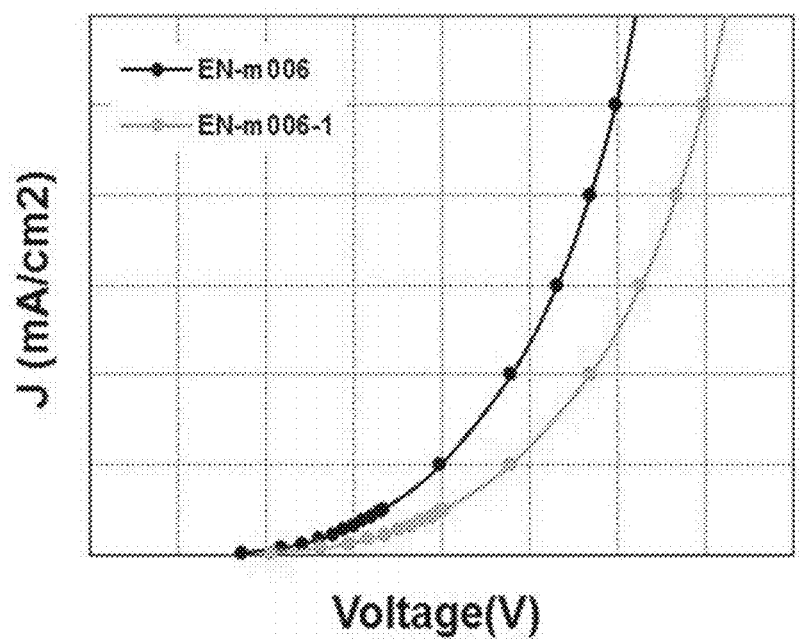
FIG. 12 to FIG. 15 are graphs depicting results of determining current density, current efficiency, external quantum efficiency (EQE), and lifespan of tandem organic light emitting diodes including organic compounds prepared in Example 3 and Comparative Example 3, respectively.
Figure 13:
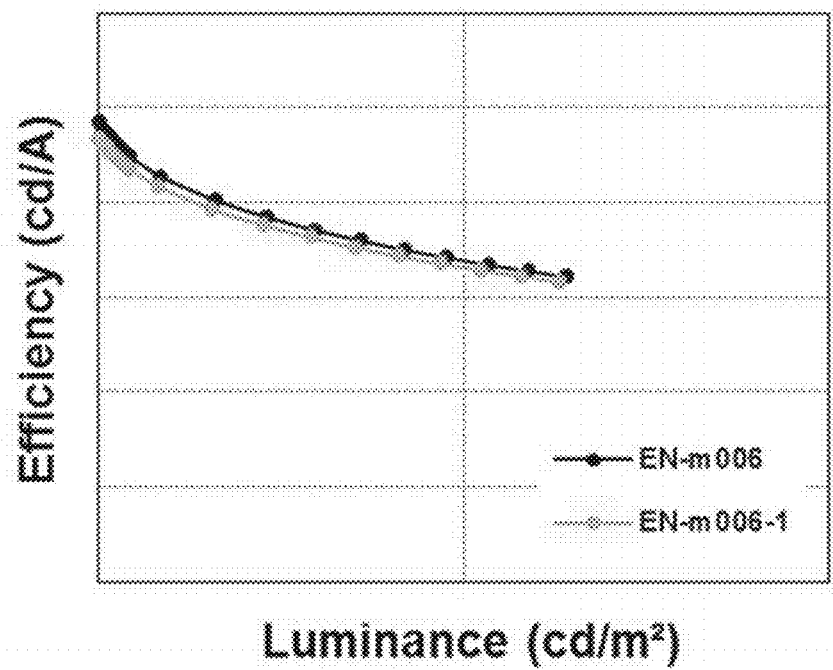
Figure 14:
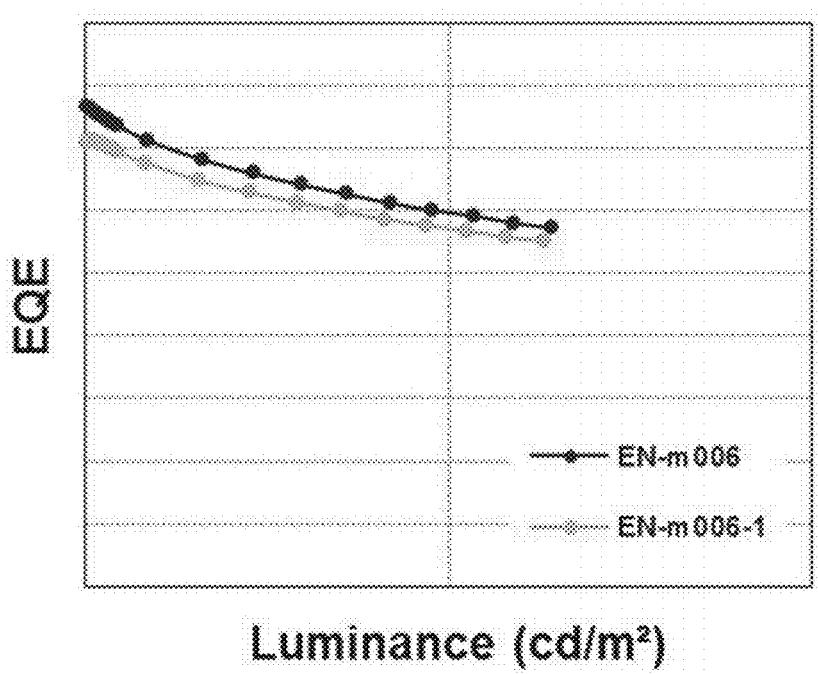
Figure 15:
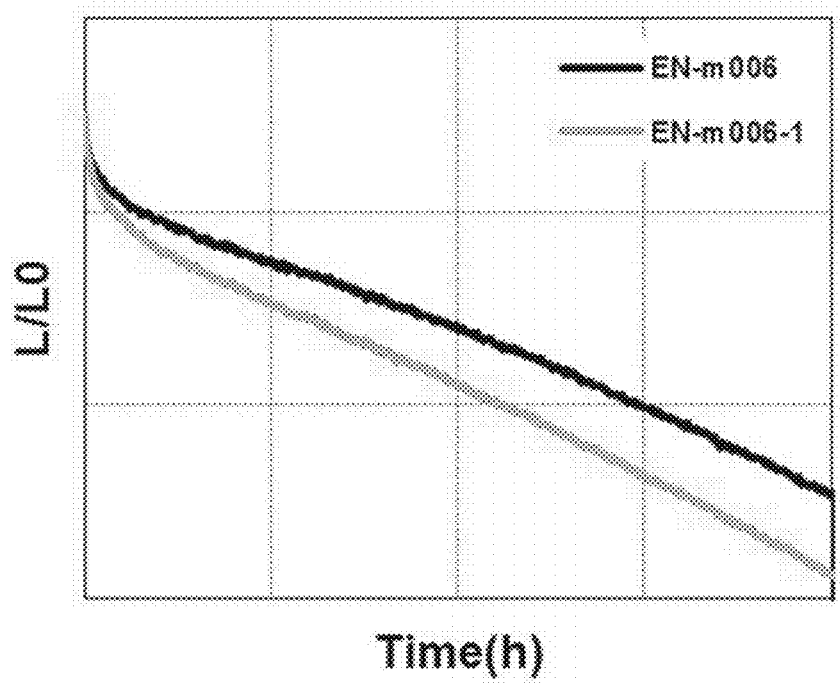
Figure 16:
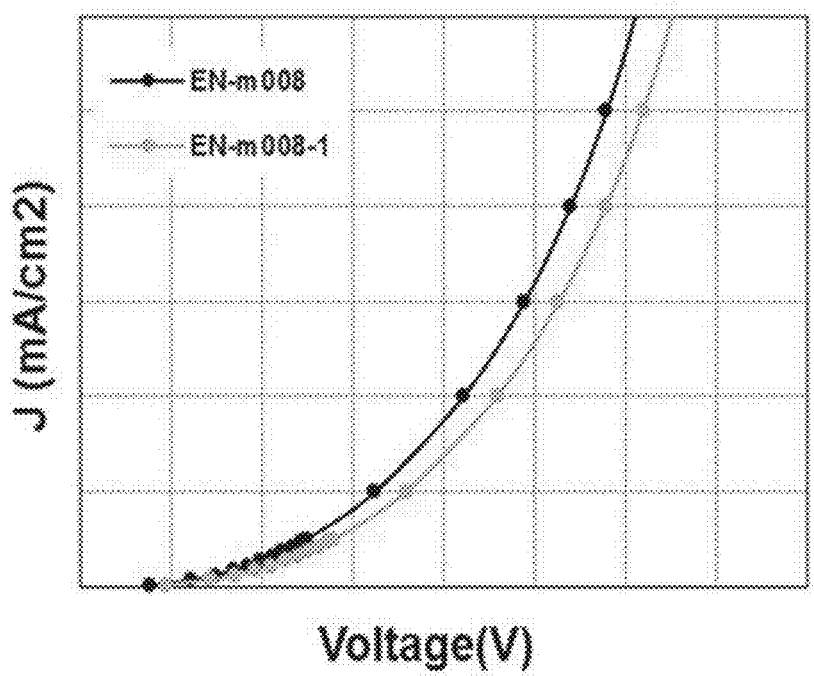
FIG. 16 to FIG. 19 are graphs depicting results of determining current density, current efficiency, external quantum efficiency (EQE), and lifespan of tandem organic light emitting diodes including organic compounds prepared in Example 4 and Comparative Example 4, respectively.
Figure 17:
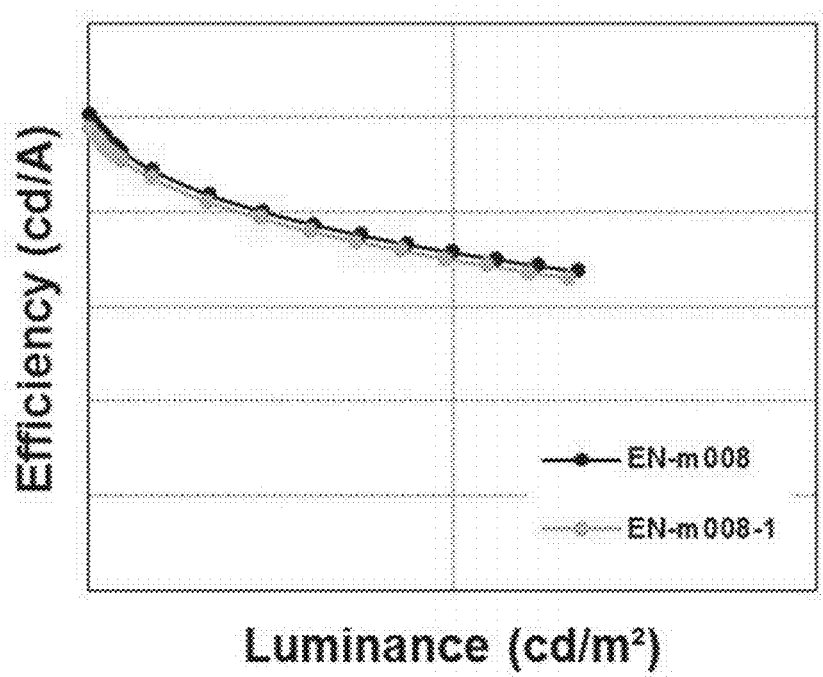
Figure 18:
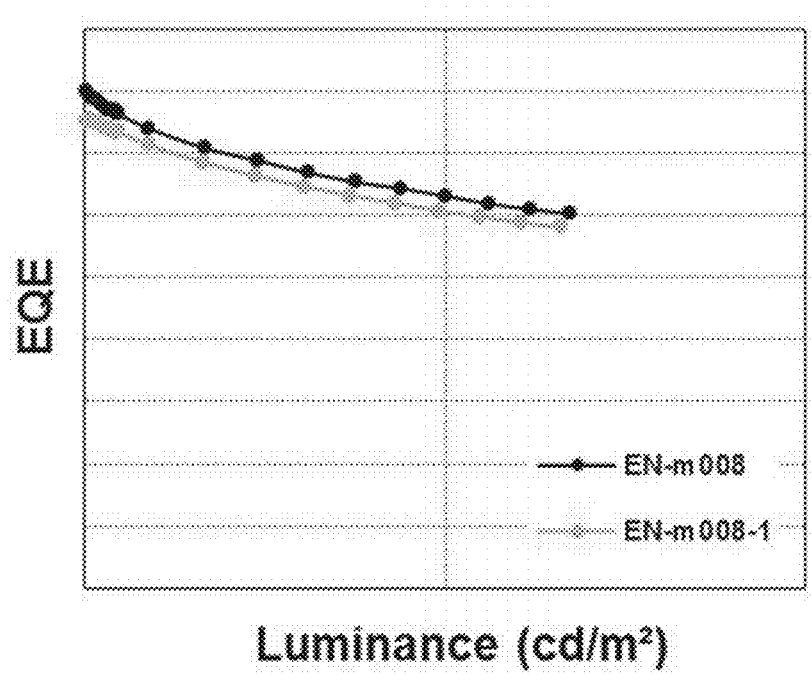
Figure 19:
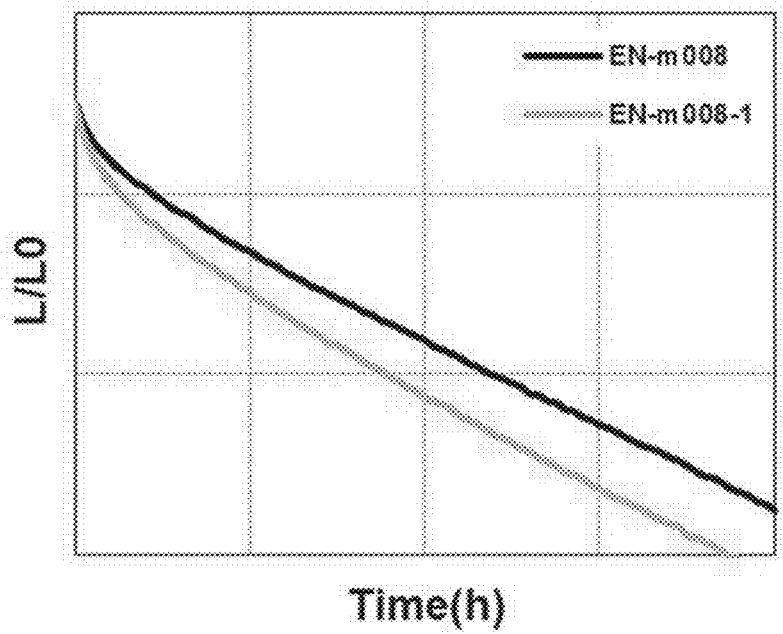
Figure 20:
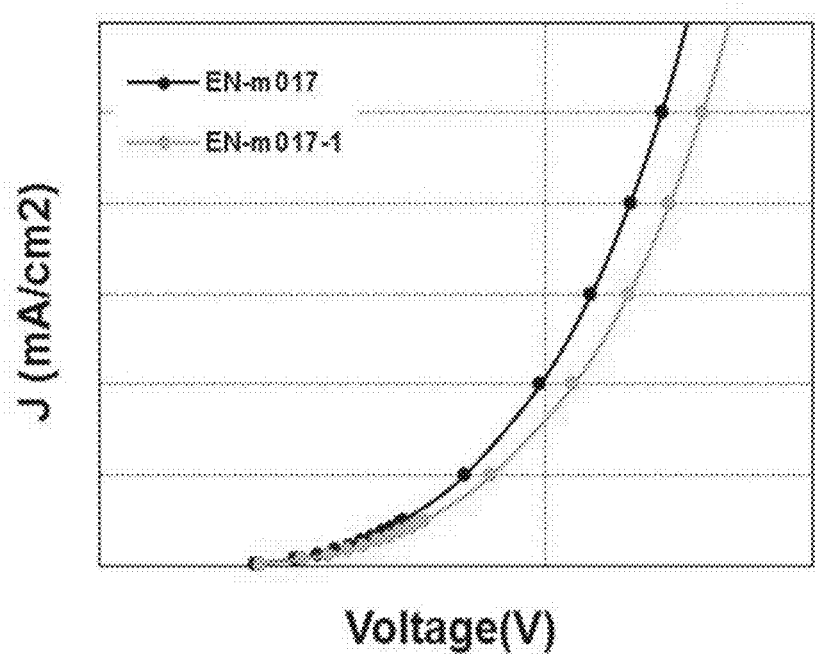
FIG. 20 to FIG. 23 are graphs depicting results of determining current density, current efficiency, external quantum efficiency (EQE), and lifespan of tandem organic light emitting diodes including organic compounds prepared in Example 5 and Comparative Example 5, respectively.
Figure 21:
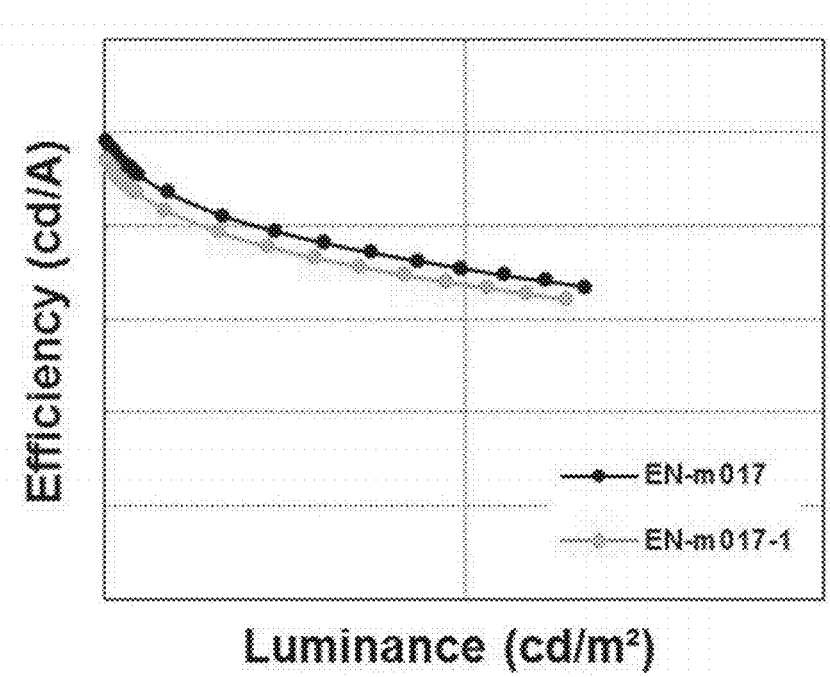
Figure 22:
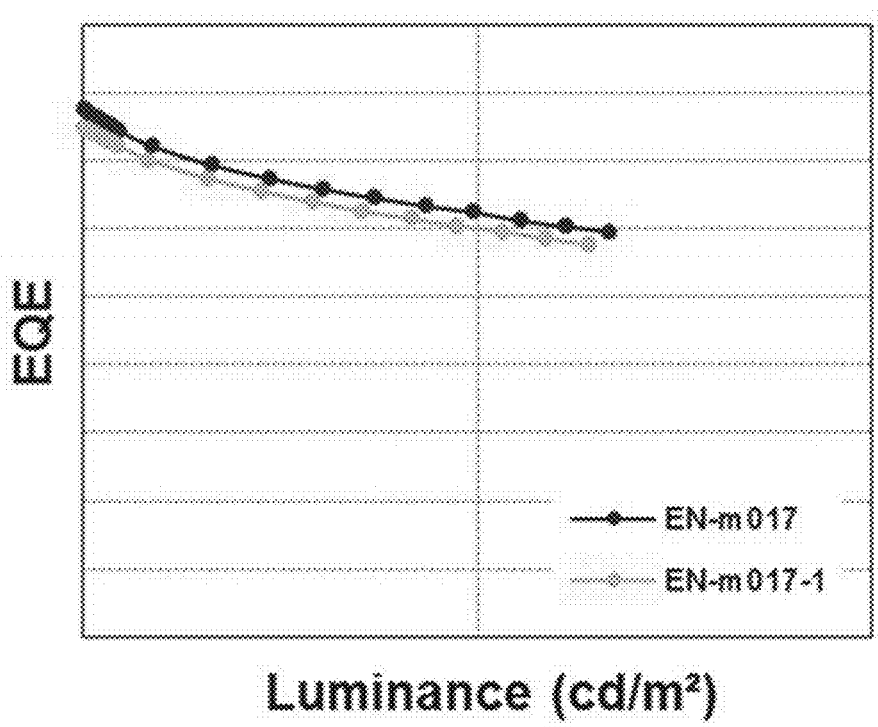
Figure 23:
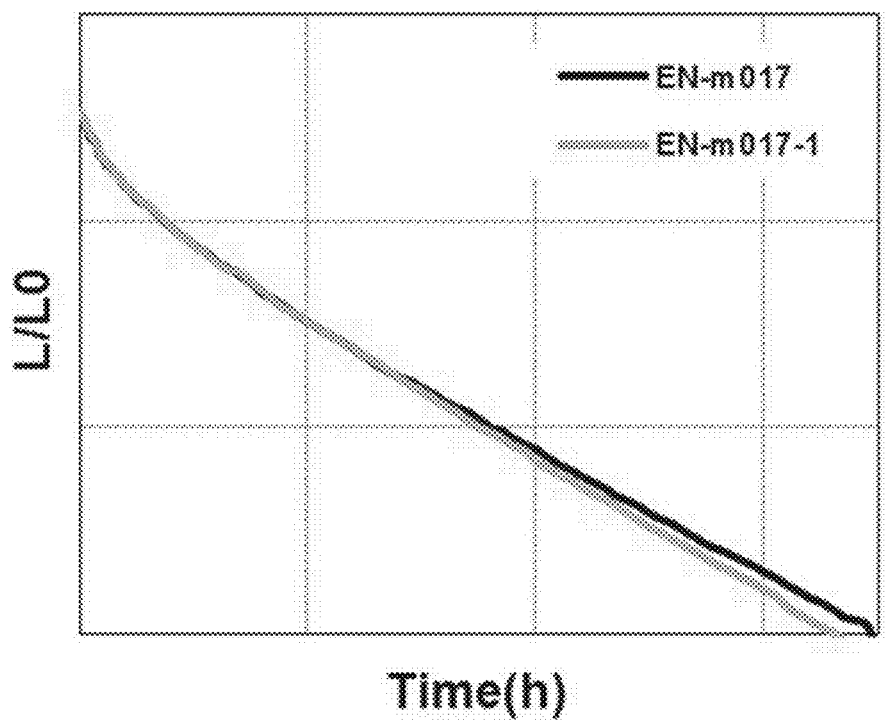
Figure 24:
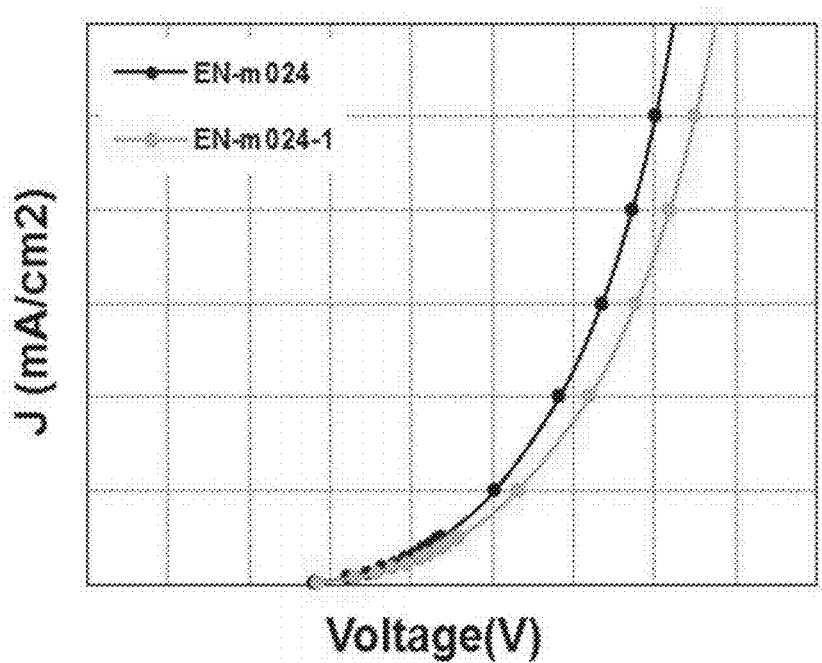
FIG. 24 to FIG. 27 are graphs depicting results of determining current density, current efficiency, external quantum efficiency (EQE), and lifespan of tandem organic light emitting diodes including organic compounds prepared in Example 6 and Comparative Example 6, respectively.
Figure 25:
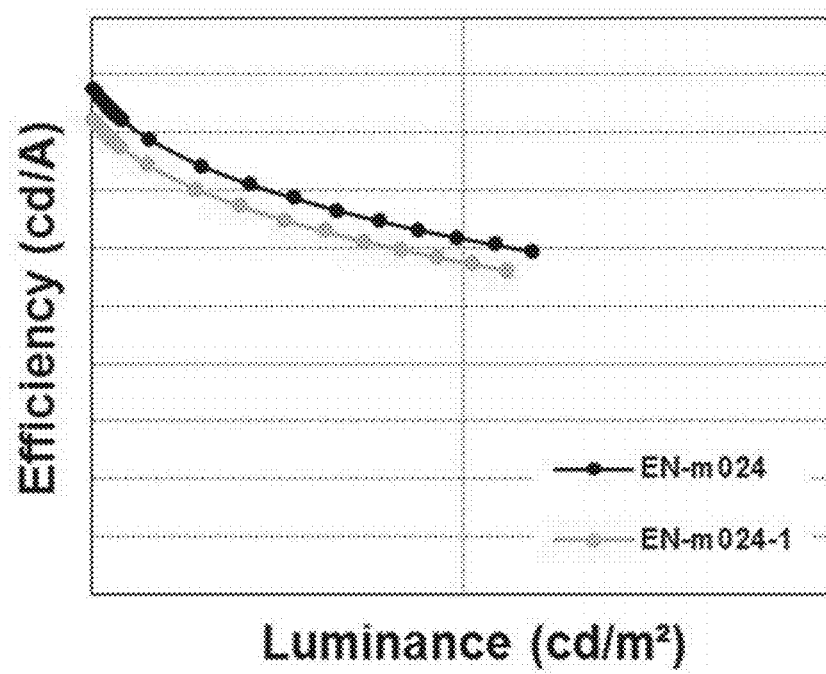
Figure 26:
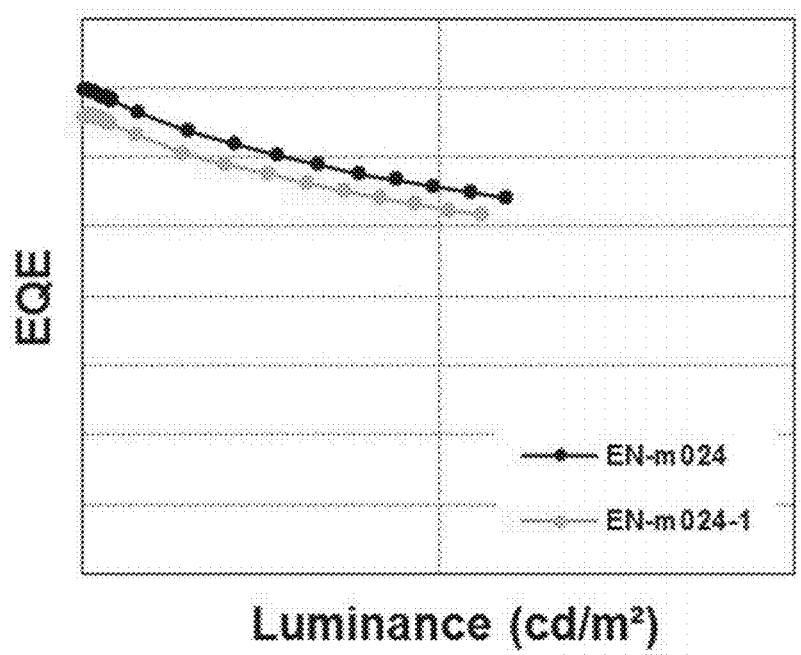
Figure 27:
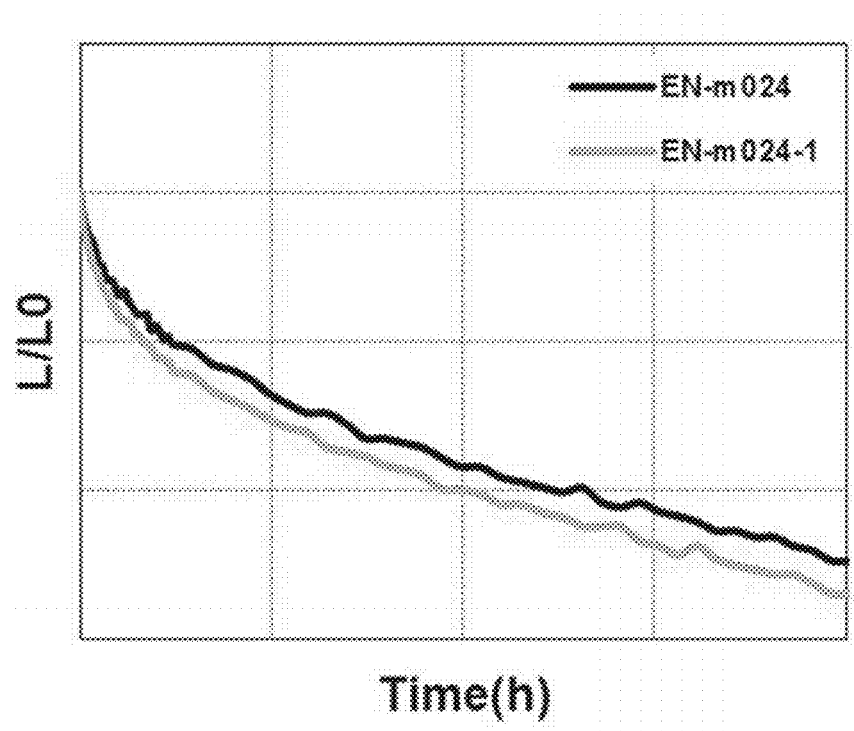

FIG. 3 is a schematic sectional view of an organic light emitting display according to one exemplary embodiment of the present disclosure.

Referring to FIG. 3, an organic light emitting display 300 according to this embodiment may include a substrate 301, an organic light emitting diode 400, and an encapsulation film 390 covering the organic light emitting diode 400. A driving thin film transistor Td acting as a driving device and the organic light emitting diode 400 connected to the driving thin film transistor Td are disposed on the substrate 301.

Although not shown in the drawings, the organic light emitting display further includes a gate line and a data line intersecting each other to define a pixel region, a power line extending parallel to one of the gate line and the data line and separated therefrom, a switching thin film transistor connected to the gate line and the data line, and a storage capacitor connected to the power line and one electrode of the switching thin film transistor on the substrate 301.

The driving thin film transistor Td is connected to the switching thin film transistor and includes a semiconductor layer 310, a gate electrode 330, a source electrode 352 and a drain electrode 354.

The semiconductor layer 310 is formed on the substrate 301 and may be formed of an oxide semiconductor material or polycrystalline silicon. When the semiconductor layer 310 is formed of the oxide semiconductor material, a light shielding pattern (not shown) may be formed under the semiconductor layer 310 to prevent light-induced degradation of the semiconductor layer 310 by blocking light from entering the semiconductor layer 310. Alternatively, the semiconductor layer 310 may be formed of polycrystalline silicon. In this alternative embodiment, both edges of the semiconductor layer 310 may be doped with impurities.

A gate insulation layer 320 including an insulating material may be formed over the substrate 301 to be disposed on the semiconductor layer 310. The gate insulation layer 320 may be formed of an inorganic insulating material, such as silicon oxide or silicon nitride.

The gate electrode 330 is formed of a conductive material such as a metal at a location on the gate insulation layer 320 corresponding to the center of the semiconductor layer 310. The gate electrode 330 is connected to the switching thin film transistor.

An interlayer insulation layer 340 is formed of an insulating material over the substrate 301 to be disposed on the gate electrode 330. The interlayer insulation layer 340 may be formed of an inorganic insulation material, such as silicon oxide or silicon nitride, or an organic insulation material, such as benzocyclobutene or photo-acryl.

The interlayer insulation layer 340 has first and second semiconductor layer contact holes 342, 344, which expose opposite sides of the semiconductor layer 310, respectively. The first and second semiconductor layer contact holes 342, 344 are disposed at opposite sides of the gate electrode 330 to be separated therefrom.

The source electrode 352 and the drain electrode 354 are formed of a conductive material and disposed on the interlayer insulation layer 340. The source electrode 352 and the drain electrode 354 are separated from each other around the gate electrode 330 and contact the opposite sides of the semiconductor layer 310 through the first and second semiconductor layer contact holes 342, 344, respectively. The source electrode 352 is connected to the power line (not shown).

The semiconductor layer 310, the gate electrode 330, the source electrode 352, and the drain electrode 354 constitute the driving thin film transistor Td. In this embodiment, the driving thin film transistor Td has a coplanar structure wherein the gate electrode 330, the source electrode 352 and the drain electrode 354 are disposed on the semiconductor layer 310.

Alternatively, the driving thin film transistor Td may have an inverted staggered structure wherein the gate electrode is disposed at a lower side of a semiconductor layer and the source electrode and the drain electrode are disposed at an upper side of the semiconductor layer. In this structure, the semiconductor layer may be formed of non-crystalline silicon. On the other hand, the switching thin film transistor (not shown) may have substantially the same structure as the driving thin film transistor Td.

The organic light emitting display 300 may include a color filter 360 that absorbs light emitted from the organic light emitting diode 400. For example, the color filter 360 can absorb red (R), green (G), blue (B) and white (W) light. In this case, each of color filter patterns adapted to absorb red, green and blue light may be separately formed in the corresponding pixel region to overlap an organic light emitting layer 430 of the organic light emitting diode 400, which emits light in a wavelength band to be absorbed by the corresponding color filter pattern. With the color filter 360, the organic light emitting display 300 can realize full-color display.

For example, when the organic light emitting display 300 is a bottom emission type, the color filter 360 for absorbing light may be disposed at an upper side of the interlayer insulation layer 340 that corresponds to the organic light emitting diode 400. In an alternative embodiment, in which the organic light emitting display 300 is a top emission type, the color filter may be disposed at an upper side of the organic light emitting diode 400, that is, an upper side of the second electrode 420. By way of example, the color filter 460 may have a thickness of 2 μm to 5 μm. In this embodiment, the organic light emitting diode 400 may be a white light emitting diode having a tandem structure, as shown in FIG. 1 to FIG. 2.

A protective layer 370 is formed to cover the driving thin film transistor Td. The protective layer 370 has a drain contact hole 372 that exposes the drain electrode 354.

A first electrode 410 is formed on the protective layer 370 to be separately disposed in each pixel region and is connected to the drain electrode 354 of the driving thin film transistor Td through the drain contact hole 372.

The first electrode 410 may be an anode and may be formed of a conductive material having a relatively high work function. For example, the first electrode 410 may be formed of a transparent conductive material, such as ITO, IZO or ZnO.

On the other hand, when the organic light emitting display 300 is a top emission type, a reflective electrode or a reflective layer may be further formed on a lower surface of the first electrode 410. For example, the reflective electrode or the reflective layer may be formed of one material selected from among aluminum (Al), silver (Ag), nickel (Ni), and aluminum-palladium-copper (APC) alloys.

A bank layer 380 may be formed on the protective layer 370 to cover an edge of the first electrode 410. The bank layer 380 exposes a central region of the first electrode 410 corresponding to the pixel region.

An organic light emitting layer 430 is formed on the first electrode 410. By way of example, the organic light emitting layer 430 may include at least two light emitting stacks as shown in FIG. 1 and FIG. 2 to form a tandem structure of the organic light emitting diode 400.

A second electrode 420 is formed on the organic light emitting layer 430 to be disposed above the substrate 301. The second electrode 420 is disposed over a display region and may be formed of a conductive material having a relatively low work function to be used as a cathode. For example, the second electrode 420 may be formed of one of aluminum (Al), magnesium (Mg), and an AlMg alloy.

The first electrode 410, the organic light emitting layer 430, and the second electrode 420 constitute the organic light emitting diode 400.

An encapsulation film 390 is formed on the second electrode 420 to prevent external moisture from entering the organic light emitting diode 400. Although not shown in the drawings, the encapsulation layer 390 may have a trilayer structure in which a first inorganic layer, a second organic layer and a third inorganic layer are sequentially stacked, without being limited thereto.

As described above, the organic compound according to the present disclosure has a phenanthroline moiety substituted with at least one aromatic ring. Since the organic compound has high thermal stability due to the presence of the aromatic ring-substituted phenanthroline moiety, when used in the organic light emitting diode 400, the organic compound can increase lifespan of the organic light emitting diode 400 while reducing driving voltage of the organic light emitting diode 400.

In addition, the organic compound according to the present disclosure has good electron transport properties due to the presence of the phenanthroline moiety. Further, nitrogen atoms of the phenanthroline moiety are bonded to the alkali metal or alkali earth metal compound, which is a dopant of the N-type charge generation layer, to form a gap state. As a result, a difference in energy level between the N-type charge generation layer and the P-type charge generation layer is reduced, whereby electron injection into the N-type charge generation layer can be facilitated while electron transfer from the N-type charge generation layer to the adjacent electron transport layer can be further improved.

Moreover, the organic compound having nitrogen atoms is combined with the alkali metal or alkali earth metal compound in the N-type charge generation layer, thereby preventing the alkali metal or alkali earth metal compound from diffusing into the P-type charge generation layer. As a result, reduction in lifespan of the organic light emitting diode can be prevented.

Next, the present disclosure will be described in more detail with reference to examples. However, it should be noted that these examples are provided for illustration only and should not be construed in any way as limiting the disclosure.

EXAMPLES

Preparative Example 1

Preparation of Compound EN-m002

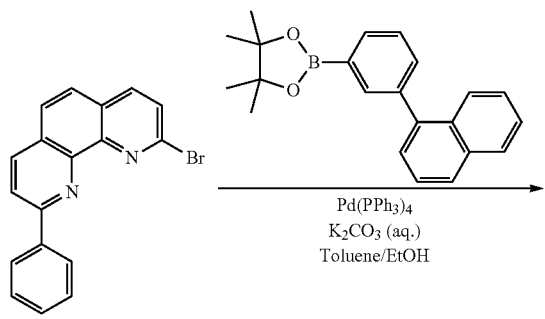

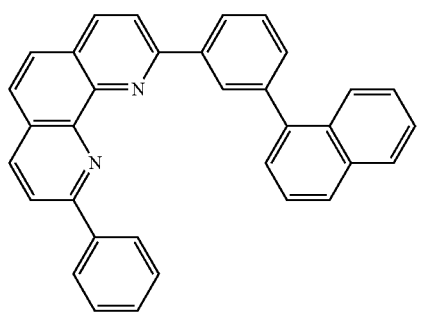

EN-m002

Into a flask under a nitrogen atmosphere, 4,4,5,5-tetramethyl-2-(3-(naphthalen-1-yl)phenyl)-1,3,2-dioxaborolane (5.10 g, 15.44 mmol), 2-bromo-9-phenyl-1,10-phenanthroline (4.64 g, 13.89 mmol), tetrakis(triphenylphosphine) palladium (0) (Pd(PPh$_3$)$_4$) (0.80 g, 0.69 mmol), 4M potassium carbonate aqueous solution (10 ml), toluene (30 ml), and ethanol (EtOH) (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m002 (5.49 g, yield: 86.3%).

Comparative Preparative Example 1

Preparation of Compound EN-m002-1

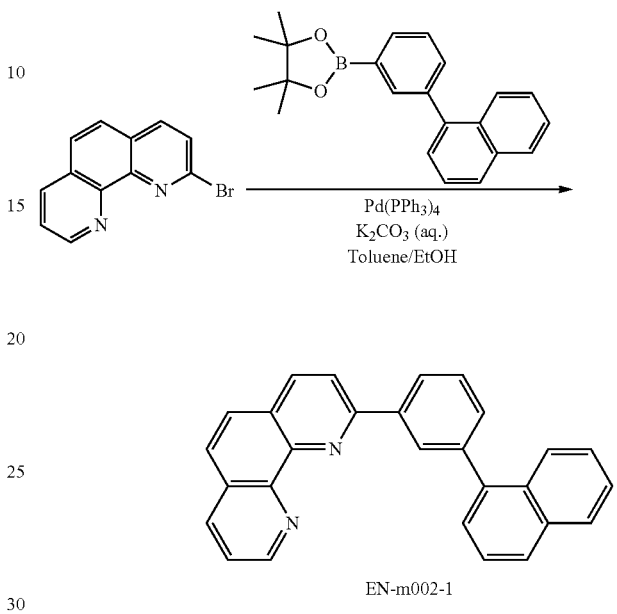

EN-m002-1

Into a flask under a nitrogen atmosphere, 4,4,5,5-tetramethyl-2-(3-(naphthalen-1-yl)phenyl)-1,3,2-dioxaborolane (6.00 g, 18.16 mmol), 2-bromo-1,10-phenanthroline (4.47 g, 17.26 mmol), tetrakis(triphenylphosphine) palladium (0) (Pd(PPh$_3$)$_4$) (0.99 g, 0.86 mmol), 4M potassium carbonate aqueous solution (10 ml), toluene (30 ml), and ethanol (EtOH) (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m002-1 (5.81 g, yield 88.0%).

Preparative Example 2

Preparation of Compound EN-m005

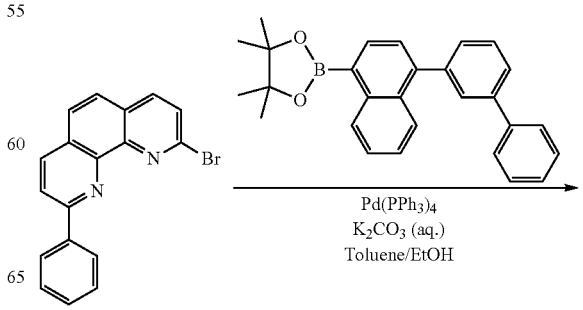

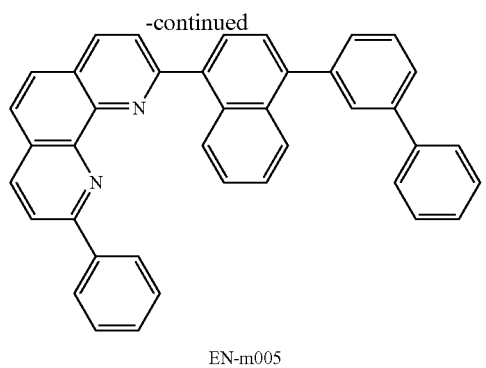

EN-m005

Into a flask under a nitrogen atmosphere, 4,4,5,5-tetramethyl-2-(1-3-(phenylen-1-yl)phenyl)naphthalen4-yl)-1,3,2-dioxaborolane (6.02 g, 14.81 mmol), 2-bromo-9-phenyl-1,10-phenanthroline (4.45 g, 13.33 mmol), tetrakis (triphenylphosphine) palladium (0) (Pd(PPh$_3$)$_4$) (0.77 g, 0.66 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m005 (5.22 g, yield: 73.4%).

Comparative Preparative Example 2

Preparation of Compound EN-m005-1

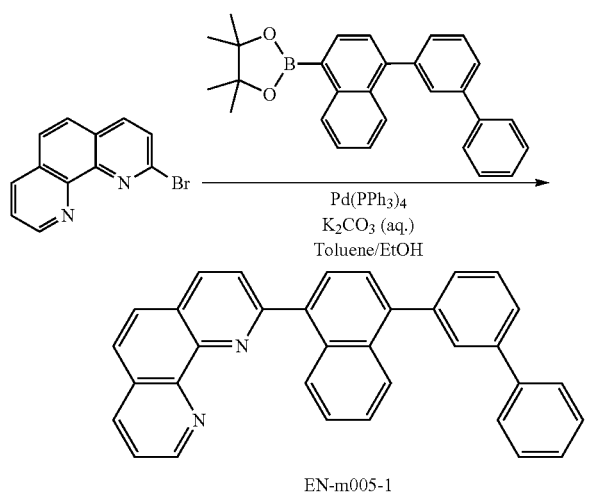

EN-m005-1

Into a flask under a nitrogen atmosphere, 4,4,5,5-tetramethyl-2-(1-3-(phenylen-1-yl)phenyl)naphthalen4-yl)-1,3,2-dioxaborolane (6.50 g, 15.99 mmol), 2-bromo-1,10-phenanthroline (3.52 g, 13.60 mmol), tetrakis (triphenylphosphine) palladium (0) (Pd(PPh$_3$)$_4$) (0.78 g, 0.68 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m005-1 (5.42 g, yield 86.7%).

Preparative Example 3

Preparation of Compound EN-m006

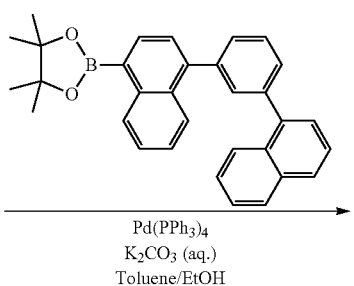

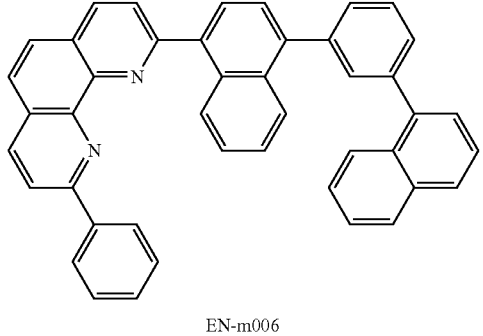

EN-m006

Into a flask under a nitrogen atmosphere, 4,4,5,5-tetramethyl-2-(1-(3-(naphthalen-1-yl)phenyl)naphthalen-4-yl)-1,3,2-dioxaborolane (6.00 g, 13.15 mmol), 2-bromo-9-phenyl-1,10-phenanthroline (3.95 g, 11.83 mmol), tetrakis (triphenylphosphine) palladium (0) (Pd(PPh$_3$)$_4$) (0.68 g, 0.59 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m006 (5.66 g, yield 81.9%).

Comparative Preparative Example 3

Preparation of Compound EN-m006-1

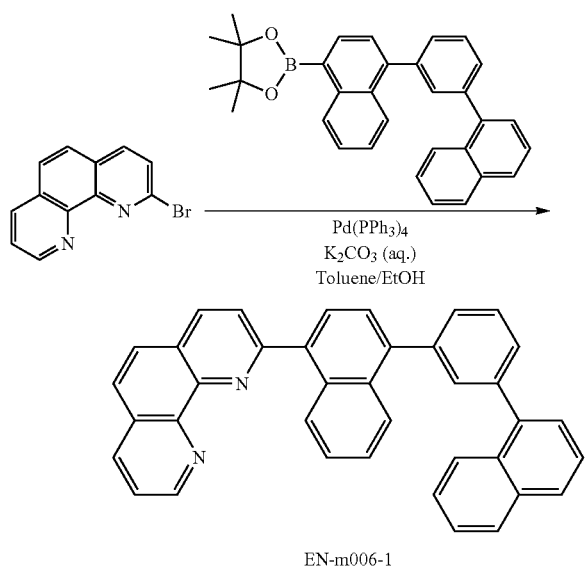

EN-m006-1

Into a flask under a nitrogen atmosphere, 4,4,5,5-tetramethyl-2-(1-(3-(naphthalen-1-yl)phenyl)naphthalen-4-yl)-1,3,2-dioxaborolane (6.50 g, 14.24 mmol), 2-bromo-1,10-phenanthroline (3.32 g, 12.81 mmol), tetrakis(triphenylphosphine) palladium (0) (Pd(PPh$_3$)$_4$) (0.74 g, 0.64 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m006-1 (5.20 g, yield: 79.8%).

Preparative Example 4

Preparation of Compound EN-m008

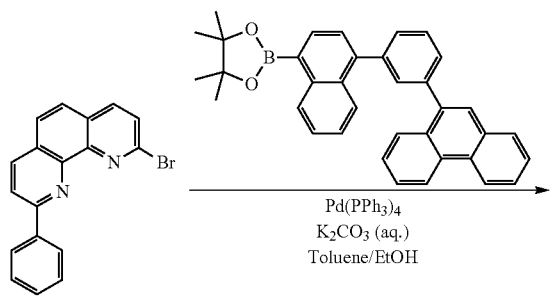

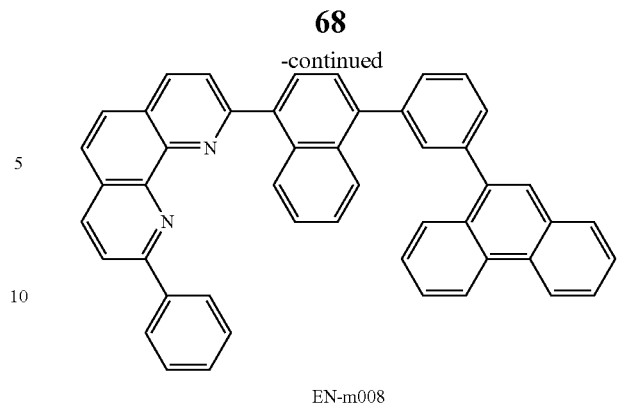

EN-m008

Into a flask under a nitrogen atmosphere, 4,4,5,5-tetramethyl-2-(1-(3-(phenanthren-10-yl)phenyl)naphthalen-4-yl)-1,3,2-dioxaborolane (7.00 g, 13.83 mmol), 2-bromo-9-phenyl-1,10-phenanthroline (4.16 g, 12.44 mmol), tetrakis(triphenylphosphine) palladium (0) (Pd(PPh$_3$)$_4$) (0.72 g, 0.62 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting was performed by column chromatography using methylene chloride (MC) and hexane as an eluent, followed by recrystallization from MC, thereby obtaining Compound EN-m008 (6.12 g, yield: 77.5%).

Comparative Preparative Example 4

Preparation of Compound EN-m008-1

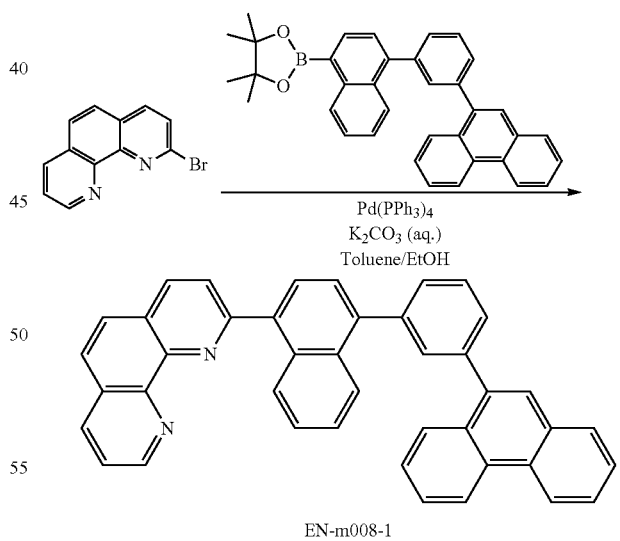

EN-m008-1

Into a flask under a nitrogen atmosphere, 4,4,5,5-tetramethyl-2-(1-(3-(phenanthren-10-yl)phenyl)naphthalen-4-yl)-1,3,2-dioxaborolane (6.80 g, 13.43 mmol), 2-bromo-1,10-phenanthroline (3.13 g, 12.09 mmol), tetrakis(triphenylphosphine) palladium (0) (Pd(PPh$_3$)$_4$) (0.69 g, 0.60 mmol), 4M potassium carbonate aqueous solution (10 ml), toluene (30 ml), and ethanol (10 ml) were placed, followed by stirring under reflux for 12 hours. After completion of reaction, H₂O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m008-1 (5.36 g, yield: 79.5%).

Preparative Example 5

Preparation of Compound EN-m017

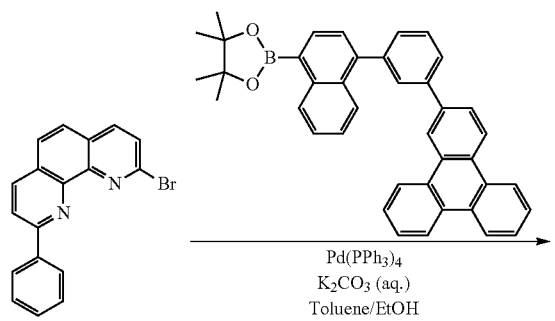

EN-m017

Into a flask under a nitrogen atmosphere, 4,4,5,5-tetramethyl-2-(1-(3-(triphenylene-2-yl)phenyl)naphthalen-4-yl)-1,3,2-dioxaborolane (7.52 g, 13.51 mmol), 2-bromo-9-phenyl-1,10-phenanthroline (4.06 g, 12.17 mmol), tetrakis(triphenylphosphine) palladium (0) (Pd(PPh₃)₄) (0.70 g, 0.61 mmol), 4M potassium carbonate aqueous solution (10 ml), toluene (30 ml), and ethanol (10 ml) were placed, followed by stirring under reflux for 12 hours. After completion of reaction, H₂O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m017 (6.98 g, yield: 83.7%).

Comparative Preparative Example 5

Preparation of Compound EN-m017-1

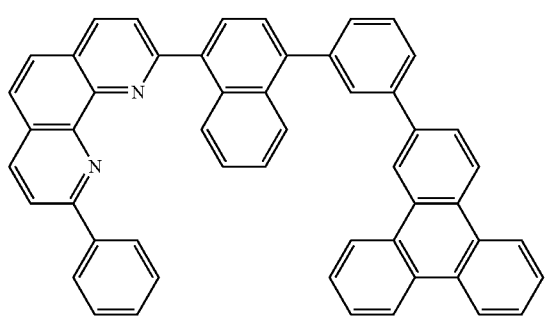

EN-m017-1

Into a flask under a nitrogen atmosphere, 4,4,5,5-tetramethyl-2-(1-(3-(triphenylene-2-yl)phenyl)naphthalen-4-yl)-1,3,2-dioxaborolane (7.30 g, 13.11 mmol), 2-bromo-1,10-phenanthroline (3.06 g, 11.80 mmol), tetrakis(triphenylphosphine) palladium (0) (Pd(PPh₃)₄) (0.68 g, 0.59 mmol), 4M potassium carbonate aqueous solution (10 ml), toluene (30 ml), and ethanol (10 ml) were placed, followed by stirring under reflux for 12 hours. After completion of reaction, H₂O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m017-1 (6.05 g, yield 84.3%).

Preparative Example 6

Preparation of Compound EN-m024

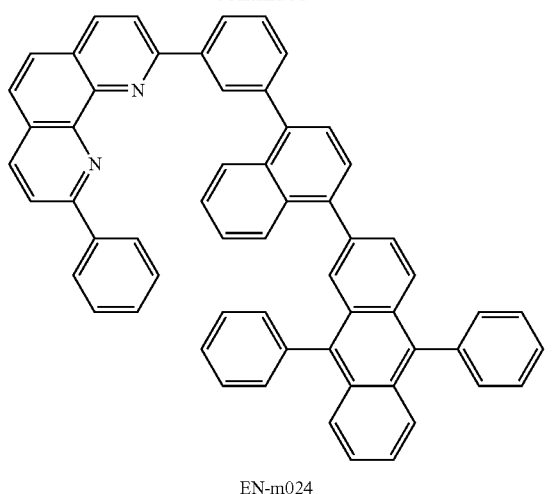

EN-m024

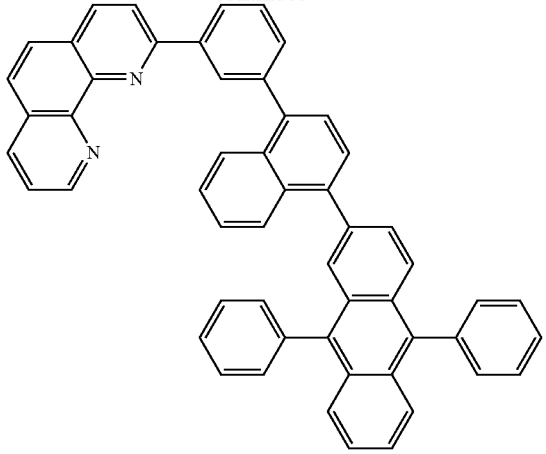

EN-m024-1

Into a flask under a nitrogen atmosphere, 4,4,5,5-tetramethyl-2-(3-(1-(9,10-diphenylanthracene-2-yl)naphthalen-4-yl)phenyl)-1,3,2-dioxaborolane (8.81 g, 13.38 mmol), 2-bromo-9-phenyl-1,10-phenanthroline (4.02 g, 12.04 mmol), tetrakis(triphenylphosphine) palladium (0) (Pd (PPh$_3$)$_4$) (0.70 g, 0.60 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m024 (7.42 g, yield: 78.3%).

Comparative Preparative Example 6

Preparation of Compound EN-m4024-1

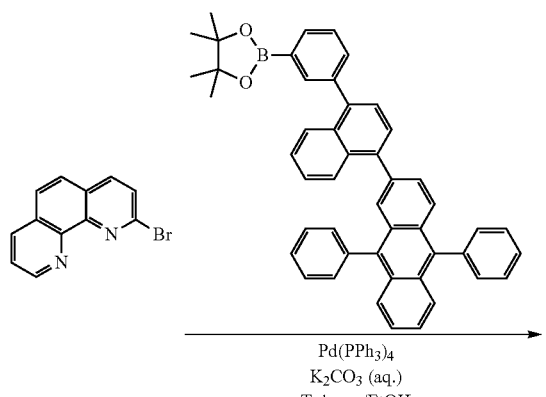

Into a flask under a nitrogen atmosphere, 4,4,5,5-tetramethyl-2-(3-(1-(9,10-diphenylanthracene-2-yl)naphthalen-4-yl)phenyl)-1,3,2-dioxaborolane (8.50 g, 12.90 mmol), 2-bromo-1,10-phenanthroline (2.84 g, 10.96 mmol), tetrakis (triphenylphosphine) palladium (0) (Pd(PPh$_3$)$_4$) (0.63 g, 0.55 mmol), 4M potassium carbonate aqueous solution (10 ml), toluene (30 ml), and ethanol (10 ml) were placed, followed by stirring under reflux for 12 hours. After completion of reaction, H$_2$O (50 ml) was added, followed by filtration under reduced pressure subsequent to stirring for 3 hours, and then separation of the resulting product was performed by column chromatography using methylene chloride (MC) and hexane as an eluent, followed by recrystallization from MC, thereby obtaining Compound EN-m024-1 (5.94 g, yield: 76.2%).

Experimental Example 1

Evaluation of Thermal Stability and Electron Transfer Properties

Each of the organic compounds prepared in Preparative Examples 1 to 6 and Comparative Preparative Examples 1 to 6 was evaluated as to thermal stability and electron transfer properties. In thermal analysis, thermogravimetric analysis (TGA) and differential scanning calorimetry (DSC) were carried out to determine the decomposition temperature (1%, 5%) and glass transition temperature (Tg) of each organic compound, respectively. In evaluation of electron transfer properties, electron affinity (EA), electron reorganization energy ($\lambda_{electron}$), and electron/hole rate constant ratio (ket(e)/ket(h)) of each organic compound were calculated based on density functional theory (B3LYP/6-31G*). Results are shown in Table 1.

TABLE 1

| | Thermal analysis (° C.) | | | Simulation analysis | | |
|---|---|---|---|---|---|---|
| | $T_a$ (1%) | $T_a$ (5%) | $T_g$ | Electron affinity | $\lambda_{electron}$ | ket(e)/ket(h) |
| EN-m002 | 392 | 443 | 121 | 0.62 | 0.25 | 0.70 |
| EN-m002-1 | 368 | 428 | 112 | 0.47 | 0.29 | 0.79 |
| EN-m005 | 412 | 457 | 115 | 0.60 | 0.26 | 0.28 |
| EN-m005-1 | 387 | 429 | 105 | 0.52 | 0.35 | 0.21 |

TABLE 1-continued

| | Thermal analysis (° C.) | | | Simulation analysis | | |
|---|---|---|---|---|---|---|
| | $T_a$ (1%) | $T_a$ (5%) | $T_a$ | Electron affinity | $\lambda_{electron}$ | ket(e)/ket(h) |
| EN-m006 | 426 | 471 | 125 | 0.77 | 0.23 | 0.64 |
| EN-m006-1 | 402 | 458 | 116 | 0.70 | 0.28 | 0.47 |
| EN-m008 | 445 | 487 | 137 | 0.82 | 0.25 | 0.35 |
| EN-m008-1 | 424 | 460 | 127 | 0.54 | 0.34 | 0.26 |
| EN-m017 | 454 | 497 | 156 | 0.88 | 0.30 | 0.46 |
| EN-m017-1 | 432 | 473 | 132 | 0.56 | 0.07 | 0.36 |
| EN-m024 | 466 | 506 | 146 | 0.93 | 0.30 | 0.30 |
| EN-m024-1 | 440 | 478 | 140 | 0.85 | 0.34 | 0.30 |

As shown in Table 1, the organic compound represented by Formula 1 had a higher EA value than the compounds having phenanthroline not substituted with phenyl, and thus could easily receive electrons. Particularly, a material for an N-type charge generation layer (n-CGL) needs to be able to efficiently transfer electrons from a P-type charge generation layer (p-CGL) to an electron transport layer (ETL). The organic compound having phenyl-substituted phenanthroline had a reduced $\lambda_{electron}$ value and an increased ket(e)/ket(h) value and thus advantageously exhibited high anionic stability and good electron transfer properties. In addition, it was confirmed that the organic compound represented by Formula 1 had higher decomposition temperature and glass transition temperature and thus better thermal stability than the compounds having phenanthroline not substituted with phenyl.

Example 1

Fabrication of Tandem Organic Light Emitting Diode

In a vacuum chamber at a pressure of $5 \times 10^{-8}$ to $7 \times 10^{-8}$ torr, a tandem organic light emitting diode was fabricated by sequentially depositing the following layers on an indium-tin-oxide (ITO) substrate:

A hole injection layer (NPD-based host doped with 10 wt % of F4-TCNQ; 100 Å), a first hole transport layer (NPD-based compound; 1200 Å), a first light emitting material layer (blue light emitting material layer; anthracene-based host doped with 4 wt % of pyrene dopant; 200 Å), a first electron transport layer (1,3,5-tri[(3-pyridyl)-phen-3-yl]benzene (TmPyPB)-based compound; 100 Å), a first N-type charge generation layer (EN-m002 doped with 2 wt % of Li; 100 Å), a first P-type charge generation layer (NPD-based host doped with 10 wt % of F4-TCNQ; 200 Å), a second hole transport layer (NPD-based compound; 200 Å), a second light emitting material layer (yellow light emitting material layer; CBP-based host doped with Ir complex; 200 Å), a second electron transport layer (Alq3), a second N-type charge generation layer (EN-m002 doped with 2 wt % of Li; 100 Å), a second P-type charge generation layer (NPD-based host doped with 10 wt % of F4-TCNQ; 200 Å), a third hole transport layer (NPD-based compound; 200 Å), a third light emitting material layer (blue light emitting material layer; anthracene-based host doped with 4 wt % of pyrene dopant; 200 Å), a third electron transport layer (TmPyPB-based compound; 100 Å), an electron injection layer (LiF, 10 Å), and a cathode (aluminum; 2000 Å).

Comparative Example 1

Fabrication of Tandem Organic Light Emitting Diode

A tandem organic light emitting diode was fabricated in the same manner as in Example 1 except that, as a host for the first and second N-type charge generation layers, EN-m002-1 prepared in Comparative Preparative Example 1 was used instead of EN-m002.

Example 2

Fabrication of Tandem Organic Light Emitting Diode

A tandem organic light emitting diode was fabricated in the same manner as in Example 1 except that, as a host for the first and second N-type charge generation layers, EN-m005 prepared in Preparative Example 2 was used instead of EN-m002.

Comparative Example 2

Fabrication of Tandem Organic Light Emitting Diode

A tandem organic light emitting diode was fabricated in the same manner as in Example 1 except that, as a host for the first and second N-type charge generation layers, EN-m005-1 prepared in Comparative Preparative Example 2 was used instead of EN-m002.

Example 3

Fabrication of Tandem Organic Light Emitting Diode

A tandem organic light emitting diode was fabricated in the same manner as in Example 1 except that, as a host for the first and second N-type charge generation layers, EN-m006 prepared in Preparative Example 3 was used instead of EN-m002.

Comparative Example 3

Fabrication of Organic Light Emitting Diode with Tandem Structure

A tandem organic light emitting diode was fabricated in the same manner as in Example 1 except that, as a host for the first and second N-type charge generation layers, EN-m006-1 prepared in Comparative Preparative Example 3 was used instead of EN-m002.

Example 4

Fabrication of Organic Light Emitting Diode with Tandem Structure

A tandem organic light emitting diode was fabricated in the same manner as in Example 1 except that, as a host for the first and second N-type charge generation layers, EN-m008 prepared in Preparative Example 4 was used instead of EN-m002.

Comparative Example 4

Fabrication of Organic Light Emitting Diode with Tandem Structure

A tandem organic light emitting diode was fabricated in the same manner as in Example 1 except that, as a host for the first and second N-type charge generation layers, EN-m008-1 prepared in Comparative Preparative Example 4 was used instead of EN-m002.

Example 5

Fabrication of Organic Light Emitting Diode with Tandem Structure

A tandem organic light emitting diode was fabricated in the same manner as in Example 1 except that, as a host for the first and second N-type charge generation layers, EN-m017 prepared in Preparative Example 5 was used instead of EN-m002.

Comparative Example 5

Fabrication of Organic Light Emitting Diode with Tandem Structure

A tandem organic light emitting diode was fabricated in the same manner as in Example 1 except that, as a host for the first and second N-type charge generation layers, EN-m017-1 prepared in Comparative Preparative Example 5 was used instead of EN-m002.

Example 6

Fabrication of Organic Light Emitting Diode with Tandem Structure

A tandem organic light emitting diode was fabricated in the same manner as in Example 1 except that, as a host for the first and second N-type charge generation layers, EN-m024 prepared in Preparative Example 6 was used instead of EN-m002.

Comparative Example 6

Fabrication of Organic Light Emitting Diode with Tandem Structure

A tandem organic light emitting diode was fabricated in the same manner as in Example 1 except that, as a host for the first and second N-type charge generation layers, EN-m024-1 prepared in Comparative Preparative Example 6 was used instead of EN-m002.

Experimental Example 2

Evaluation of Characteristics of Organic Light Emitting Diode

Operation characteristics of the tandem organic light emitting diodes fabricated in Examples 1 to 6 and Comparative Examples 1 to 6 were evaluated.

FIG. 4 to FIG. 7 show voltage-current density, luminance-current efficiency, luminance-external quantum efficiency (EQE), and lifespan of the organic light emitting diodes fabricated in Example 1 and Comparative Example 1. The organic light emitting diode of Example 1 had efficiency values higher or equivalent to those of the organic light emitting diode of Comparative Example 1 (current efficiency: increased by 3%, EQE: increased by 3%). In addition, the organic light emitting diode of Example 1 was reduced by 0.17 V in driving voltage and increased by 5% in lifespan, as compared with the organic light emitting diode of Comparative Example 1.

FIG. 8 to FIG. 11 show voltage-current density, luminance-current efficiency, luminance-external quantum efficiency (EQE), and lifespan of the organic light emitting diodes fabricated in Example 2 and Comparative Example 2. The organic light emitting diode of Example 2 had efficiency values higher or equivalent to those of the organic light emitting diode of Comparative Example 2 (current efficiency: increased by 1%, EQE: equivalent level). In addition, the organic light emitting diode of Example 2 was reduced by 0.19 V in driving voltage and was comparable in lifespan, as compared with the organic light emitting diode of Comparative Example 1.

FIG. 12 to FIG. 15 show voltage-current density, luminance-current efficiency, luminance-external quantum efficiency (EQE), and lifespan of the organic light emitting diodes fabricated in Example 3 and Comparative Example 3. The organic light emitting diode of Example 3 had efficiency values higher or equivalent to those of the organic light emitting diode of Comparative Example 3 (current efficiency: increased by 1%, EQE: increased by 5%). In addition, the organic light emitting diode of Example 3 was reduced by 0.79 V in driving voltage and increased by 22% in lifespan, as compared with the organic light emitting diode of Comparative Example 3.

FIG. 16 to FIG. 19 show voltage-current density, luminance-current efficiency, luminance-external quantum efficiency (EQE), and lifespan of the organic light emitting diodes fabricated in Example 4 and Comparative Example 4. The organic light emitting diode of Example 4 had efficiency values higher or equivalent to those of the organic light emitting diode of Comparative Example 4 (current efficiency: increased by 1%, EQE: equivalent level). In addition, the organic light emitting diode of Example 4 was reduced by 0.34 V in driving voltage and increased by 9% in lifespan, as compared with the organic light emitting diode of Comparative Example 4.

FIG. 20 to FIG. 23 show voltage-current density, luminance-current efficiency, luminance-external quantum efficiency (EQE), and lifespan of the organic light emitting diodes fabricated in Example 5 and Comparative Example 5. The organic light emitting diode of Example 5 had efficiency values higher or equivalent to those of the organic light emitting diode of Comparative Example 5 (current efficiency: increased by 2%, EQE: increased by 1%). In addition, the organic light emitting diode of Example 4 was reduced by 0.30 V in driving voltage and increased by 2% in lifespan, as compared with the organic light emitting diode of Comparative Example 5.

FIG. 24 to FIG. 27 show voltage-current density, luminance-current efficiency, luminance-external quantum efficiency (EQE), and lifespan of the organic light emitting diodes fabricated in Example 6 and Comparative Example 6. The organic light emitting diode of Example 5 had efficiency values higher or equivalent to those of the organic light emitting diode of Comparative Example 6 (current efficiency: increased by 1%, EQE: increased by 1%). In addition, the organic light emitting diode of Example 4 was reduced by 0.14 V in driving voltage and increased by 8% in lifespan, as compared with the organic light emitting diode of Comparative Example 6.

From the results of Experimental Example 2, it can be seen that the organic compound represented by Formula 1, that is, the organic compound having a phenanthroline moiety substituted with a phenyl group, has a driving voltage lower than or equal to that of an organic compound having a phenanthroline moiety not substituted with a phenyl group, and has current efficiency and external quantum efficiency higher than or equal to those of an organic compound having a phenanthroline moiety not substituted with a phenyl group. In particular, it was confirmed that introduction of a phenyl group into the organic compound could allow improvement in thermal stability, electron transfer properties, and lifespan of an organic light emitting diode.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic light emitting diode, comprising:
a first electrode and a second electrode facing each other;
a first light emitting stack interposed between the first electrode and the second electrode and comprising a first light emitting material layer and an electron transport layer;
a second light emitting stack interposed between the first light emitting stack and the second electrode and comprising a second light emitting material layer; and
a first charge generation layer interposed between the first light emitting stack and the second light emitting stack,
wherein at least one of the electron transport layer and the first charge generation layer comprises an N-type charge generation layer and a P-type charge generation layer, the N-type charge generation layer comprising an organic compound selected from one of the following formulae:

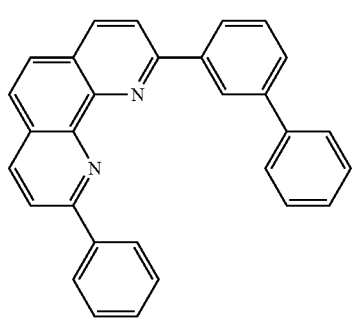

EN-m001

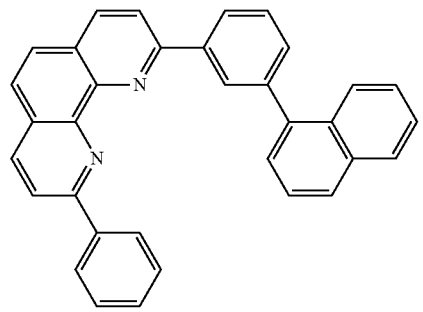

En-m002

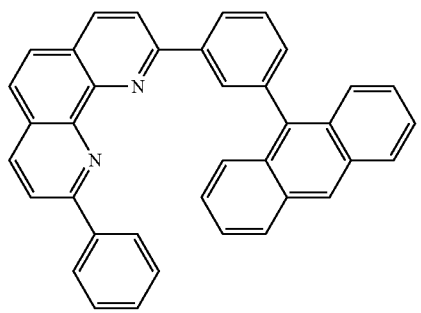

EN-m003

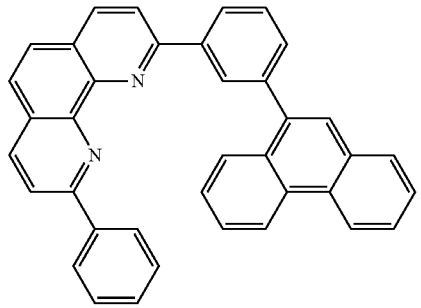

EN-m004

EN-m005

EN-m006
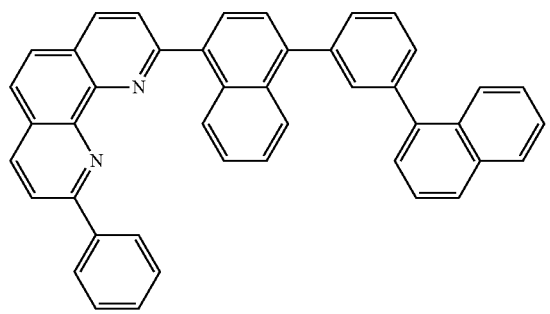
EN-m007
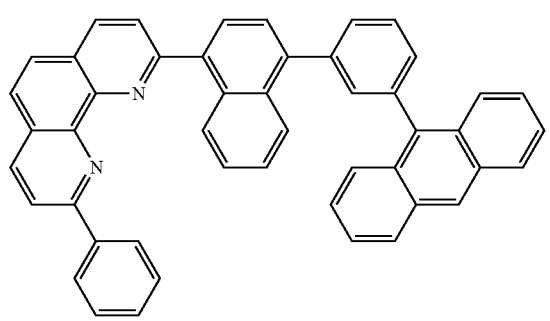
EN-m008
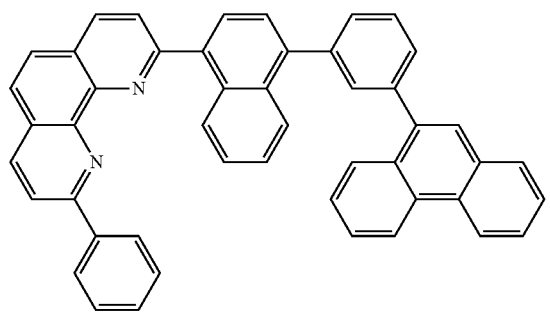
EN-m009
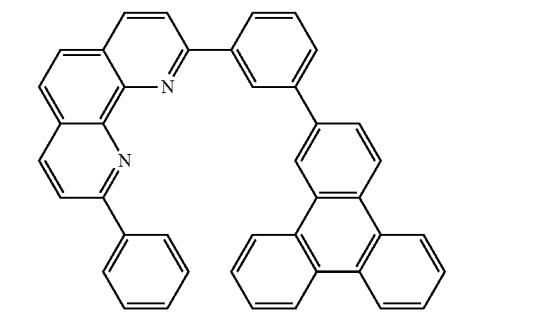
EN-m010
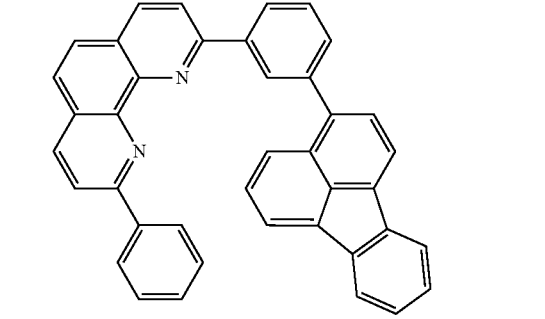
EN-m012
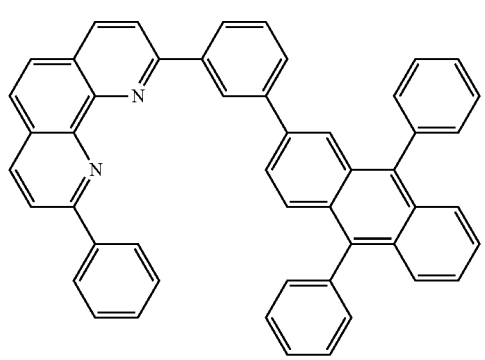
EN-m013
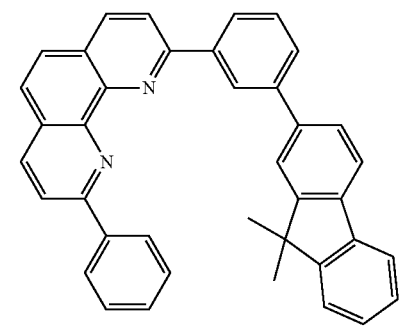
EN-m014
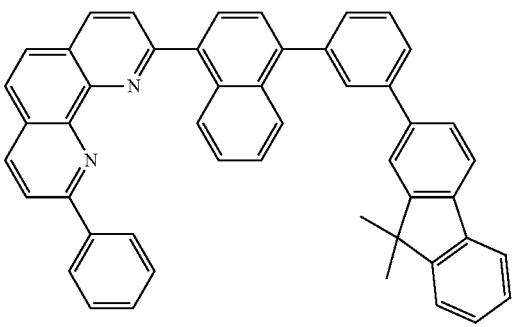
EN-m015
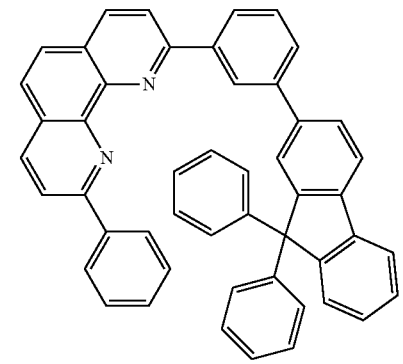

EN-m016
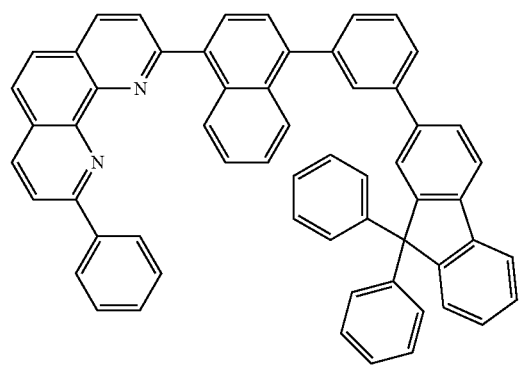
EN-m021
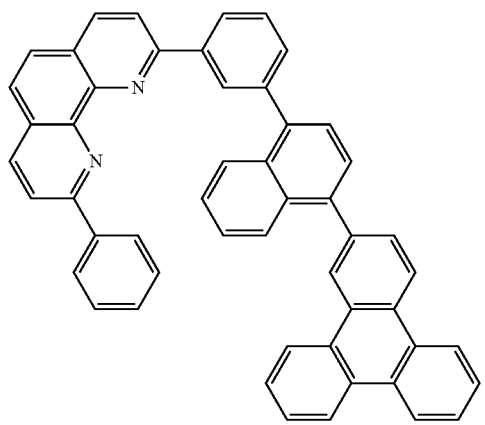
EN-m017
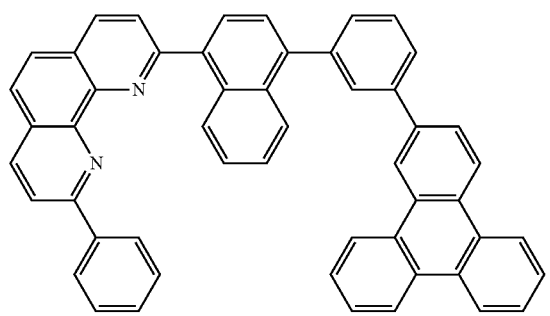
EN-m022
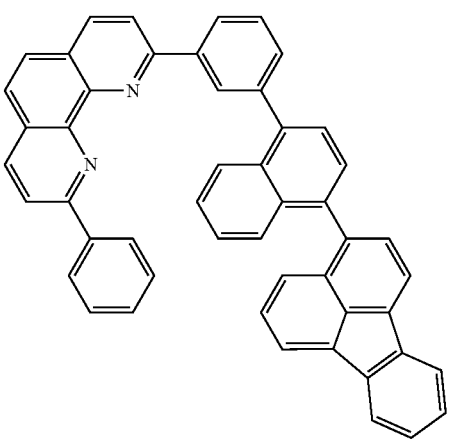
EN-m018
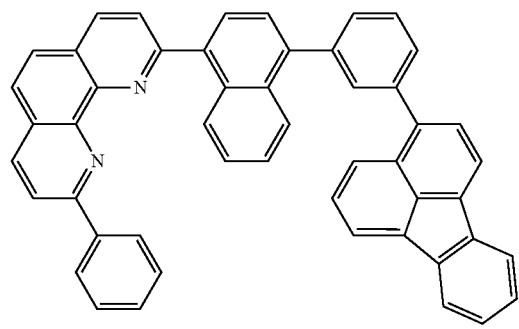
EN-m020
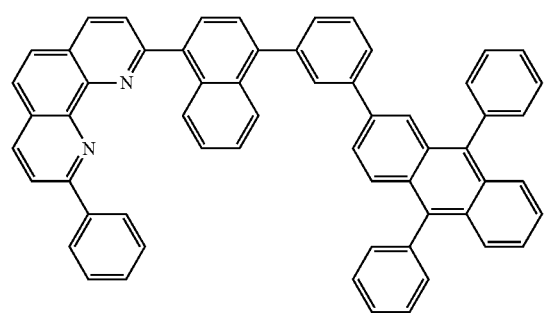
EN-m024
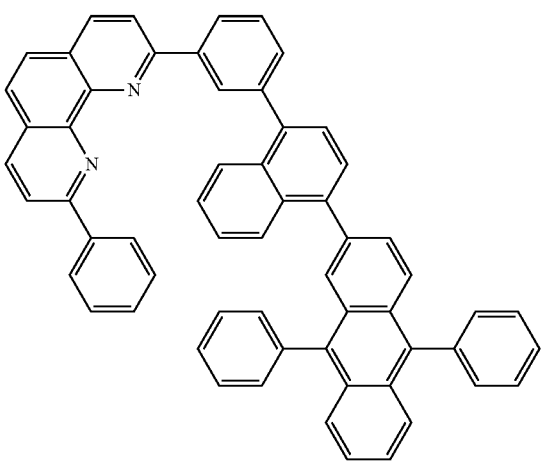

-continued
EN-m025
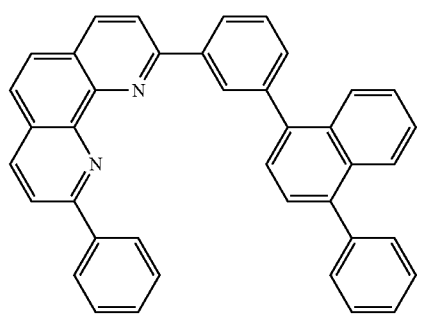
EN-m026
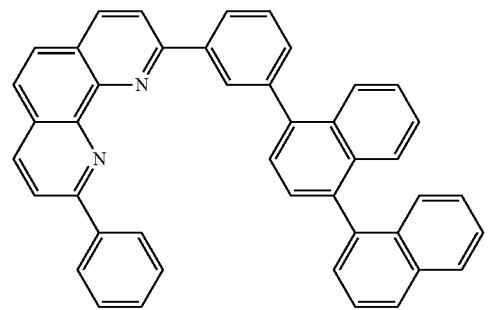
EN-m027
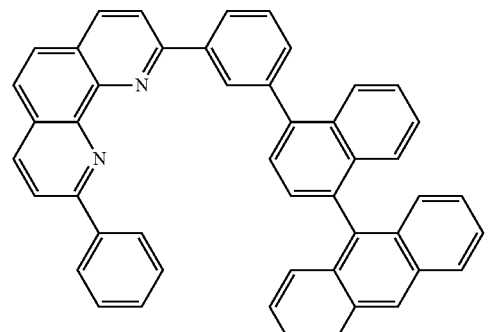
EN-m028
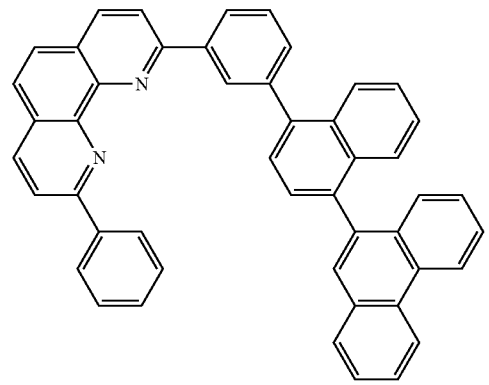
-continued
EN-m029
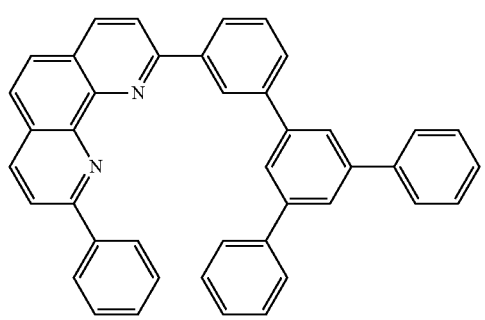
EN-m030
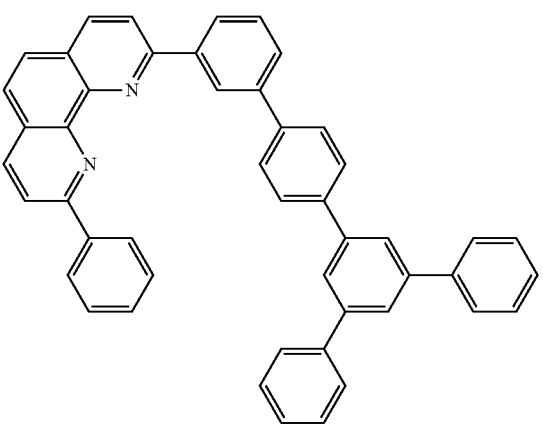
EN-m031
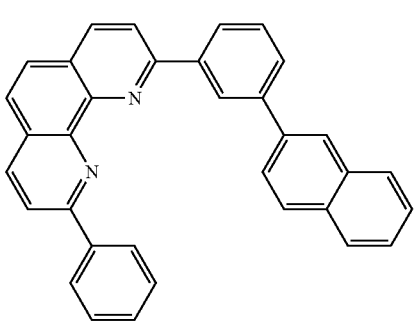
EN-m032
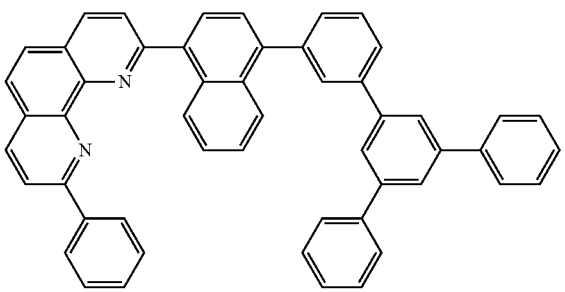

EN-m033
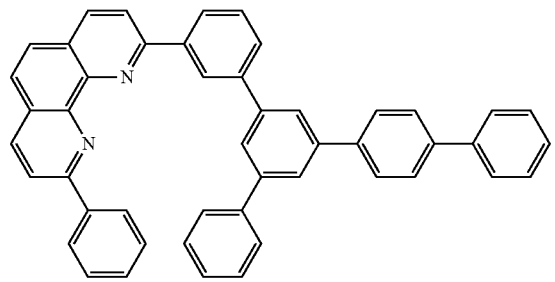
EN-m034
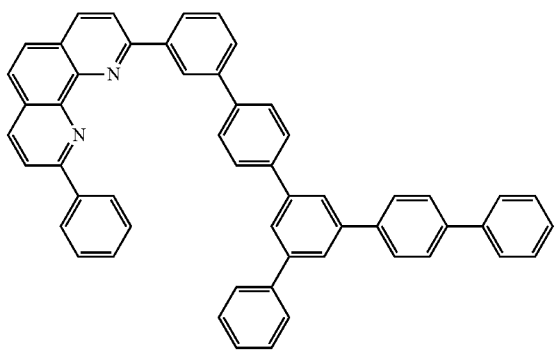
EN-m035
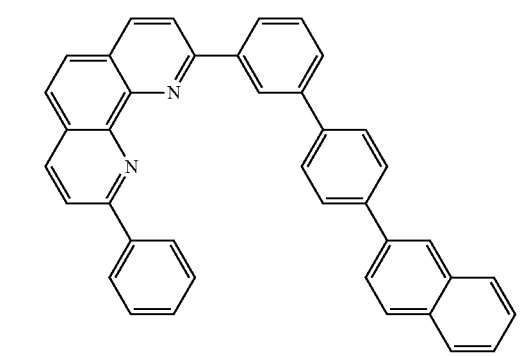
EN-m036
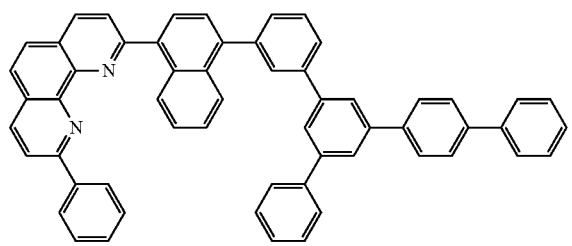
EN-m037
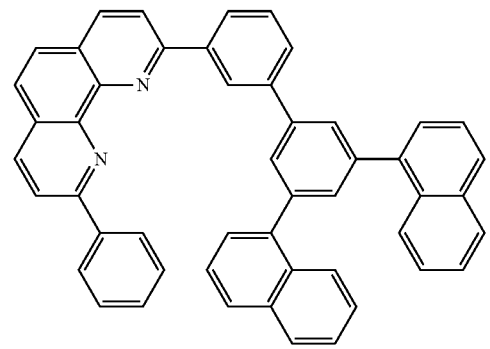
EN-m038
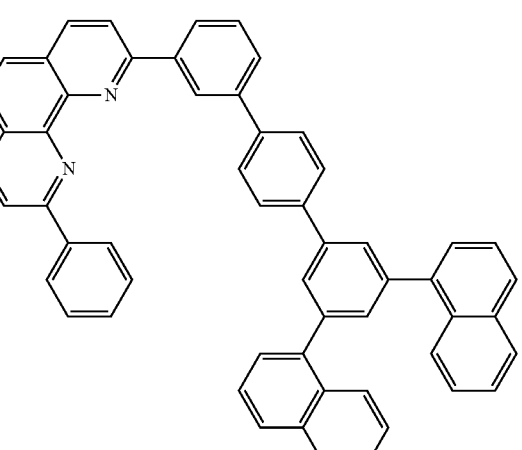
EN-m039
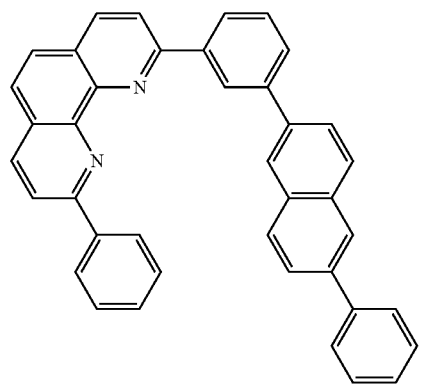
EN-m040
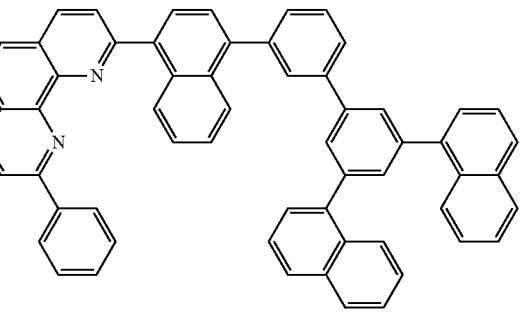

EN-m041
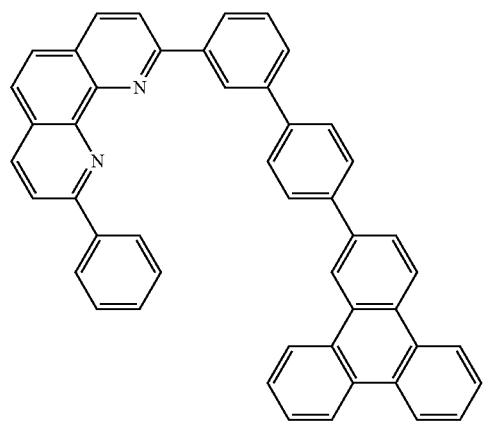
EN-m045
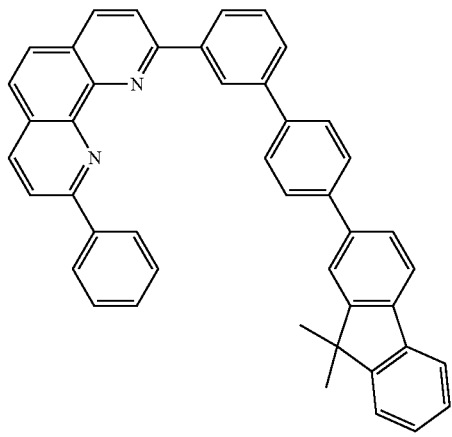
EN-m042
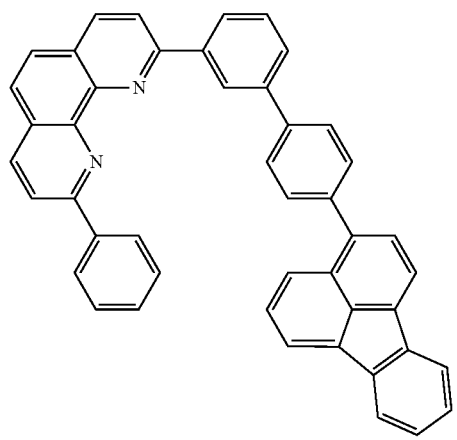
EN-m046
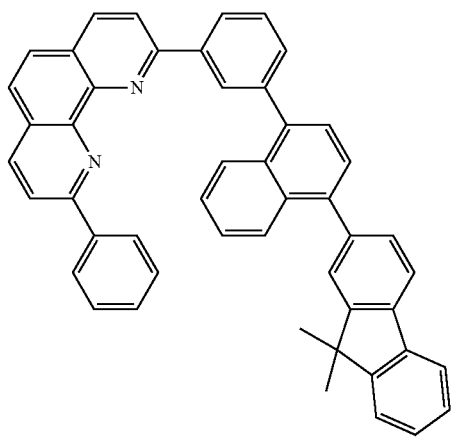
EN-m044
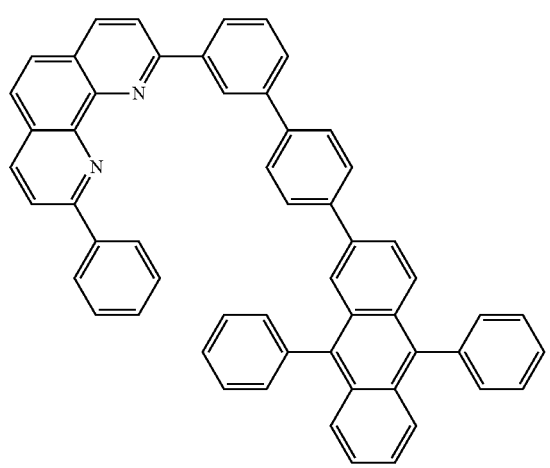
EN-m047
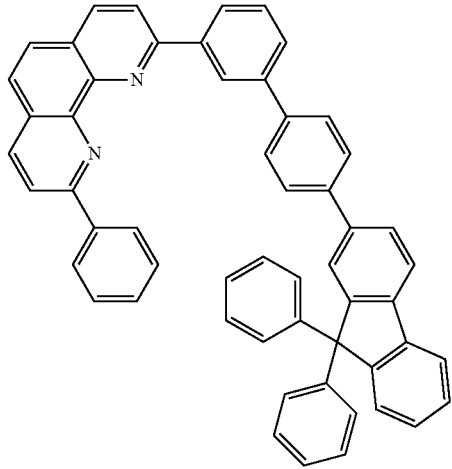

EN-m048
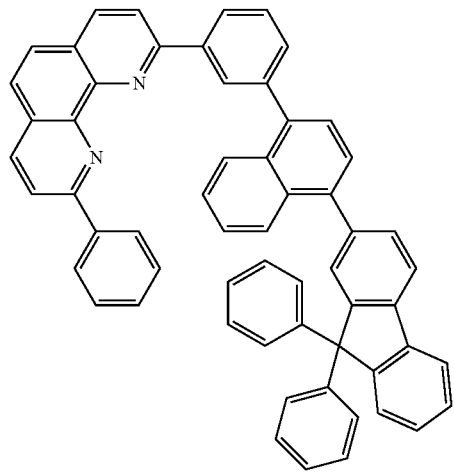
EN-m049
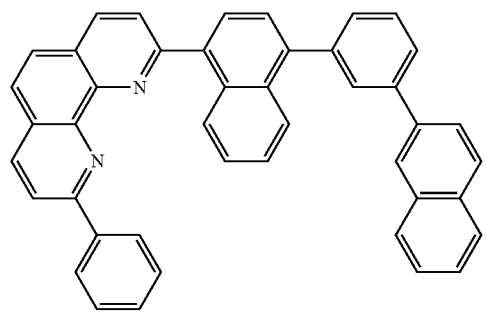
EN-m050
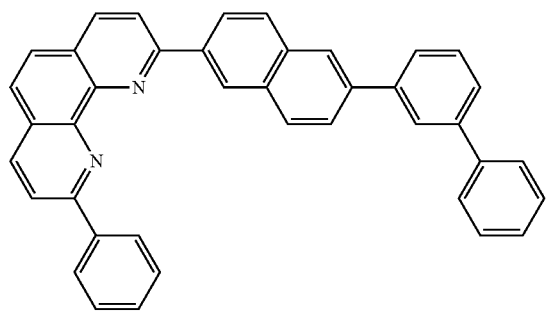
EN-m051
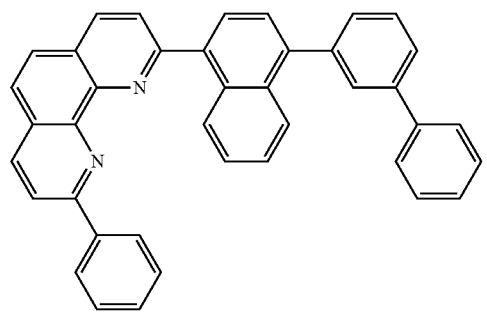
EN-m052
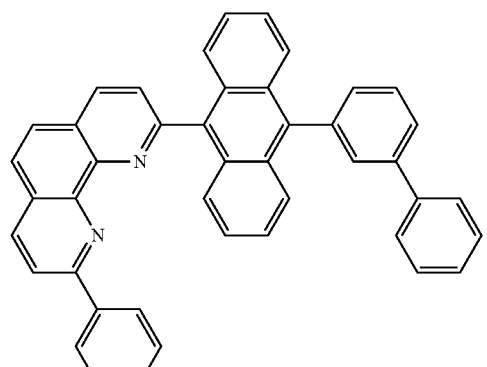
EN-m053
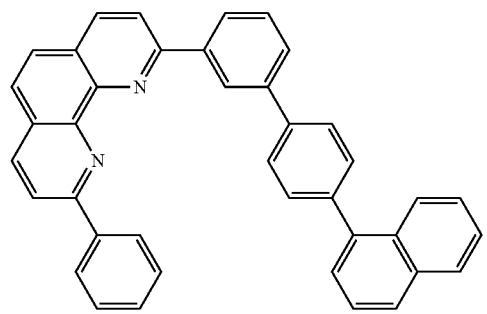
EN-m054
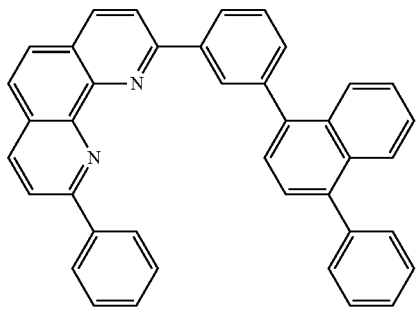
EN-m055
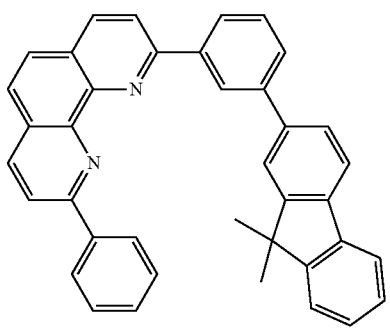

EN-m056
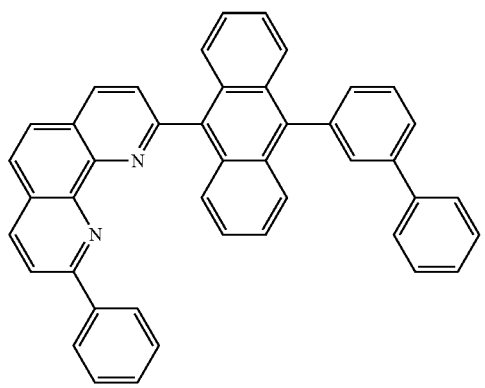
EN-m057
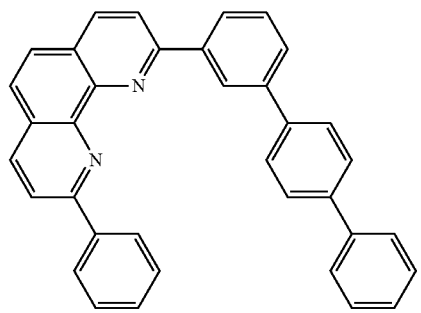
EN-m058
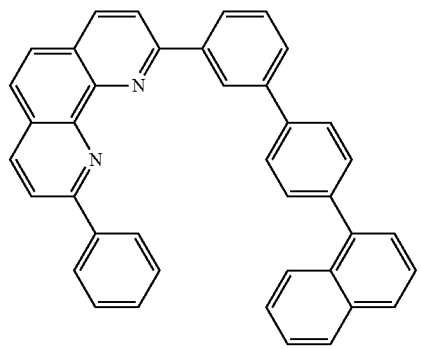
EN-m059
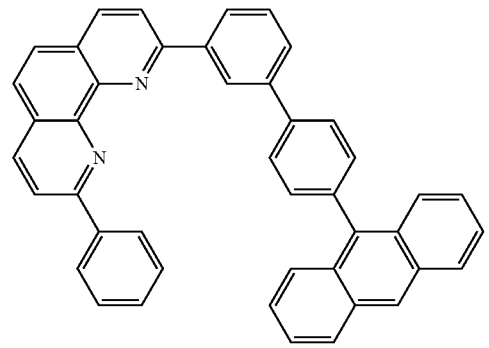
EN-m060
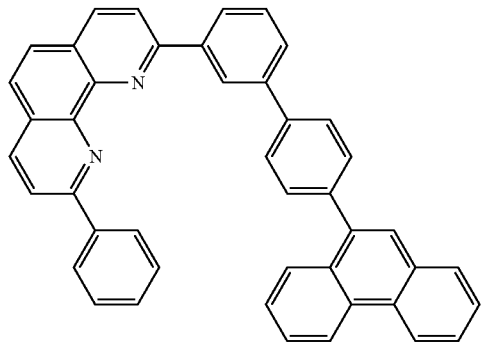
EN-m061
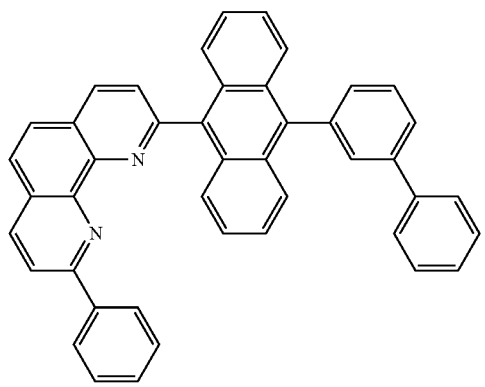
EN-m062
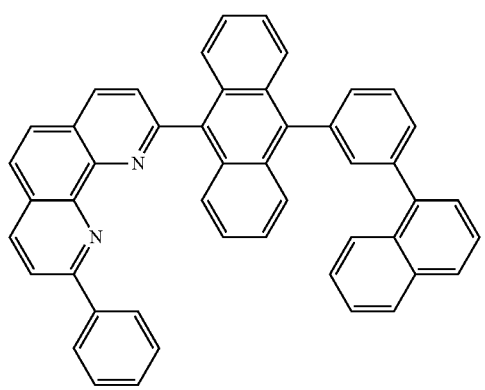
EN-m063
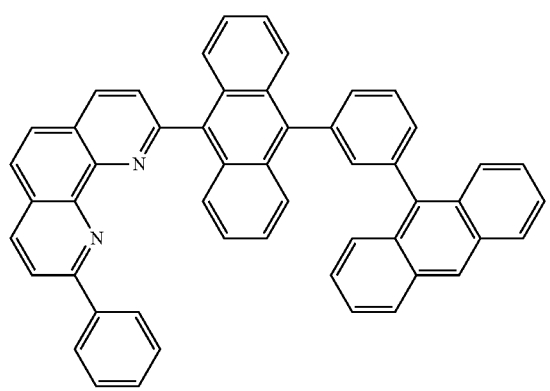

EN-m064
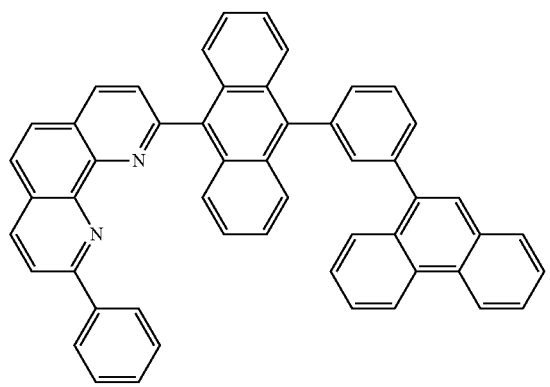
EN-m065
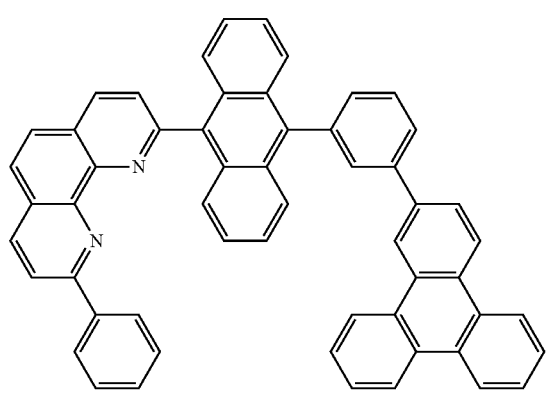
EN-m066
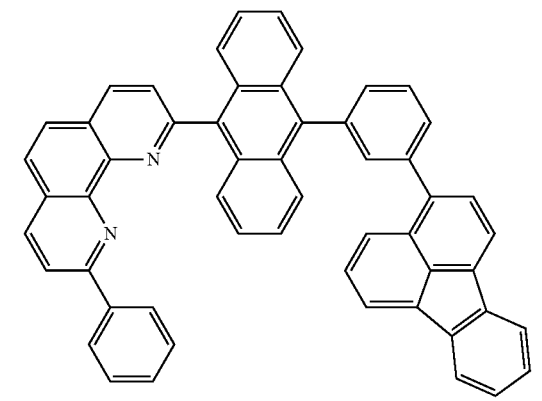
EN-m068
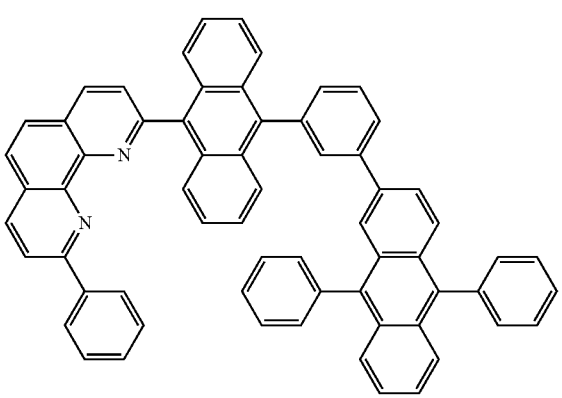
EN-m069
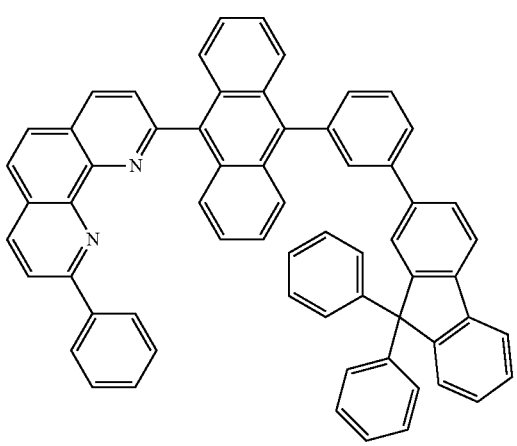
EN-m070
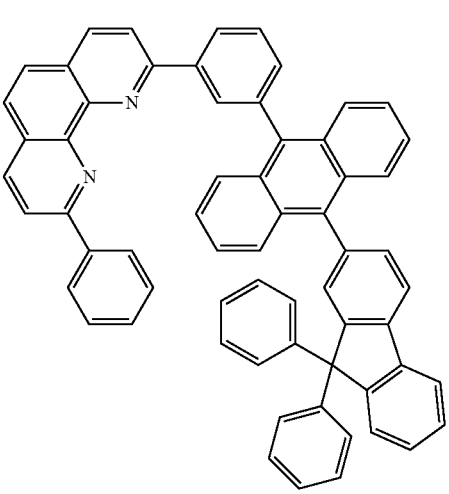
EN-m071
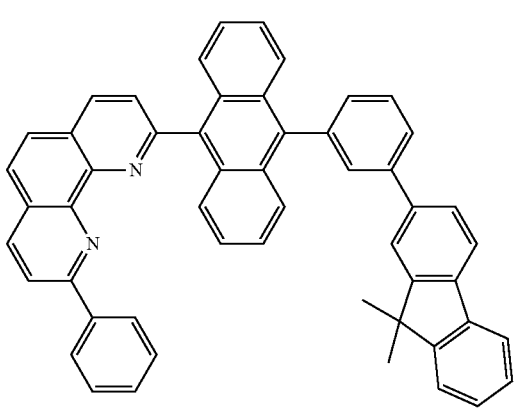

EN-m072
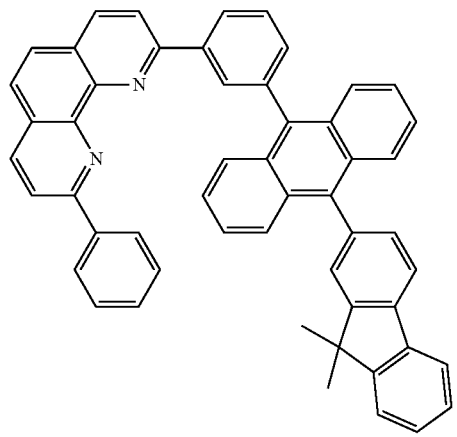
EN-m073
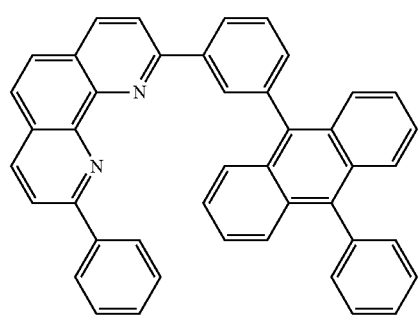
EN-m074
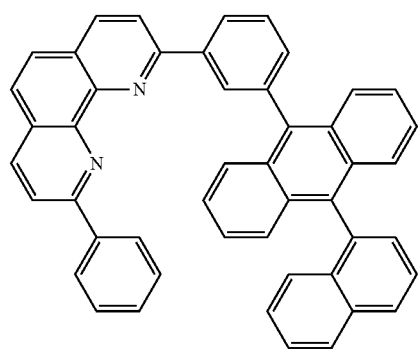
EN-m075
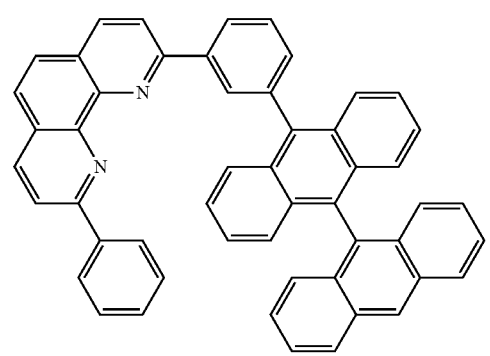
EN-m076
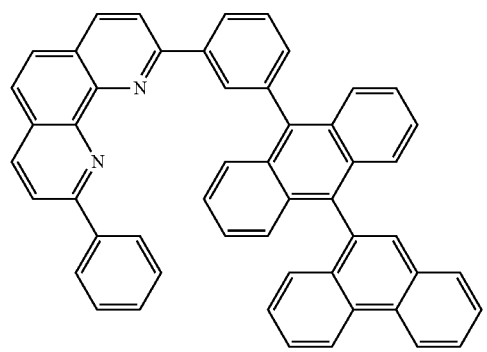
EN-m077
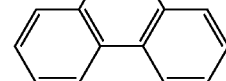
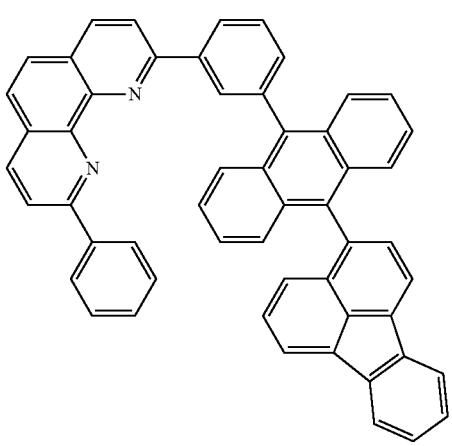
EN-m078

EN-m080
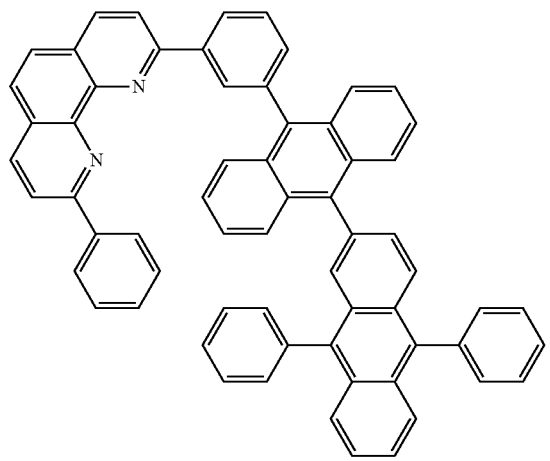
EN-m081
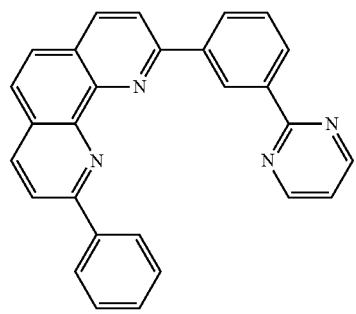
EN-m082
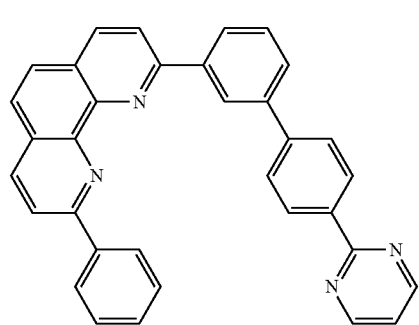
EN-m083
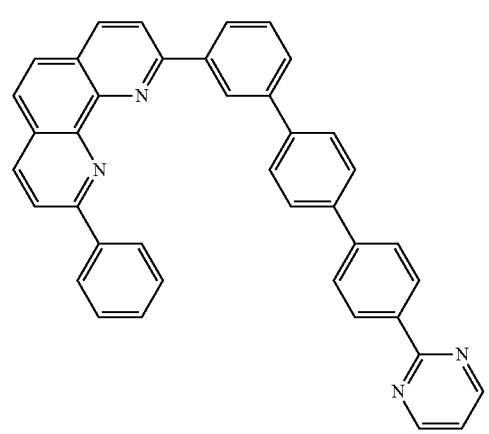
EN-m084
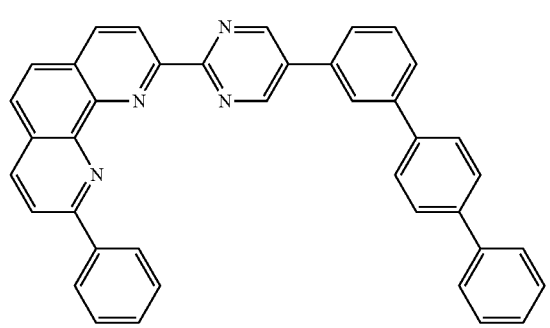
EN-m085
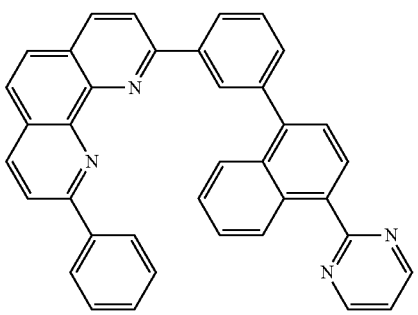
EN-m086
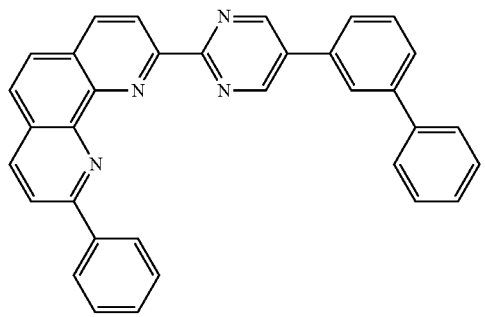
EN-m087
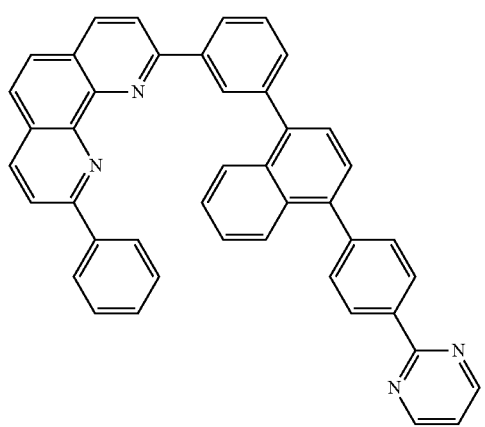

-continued
EN-m088
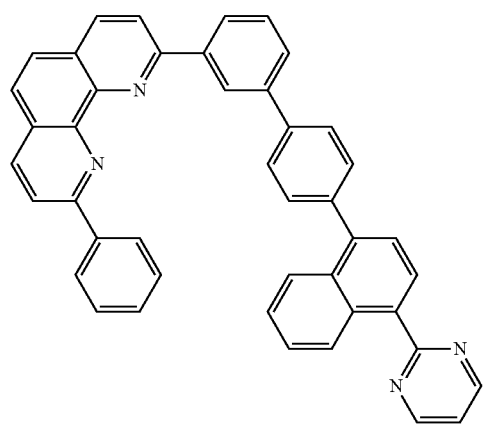
EN-m089
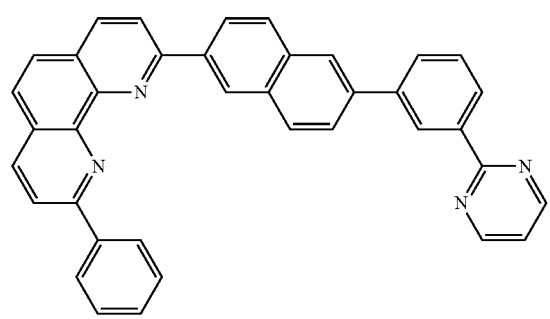
EN-m090
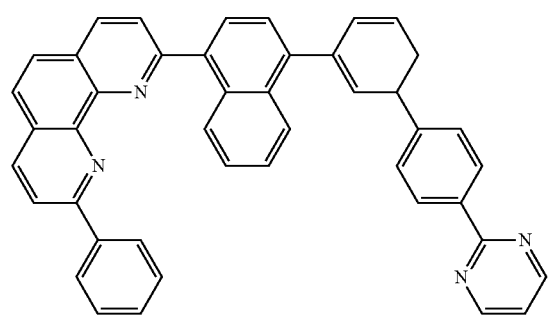
EN-m091
EN-m092
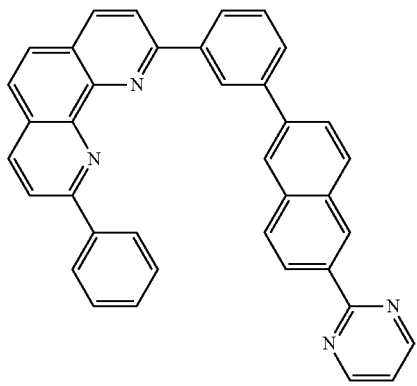
EN-m093
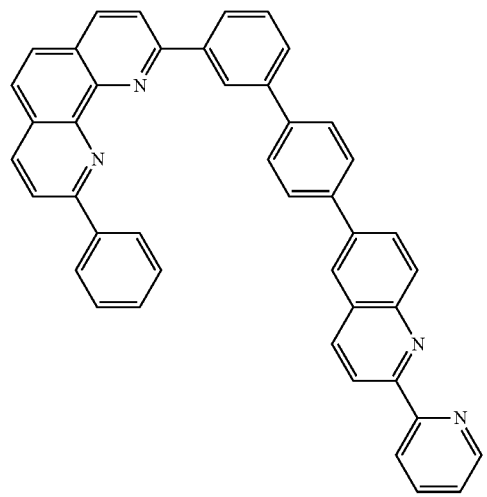
EN-m094
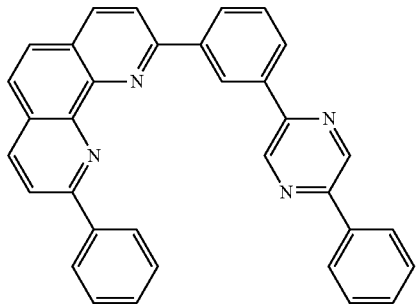
EN-m095
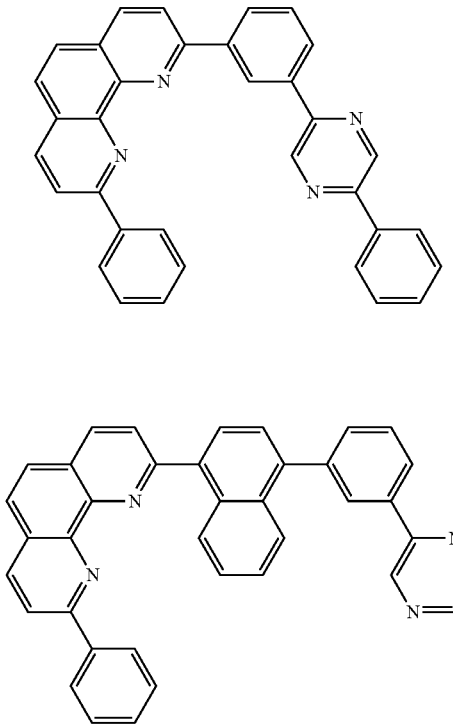

EN-m096
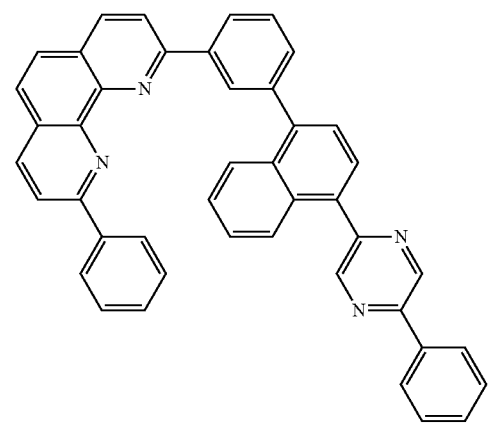
EN-m097
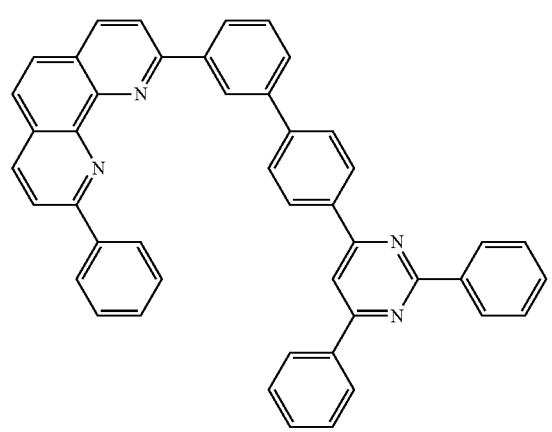
EN-m098
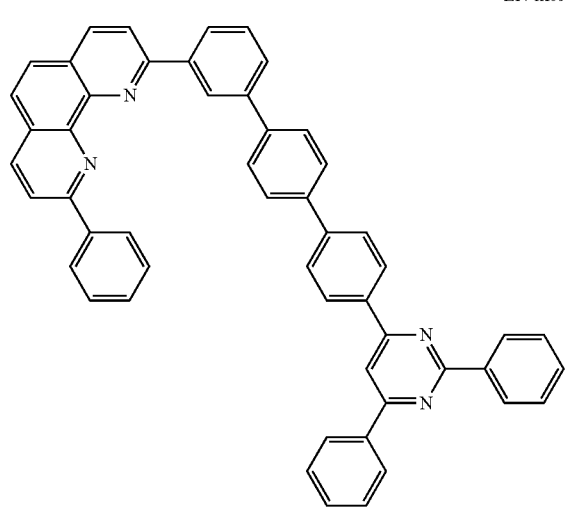
EN-m099
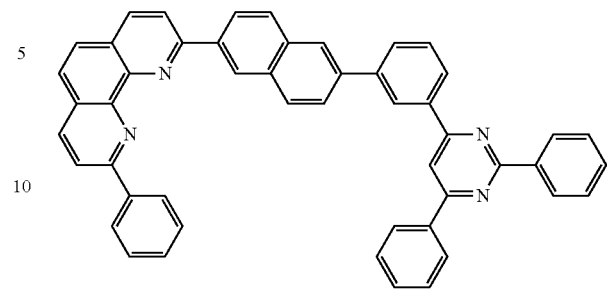
EN-m100
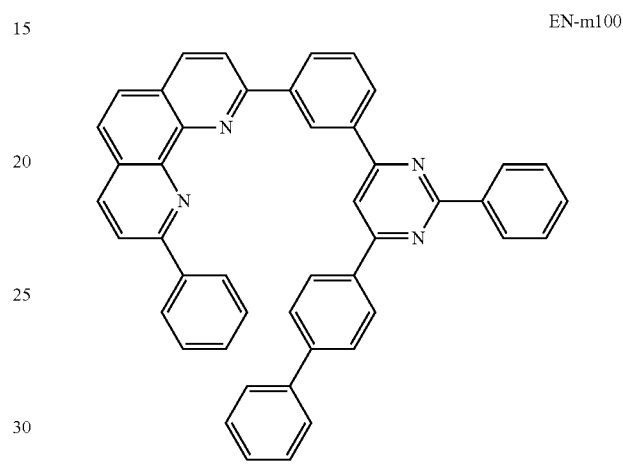
EN-m101
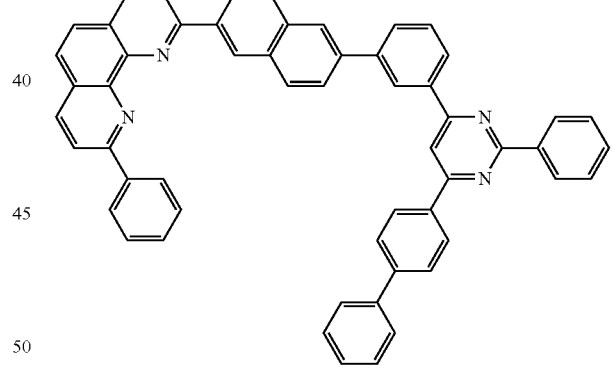
EN-m102
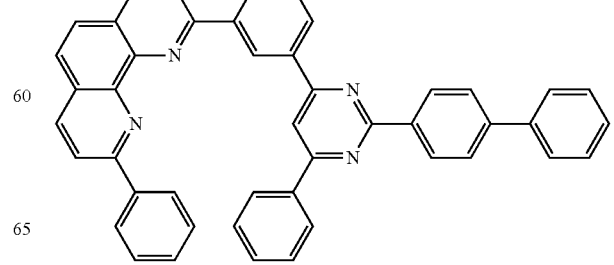

EN-m103
EN-m104
EN-m105
EN-m106
EN-m107
EN-m108
EN-m109
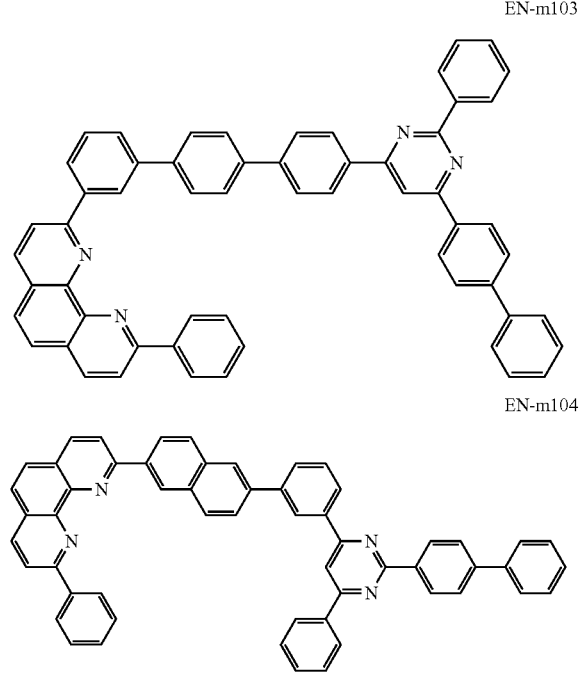
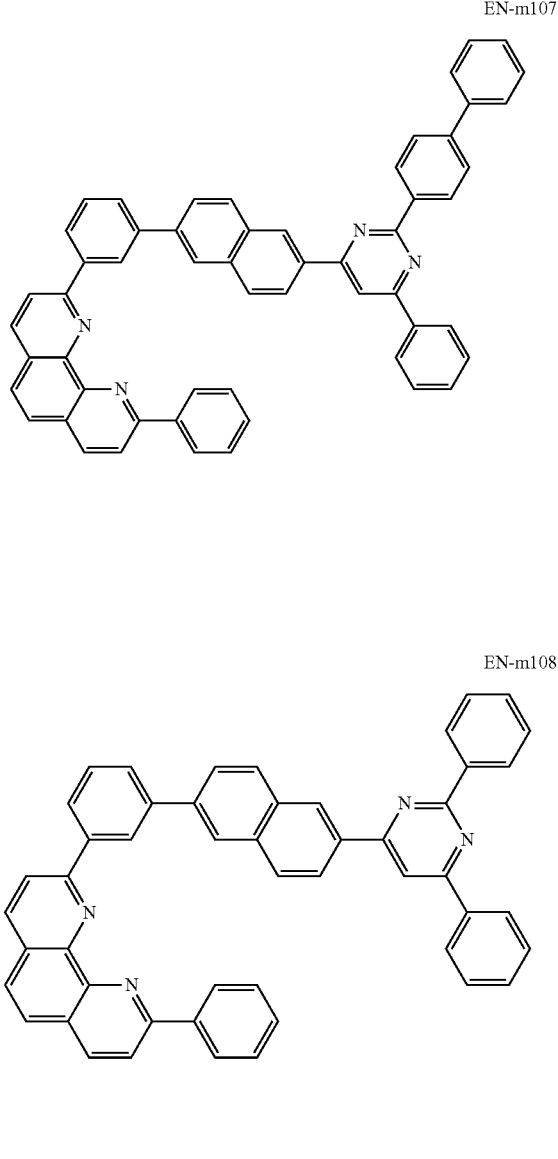
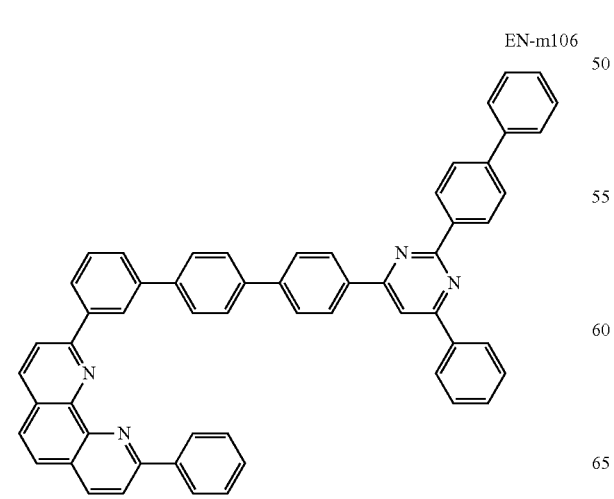

EN-m110
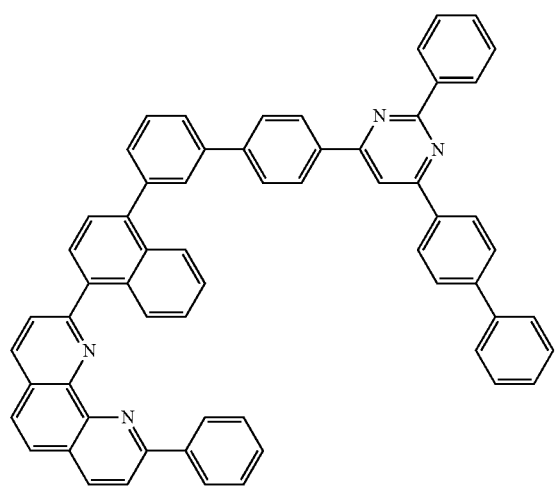
EN-m111
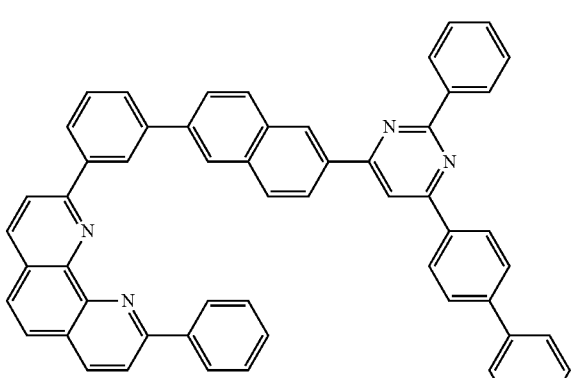
EN-m112
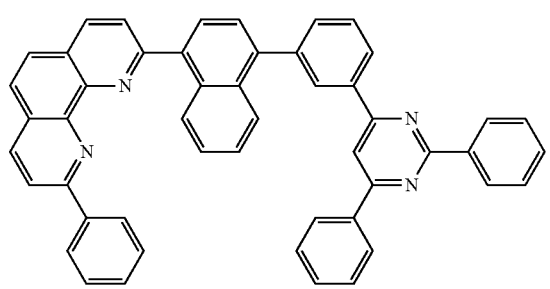
EN-m113
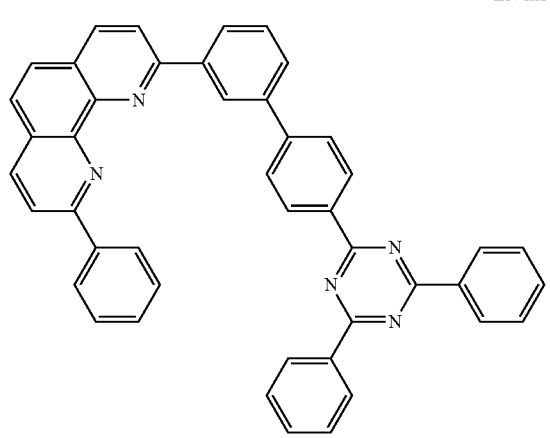
EN-m114
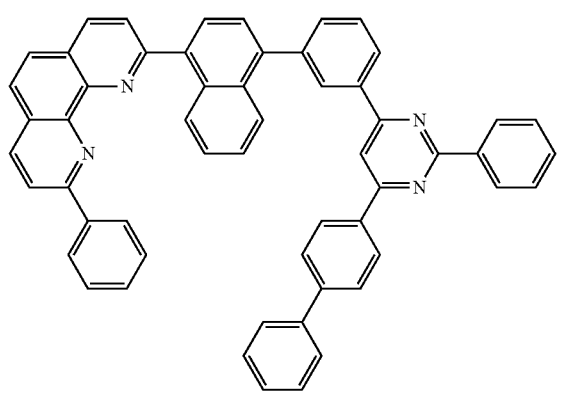
EN-m115
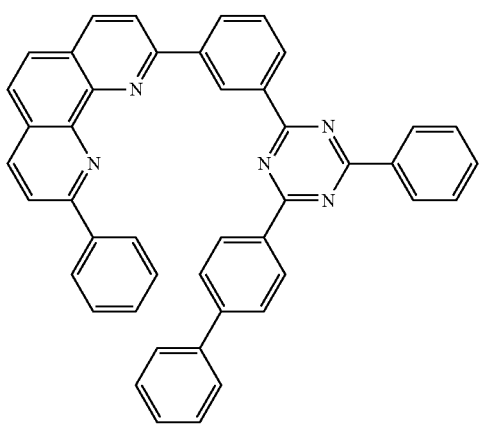
EN-m116
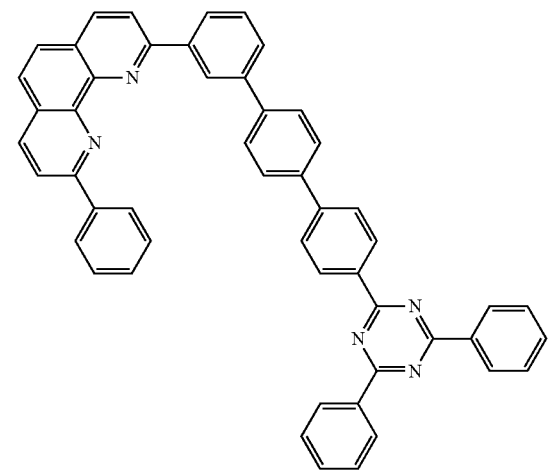
EN-m117
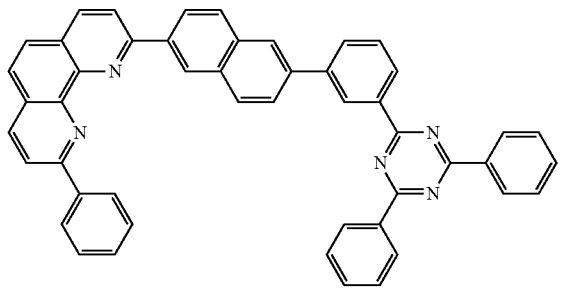

EN-m118
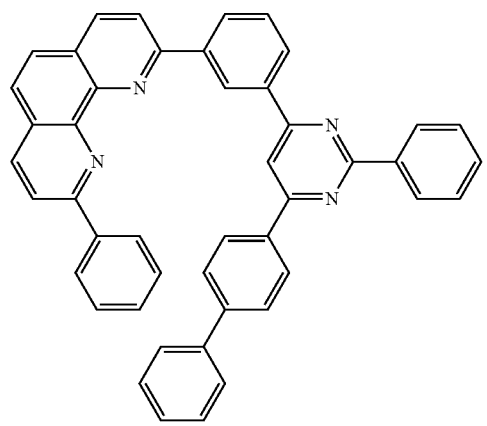
EN-m121
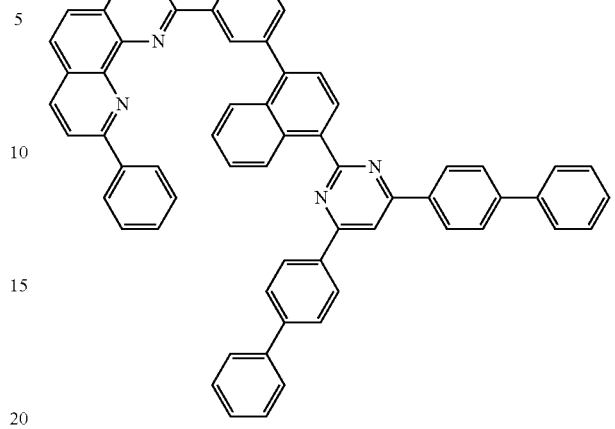
EN-m119
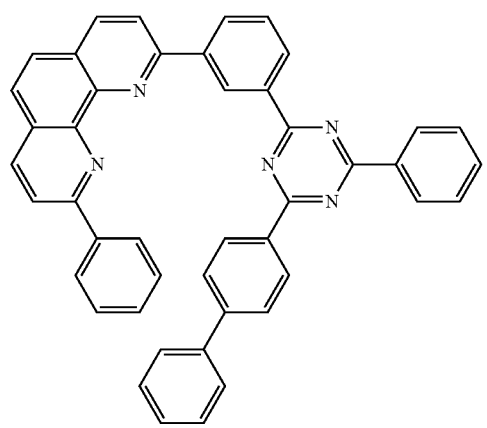
EN-m122
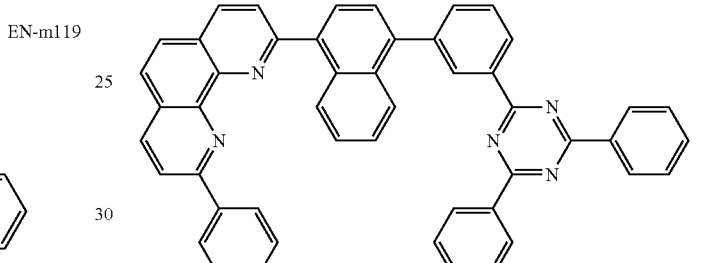
EN-m123
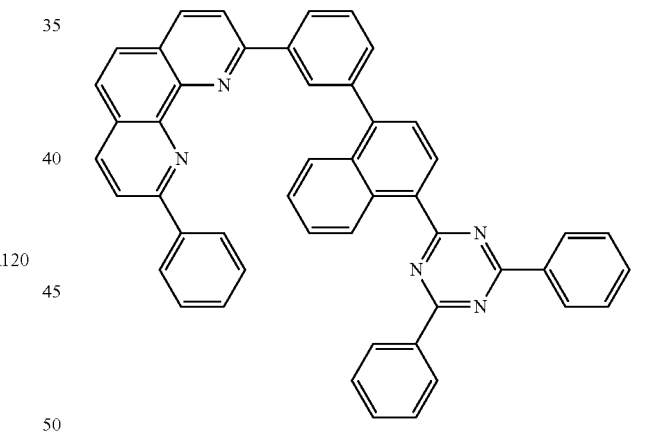
EN-m120
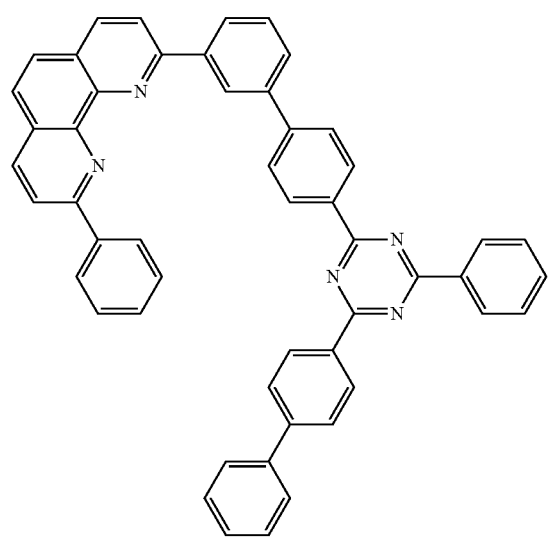
EN-m124
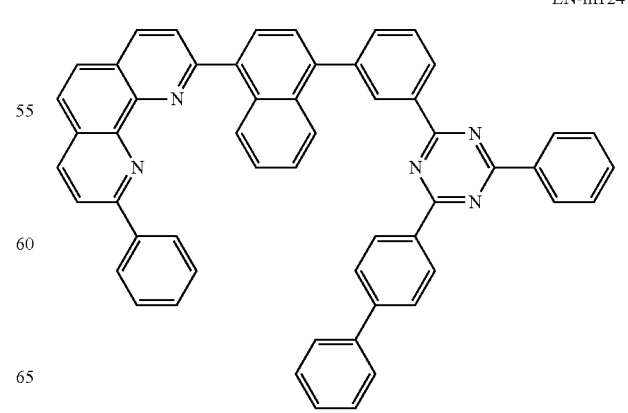

EN-m125
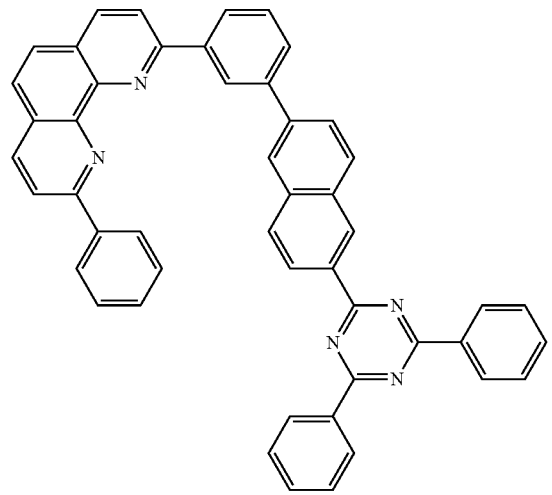
EN-m126
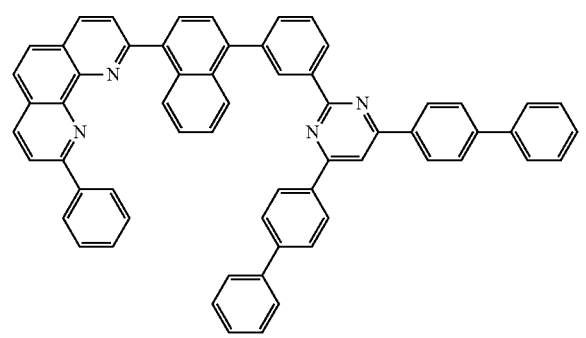
EN-m127
EN-m128
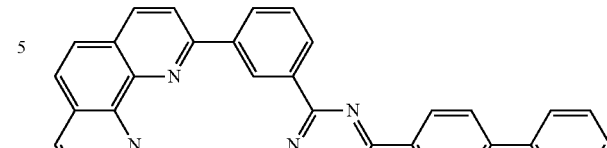
EN-m129
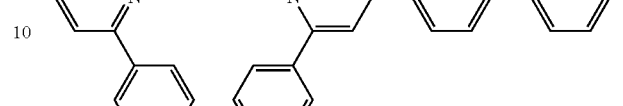
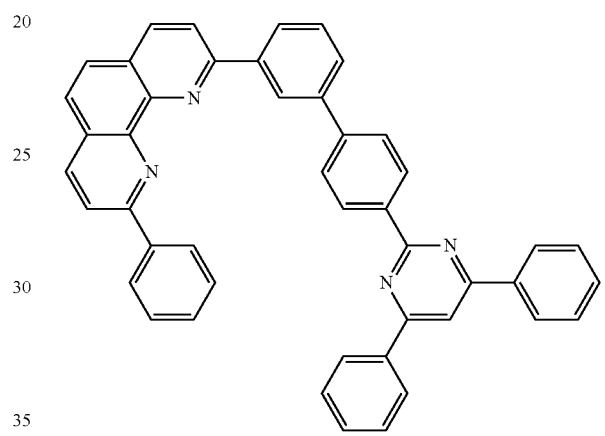
EN-m130
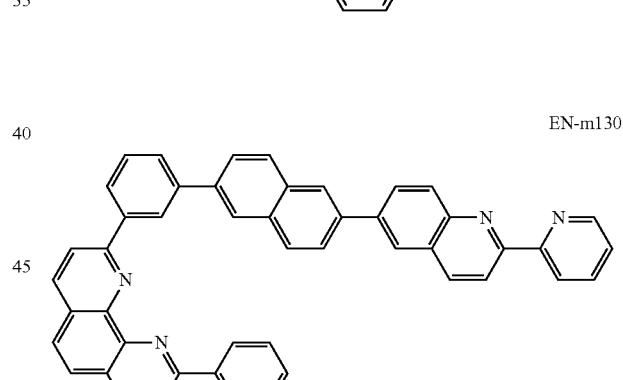
EN-m131
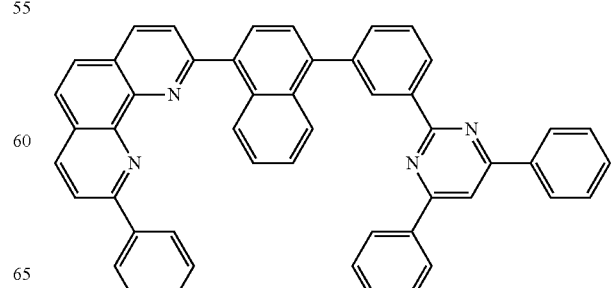

EN-m132
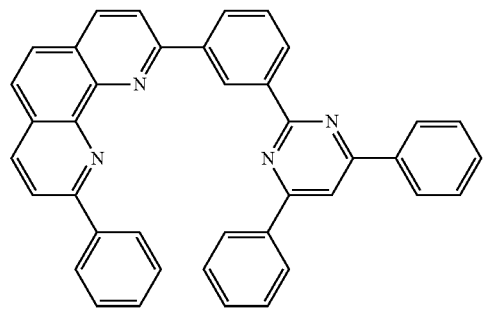
EN-m133
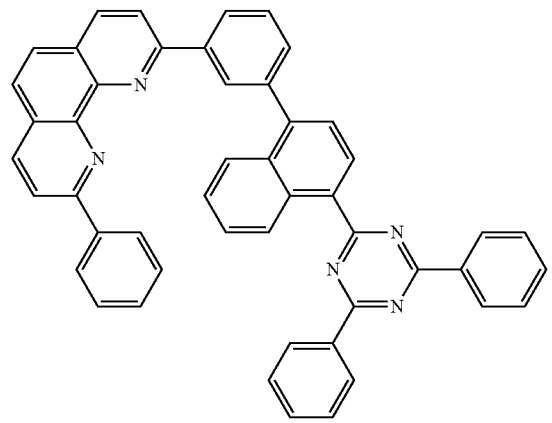
EN-m134
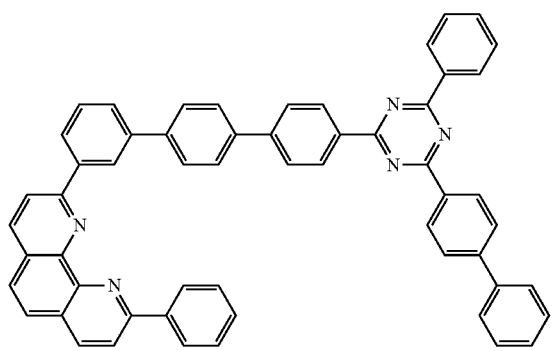
EN-m135
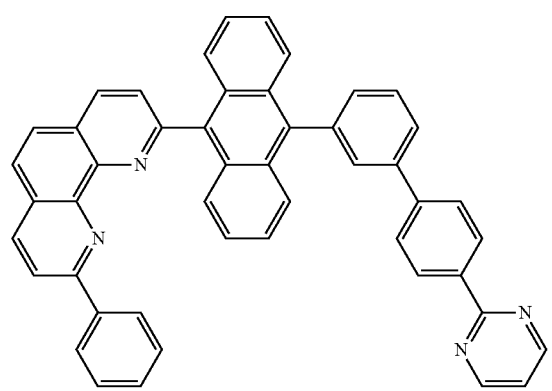
EN-m136
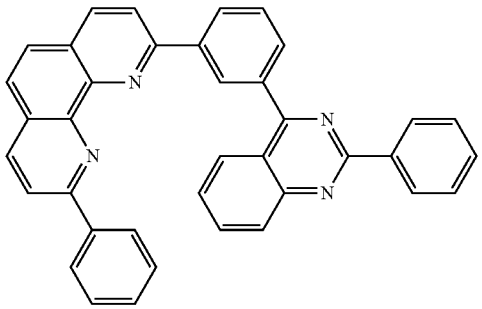
EN-m137
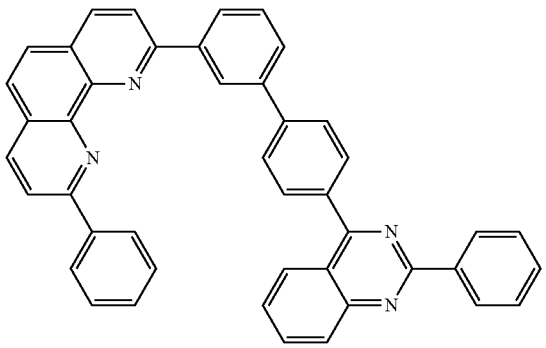
EN-m138
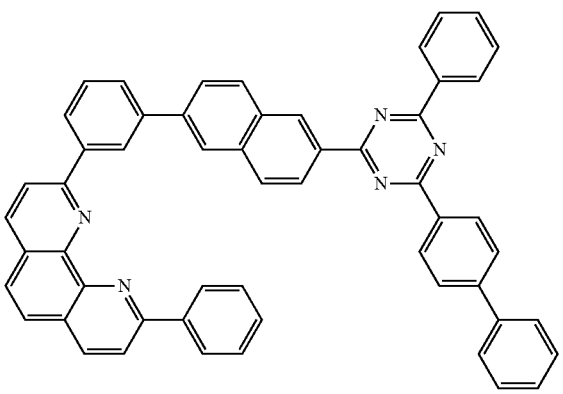
EN-m139
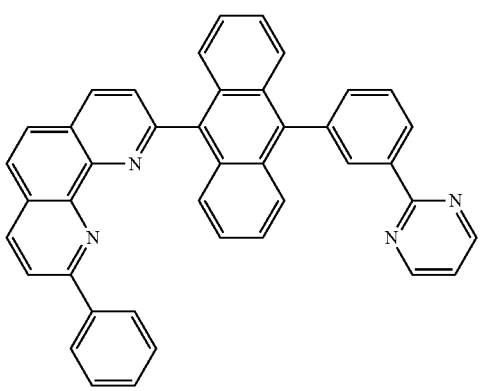

-continued

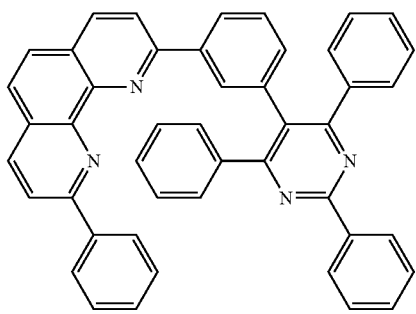
EN-m140

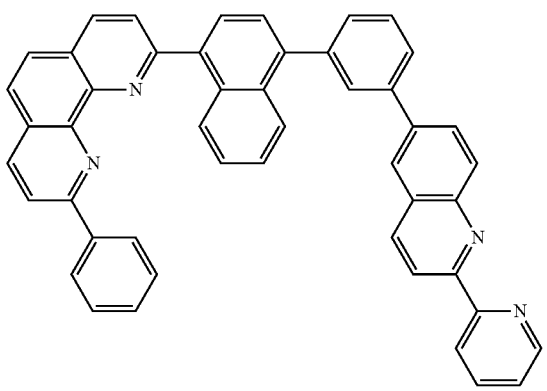
EN-m141

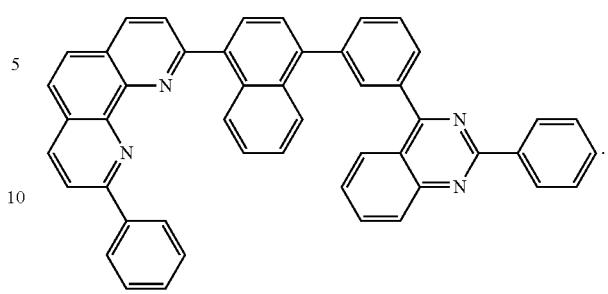
EN-m142

2. The organic light emitting diode according to claim 1, wherein the N-type charge generation layer further comprises an alkali metal or alkali earth metal compound.

3. The organic light emitting diode according to claim 1, further comprising:
   a third light emitting stack interposed between the second light emitting stack and the second electrode and comprising a third light emitting material layer; and
   a second charge generation layer interposed between the second light emitting stack and the third light emitting stack,
   wherein the second charge generation layer comprises the organic compound.

4. An organic light emitting display, comprising:
   a substrate;
   the organic light emitting diode according to claim 1 disposed on the substrate; and
   a driving device interposed between the substrate and the organic light emitting diode and connected to the first electrode.

5. The organic light emitting display according to claim 4, further comprising:
   a color filter interposed between the substrate and the first electrode or disposed on the organic light emitting diode.

\* \* \* \* \*